United States Patent [19]
Reitz et al.

[11] Patent Number: 5,739,166
[45] Date of Patent: Apr. 14, 1998

[54] SUBSTITUTED TERPHENYL COMPOUNDS FOR THE TREATMENT OF INFLAMMATION

[75] Inventors: David B. Reitz; Jinglin Li, both of Chesterfield; Monica B. Norton, Maryland Heights, all of Mo.

[73] Assignee: G.D. Searle & Co., Skokie, Ill.

[21] Appl. No.: 346,433

[22] Filed: Nov. 29, 1994

[51] Int. Cl.$^6$ .................................... A61K 31/18
[52] U.S. Cl. .................. 514/602; 514/464; 514/466; 514/603; 514/709; 514/716; 514/717; 549/437; 549/439; 549/440; 549/443; 549/445; 564/86; 564/89; 568/33; 568/34
[58] Field of Search .................. 549/437, 439, 549/440, 443, 445; 564/86, 89; 568/34, 33; 514/464, 466, 602, 603, 716, 717, 709

[56] References Cited

U.S. PATENT DOCUMENTS

| | | | |
|---|---|---|---|
| 4,180,656 | 12/1979 | Garner | 542/423 |
| 4,990,647 | 2/1991 | Himmler et al. | 558/414 |
| 5,024,743 | 6/1991 | Göler et al. | 204/157.69 |
| 5,238,790 | 8/1993 | Shimura et al. | 430/377 |
| 5,240,928 | 8/1993 | Allen et al. | 514/259 |
| 5,254,546 | 10/1993 | Ardecky et al. | 514/225.8 |
| 5,294,530 | 3/1994 | Seto et al. | 430/551 |
| 5,344,991 | 9/1994 | Reitz et al. | 568/34 |
| 5,393,790 | 2/1995 | Reitz et al. | 514/709 |

FOREIGN PATENT DOCUMENTS

| | | |
|---|---|---|
| 94/15932 | 7/1994 | WIPO. |
| 96/10012 | 4/1996 | WIPO. |

OTHER PUBLICATIONS

R. Copeland, Med. Chem. Res., 5:384–393 (1995).
ca59:12148b, Nov. 1963.
ca63:5571c, Aug. 1965.
ca63:17434d, Dec. 1965.
D. Kim et al, Bioorg. Med. Chem. Lett., 4:41–44, (1979).
Donald J. P. Pinto, Abstract, "Selective In Vitro Inhibition of Cyclooxygenase 2 (COX 2) by Diarylthiophenes and Terphenyls", #018, (Apr. 1995).

Primary Examiner—Brian M. Burn
Attorney, Agent, or Firm—Joseph W. Bulock

[57] ABSTRACT

A class of terphenyl compounds is described for use in treating inflammation and inflammation-related disorders. Compounds of particular interest are defined by Formula II:

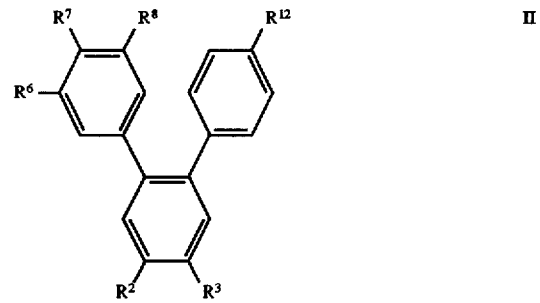

wherein each of $R^2$ and $R^3$ is independently selected from hydrido and halo; or wherein $R^2$ and $R^3$ together form —OCH$_2$O—; wherein each of $R^6$ through $R^8$ is independently selected from hydrido, lower alkyl, halo, lower alkoxy, lower haloalkyl, and lower dialkylamino; or wherein $R^6$ and $R^7$ together form —OCH$_2$O; and wherein $R^{12}$ is selected from lower alkylsulfonyl and aminosulfonyl; or a pharmaceutically-acceptable salt thereof.

47 Claims, No Drawings

SUBSTITUTED TERPHENYL COMPOUNDS FOR THE TREATMENT OF INFLAMMATION

FIELD OF THE INVENTION

This invention is in the field of anti-inflammatory pharmaceutical agents and specifically relates to compounds, compositions and methods for treating inflammation and inflammation-associated disorders, such as arthritis.

BACKGROUND OF THE INVENTION

Prostaglandins play a major role in the inflammation process and the inhibition of prostaglandin production, especially production of $PGG_2$, $PGH_2$ and $PGE_2$, has been a common target of anti-inflammatory drug discovery. However, common non-steroidal anti-inflammatory drugs (NSAIDs) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved.

Previous NSAIDs have been found to prevent the production of prostaglandins by inhibiting enzymes in the human arachidonic acid/prostaglandin pathway, including the enzyme cyclooxygenase (COX). The recent discovery of an inducible enzyme associated with inflammation (named "cyclooxygenase II (COX II)" or "prostaglandin G/H synthase II") provides a viable target of inhibition which more effectively reduces inflammation and produces fewer and less drastic side effects.

Substituted biphenyl compounds have been reported as components in photographic materials. U.S. Pat. No. 5,238,790, to Shimura et al, describes the use of biphenyl compounds as dispersion agents in photographic materials U.S. Pat. No. 5,294,530, to Seto et al, describes photographic materials containing biphenyl compounds as anti-fading agents.

U.S. Pat. No. 4,990,647, to Himmler et al, describes a method for the preparation of unsymmetric biaryl compounds.

Substituted biphenyl compounds have been reported as having activity as angiotensin II antagonists. Heterocyclo-substituted biphenyl compounds are described by D. Kim, et al [Bioorg. Med. Chem. Lett., 4, 41–44(1994)]. U.S. Pat. No. 5,254,546, to Ardecky et al, describes tetrazole substituted biphenyl compounds. U.S. Pat. No. 5,240,928, to Allen et al, describes aminosulfonyl-substituted biphenyl compounds.

However, terphenyl compounds have not been previously described, especially as antiinflammatory agents.

DESCRIPTION OF THE INVENTION

A class of compounds useful in treating inflammation-related disorders is defined by Formula I:

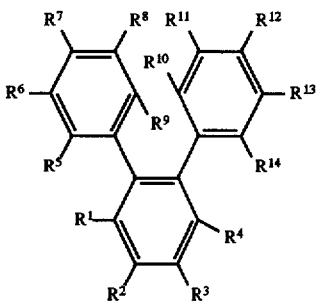

wherein each of $R^1$ through $R^4$ is independently selected from hydrido, halo, and alkoxy; wherein each of $R^5$ through $R^{14}$ is independently selected from hydrido, alkyl, halo, alkoxy, alkylthio, cyano, haloalkyl, amino, alkylamino, dialkylamino, haloalkoxy, hydroxyalkyl, alkoxyalkyl, hydroxyl, mercapto, aminosulfonyl and alkylsulfonyl; or a pharmaceutically-acceptable salt thereof.

Compounds of Formula I would be useful for, but not limited to, the treatment of inflammation in a subject, and for treatment of other inflammation-associated disorders, such as, as an analgesic in the treatment of pain and headaches, or as an antipyretic for the treatment of fever. For example, compounds of Formula I would be useful to treat arthritis, including but not limited to rheumatoid arthritis, spondyloarthropathies, gouty arthritis, osteoarthritis, systemic lupus erythematosus and juvenile arthritis. Such compounds of Formula I would be useful in the treatment of asthma, bronchitis, menstrual cramps, tendinitis, bursitis, and skin related conditions such as psoriasis, eczema, burns and dermatitis. Compounds of Formula I also would be useful to treat gastrointestinal conditions such as inflammatory bowel disease, Crohn's disease, gastritis, irritable bowel syndrome and ulcerative colitis and for the prevention of colorectal cancer. Compounds of Formula I would be useful in treating inflammation in such diseases as vascular diseases, migraine headaches, periarteritis nodosa, thyroiditis, aplastic anemia, Hodgkin's disease, sclerodoma, rheumatic fever, type I diabetes, myasthenia gravis, sarcoidosis, nephrotic syndrome, Behcet's syndrome, polymyositis, gingivitis, hypersensitivity, conjunctivitis, swelling occurring after injury, myocardial ischemia, and the like. The compounds are useful as antiinflammatory agents, such as for the treatment of arthritis, with the additional benefit of having significantly less harmful side effects.

The present invention preferably includes compounds which selectively inhibit cyclooxygenase II over cyclooxygenase I. Preferably, the compounds have a cyclooxygenase II $IC_{50}$ of less than about 0.2–2 μM, and also have a selectivity ratio of cyclooxygenase II inhibition over cyclooxygenase I inhibition of at least 50, and more preferably of at least 100. Even more preferably, the compounds have a cyclooxygenase II $IC_{50}$ of greater than about 1 μM, and more preferably of greater than 10 μM. Such preferred selectivity may indicate an ability to reduce the incidence of common NSAID-induced side effects.

A preferred class of compounds consists of those compounds of Formula I wherein each of $R^1$ through $R^4$ is independently selected from hydrido and halo; or wherein $R^2$ and $R^3$ together form —$OCH_2O$—; and wherein each of $R^5$ through $R^{14}$ is independently selected from hydrido, lower alkyl, halo, lower alkoxy, lower alkylthio, cyano, lower haloalkyl, amino, lower alkylamino, lower dialkylamino, lower haloalkoxy, lower hydroxyalkyl, lower alkoxyalkyl, hydroxyl, mercapto, aminosulfonyl and lower alkylsulfonyl; or wherein $R^6$ and $R^7$ together form —$OCH_2O$—.

A more preferred class of compounds consists of those compounds of Formula I wherein each of $R^1$ through $R^4$ is independently selected from hydrido and halo; or wherein $R^2$ and $R^3$ together form —$OCH_2O$—; wherein each of $R^5$ through $R^8$ is independently selected from hydrido, lower alkyl, halo, lower alkoxy, lower haloalkyl, and lower dialkylamino; or wherein $R^6$ and $R^7$ together form —$OCH_2O$—; wherein $R^{10}$, $R^{11}$, $R^{13}$ and $R^{14}$ are hydrido; and wherein $R^{12}$ is selected from aminosulfonyl and lower alkylsulfonyl.

Within Formula I there is a subclass of compounds which consists of compounds wherein each of $R^1$ through $R^4$ is independently selected from hydrido and halo; or wherein $R^2$ and $R^3$ together form —$OCH_2O$—; wherein each of $R^5$ and $R^9$ is hydrido; wherein each of $R^6$ through $R^8$ is independently selected from hydrido, lower alkyl, halo, lower alkoxy, lower haloalkyl, and lower dialkylamino; or wherein $R^6$ and $R^7$ together form —$OCH_2O$—; wherein $R^{10}$, $R^{11}$, $R^{13}$ and $R^{14}$ are hydrido; and wherein $R^{12}$ is aminosulfonyl.

A class of compounds of particular interest consists of those compounds of Formula I wherein each of $R^1$ through $R^4$ is independently selected from hydrido, fluoro, chloro and bromo; or wherein $R^2$ and $R^3$ together form —$OCH_2O$—; wherein each of $R^5$ and $R^9$ is hydrido; wherein each of $R^6$ through $R^8$ is independently selected from hydrido, methyl, ethyl, fluoro, chloro, bromo, methoxy, ethoxy, propoxy, n-butoxy, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, N-ethyl-N-methylamino, N,N-dimethylamino, and N,N-diethylamino; or wherein $R^6$ and $R^7$ together form —$OCH_2O$—; wherein $R^{10}$, $R^{11}$, $R^{13}$ and $R^{14}$ are hydrido; and wherein $R^{12}$ is aminosulfonyl.

Within Formula I there is a second subclass of compounds of high interest wherein each of $R^1$ and $R^4$ are hydrido; wherein each of $R^2$ and $R^3$ is independently selected from hydrido and halo; or wherein $R^2$ and $R^3$ together form —$OCH_2O$—; wherein each of $R^5$ and $R^9$ is hydrido; wherein each of $R^6$ through $R^8$ is independently selected from hydrido, lower alkyl, halo, and lower alkoxy; or wherein $R^6$ and $R^7$ together form —$OCH_2O$—; wherein $R^{10}$, $R^{11}$, $R^{13}$ and $R^{14}$ are hydrido; and wherein $R^{12}$ is lower alkylsulfonyl.

A class of compounds of particular interest consists of those compounds of Formula I wherein each of $R^1$ and $R^4$ are hydrido; wherein each of $R^2$ and $R^3$ is independently selected from hydrido, fluoro, chloro and bromo; or wherein $R^2$ and $R^3$ together form —$OCH_2O$—; wherein each of $R^5$ and $R^9$ is hydrido; wherein each of $R^6$ through $R^8$ is independently selected from hydrido, methyl, ethyl, fluoro, chloro, bromo, methoxy, ethoxy, propoxy, and n-butoxy; or wherein $R^6$ and $R^7$ together form —$OCH_2O$—; wherein $R^{10}$, $R^{11}$, $R^{13}$ and $R^{14}$ are hydrido; and wherein $R^{12}$ is methylsulfonyl.

A family of specific compounds of particular interest within Formula I consists of compounds and pharmaceutically-acceptable salts thereof as follows:

4-[2-biphenyl]benzenesulfonamide;
4-[2-(3-methylphenyl)phenyl]benzenesulfonamide;
4-[2-(3-methoxyphenyl)phenyl]benzenesulfonamide;
4-[2-(3-fluorophenyl)phenyl]benzenesulfonamide;
4-[2-(3-chlorophenyl)phenyl]benzenesulfonamide;
4-[2-(3-trifluoromethylphenyl)phenyl]benzenesulfonamide;
4-[2-[3-(N,N-dimethylamino)phenyl]phenyl]benzenesulfonamide;
4-[2-(4-methylphenyl)phenyl]benzenesulfonamide;
4-[2-(3,4-dimethylphenyl)phenyl]benzenesulfonamide;
4-[2-(3-methoxy-4-methylphenyl)phenyl]benzenesulfonamide;
4-[2-(3-fluoro-4-methylphenyl)phenyl]benzenesulfonamide;
4-[2-(3-chloro-4-methylphenyl)phenyl]benzenesulfonamide;
4-[2-(4-methyl-3-trifluoromethylphenyl)phenyl]benzenesulfonamide;
4-[2-[3-(N,N-dimethylamino)-4-methylphenyl]phenyl]benzenesulfonamide;
4-[2-4-methoxyphenyl)phenyl]benzenesulfonamide;
4-[2-4-methoxy-3-methylphenyl)phenyl]benzenesulfonamide;
4-[2-3,4-dimethoxyphenyl)phenyl]benzenesulfonamide;
4-[2-3-fluoro-4-methoxyphenyl)phenyl]benzenesulfonamide;
4-[2-3-chloro-4-methoxyphenyl)phenyl]benzenesulfonamide
4-[2-4-methoxy-3-trifluoromethylphenyl)phenyl]benzenesulfonamide;
4-[2-[3-(N,N-dimethylamino)-4-methoxyphenyl]phenyl]benzenesulfonamide;
4-[2-(4-fluorophenyl)phenyl]benzenesulfonamide;
4-[2-(4-fluoro-3-methylphenyl)phenyl]benzenesulfonamide;
4-[2-(4-fluoro-3-methoxyphenyl)phenyl]benzenesulfonamide;
4-[2-(3,4-difluorophenyl)phenyl]benzenesulfonamide;
4-[2-(3-chloro-4-fluorophenyl)phenyl]benzenesulfonamide;
4-[2-(4-fluoro-3-trifluoromethylphenyl)phenyl]benzenesulfonamide;
4-[2-[3-(N,N-dimethylamino)-4-fluorophenyl]phenyl]benzenesulfonamide;
4-[2-(4-chlorophenyl)phenyl]benzenesulfonamide;
4-[2-(4-chloro-3-methlphenyl)phenyl]benzenesulfonamide;
4-[2-(4-chloro-3-methoxyphenyl)phenyl]benzenesulfonamide;
4-[2-(4-chloro-3-fluorophenyl)phenyl]benzenesulfonamide;
4-[2-(3,4-dichlorophenyl)phenyl]benzenesulfonamide;
4-[2-(4-chloro-3-trifluoromethylphenyl)phenyl]benzenesulfonamide;
4-[2-[4-chloro-3-(N,N-dimethylamino)phenyl]phenyl]benzenesulfonamide;
4-[2-(4-trifluoromethylphenyl)phenyl]benzenesulfonamide;
4-[2-(3-methyl-4-trifluoromethylphenyl)phenyl]benzenesulfonamide;
4-[2-(3-methoxy-4-trifluoromethylphenyl)phenyl]benzenesulfonamide;
4-[2-(3-fluoro-4-trifluoromethylphenyl)phenyl]benzenesulfonamide;
4-[2-(3-chloro-4-trifluoromethylphenyl)phenyl]benzenesulfonamide;
4-[2-[3,4-di(trifluoromethyl)phenyl]phenyl]benzenesulfonamide;
4-[2-[3-(N,N-dimethylamino)-4-trifluoromethylphenyl]phenyl]benzenesulfonamide;
4-[2-[4-(N,N-dimethylamino)phenyl]phenyl]benzenesulfonamide;
4-[2-[4-(N,N-dimethylamino)-3-methylphenyl]phenyl]benzenesulfonamide;
4-[2-[4-(N,N-dimethylamino)-3-methoxyphenyl]phenyl]benzenesulfonamide;
4-[2-[4-(N,N-dimethylamino)-3-fluorophenyl]phenyl]benzenesulfonamide;
4-[2-[3-chloro-4-(N,N-dimethylamino)phenyl]phenyl]benzenesulfonamide;

4-[2-[4-(N,N-dimethylamino)-3-trifluoromethylphenyl] phenyl]benzenesulfonamide;
4-[2-[3,4-di (N,N-dimethylamino)phenyl]phenyl] benzenesulfonamide;
4-[2-(3,5-dimethylphenyl)phenyl]benzenesulfonamide;
4-[2-(3,5-dimethoxyphenyl)phenyl]benzenesulfonamide;
4-[2-(3,5-difluorophenyl)phenyl]benzenesulfonamide;
4-[2-(3,5-dichlorophenyl)phenyl]benzenesulfonamide;
4-[2-[3,5-di(trifluoromethyl)phenyl]phenyl] benzenesulfonamide;
4-[2-[3,5-di(N,N-dimethylamino)phenyl]phenyl] benzenesulfonamide;
4-[2-(3,4,5-trimethylphenyl)phenyl]benzenesulfonamide;
4-[2-(3,5-dimethoxy-4-methylphenyl)phenyl] benzenesulfonamide;
4-[2-(3,5-difluoro-4-methylphenyl)phenyl] benzenesulfonamide;
4-[2-(3,5-dichloro-4-methylphenyl)phenyl] benzenesulfonamide;
4-[2-[3,5-di(trifluoromethyl)-4-methylphenyl]phenyl] benzenesulfonamide;
4-[2-[3,5-di(N,N-dimethylamino)-4-methylphenyl]phenyl] benzenesulfonamide;
4-[2-(3,5-dimethyl-4-methoxyphenyl)phenyl] benzenesulfonamide;
4-[2-(3,4,5-trimethoxyphenyl)phenyl]benzenesulfonamide;
4-[2-(3,5-difluoro-4-methoxyphenyl)phenyl] benzenesulfonamide;
4-[2-(3,5-dichloro-4-methoxyphenyl)phenyl] benzenesulfonamide;
4-[2-[3,5-di(trifluoromethyl)-4-methoxyphenyl]phenyl] benzenesulfonamide;
4-[2-[3,5-di(N,N-dimethylamino)-4-methoxyphenyl] phenyl]benzenesulfonamide;
4-[2-(3,5-dimethyl-4-fluorophenyl)phenyl] benzenesulfonamide;
4-[2-(3,5-dimethoxy-4-fluorophenyl)phenyl] benzenesulfonamide;
4-[2-(3,4,5-trifluorophenyl)phenyl]benzenesulfonamide;
4-[2-(3,5-dichloro-4-fluorophenyl)phenyl] benzenesulfonamide;
4-[2-[3,5-di(trifluoromethyl)-4-fluorophenyl]phenyl] benzenesulfonamide;
4-[2-[3,5-di(N,N-dimethylamino)-4-fluorophenyl]phenyl] benzenesulfonamide;
4-[2-(4-chloro-3,5-dimethylphenyl)phenyl] benzenesulfonamide;
4-[2-(4-chloro-3,5-dimethoxyphenyl)phenyl] benzenesulfonamide;
4-[2-(4-chloro-3,5-difluorophenyl)phenyl] benzenesulfonamide;
4-[2-(3,4,5-trichlorophenyl)phenyl]benzenesulfonamide;
4-[2-[4-chloro-3,5-di(trifluoromethyl)phenyl]phenyl] benzenesulfonamide;
4-[2-[4-chloro-3,5-di(N,N-dimethylamino)phenyl]phenyl] benzenesulfonamide;
4-[2-(3,5-dimethyl-4-(trifluoromethylphenyl)phenyl] benzenesulfonamide;
4-[2-(3,5-dimethoxy-4-trifluoromethylphenyl)phenyl] benzenesulfonamide;
4-[2-(3,5-difluoro-4-trifluoromethylphenyl)phenyl] benzenesulfonamide;
4-[2-(3,5-dichloro-4-trifluoromethylphenyl)phenyl] benzenesulfonamide;
4-[2-[3,4,5-tri(trifluoromethyl)-phenyl]phenyl] benzenesulfonamide;
4-[2-[3,5-di(N,N-dimethylamino)-4-trifluoromethylphenyl] phenyl]benzenesulfonamide;
4-[2-[3,5-dimethyl-4-(N,N-dimethylamino)phenyl]phenyl] benzenesulfonamide;
4-[2-[3,5-dimethoxy-4-(N,N-dimethylamino)phenyl] phenyl]benzenesulfonamide;
4-[2-[3,5-difluoro-4-(N,N-dimethylamino)phenyl]phenyl] benzenesulfonamide;
4-[2-[3,5-dichloro-4-(N,N-dimethylamino)phenyl]phenyl] benzenesulfonamide;
4-[2-[4-(N,N-dimethylamino)-3,5-di(trifluoromethyl) phenyl]phenyl]benzenesulfonamide;
4-[2-[3,4,5-tri(N,N-dimethylamino)phenyl]phenyl] benzenesulfonamide;
4-[6-phenyl-1,3-benzodioxol-5-yl]benzenesulfonamide;
4-[6-(3-methylphenyl)-1,3-benzodioxol-5-yl] benzenesulfonamide;
4-[6-(3-fluorophenyl)-1,3-benzodioxol-5-yl] benzenesulfonamide;
4-[6-(3-chlorophenyl)-1,3-benzodioxol-5-yl] benzenesulfonamide;
4-[6-(3-methoxyphenyl)-1,3-benzodioxol-5-yl] benzenesulfonamide;
4-[6-(3-trifluoromethylphenyl)-1,3-benzodioxol-5-yl] benzenesulfonamide;
4-[6-[3-(N,N-dimethylamino)phenyl]-1,3-benzodioxol-5-yl]benzenesulfonamide;
4-[6-(4-methylphenyl)-1,3-benzodioxol-5-yl] benzenesulfonamide;
4-[6-(3,4-dimethylphenyl)-1,3-benzodioxol-5-yl] benzenesulfonamide;
4-[6-(3-fluoro-4-methylphenyl)-1,3-benzodioxol-5-yl] benzenesulfonamide;
4-[6-(3-chloro-4-methylphenyl)-1,3-benzodioxol-5-yl] benzenesulfonamide;
4-[6-(3-methoxy-4-methylphenyl)-1,3-benzodioxol-5-yl] benzenesulfonamide;
4-[6-(4-methyl-3-trifluoromethylphenyl)-1,3-benzodioxol-5-yl]benzenesulfonamide;
4-[6-[3-(N,N-dimethylamino)-4-methylphenyl]-1,3-benzodioxol-5-yl]benzenesulfonamide;
4-[6-4-methoxyphenyl)-1,3-benzodioxol-5-yl] benzenesulfonamide;
4-[6-4-methoxy-3-methylphenyl)-1,3-benzodioxol-5-yl] benzenesulfonamide;
4-[6-3-fluoro-4-methoxyphenyl)-1,3-benzodioxol-5-yl] benzenesulfonamide;
4-[6-(3-chloro-4-methoxyphenyl)-1,3-benzodioxol-5-yl] benzenesulfonamide;
4-[6-(3,4-dimethoxyphenyl)-1,3-benzodioxol-5-yl] benzenesulfonamide;
4-[6-)4-methoxy-3-trifluoromethylphenyl)-1,3-benzodioxol-5-yl]benzenesulfonamide;
4-[6-[3-(N,N-dimethylamino)-4-methoxyphenyl]-1,3-benzodioxol-5-yl]benzenesulfonamide;
4-[6-(4-fluorophenyl)-1,3-benzodioxol-5-yl] benzenesulfonamide;
4-[6-(4-fluoro-3-methylphenyl)-1,3-benzodioxol-5-yl] benzenesulfonamide;
4-[6-(3,4-difluorophenyl)-1,3-benzodioxol-5-yl] benzenesulfonamide;
4-[6-(3-chloro-4-fluorophenyl)-1,3-benzodioxol-5-yl] benzenesulfonamide;
4-[6-(4-fluoro-3-methoxyphenyl)-1,3-benzodioxol-5-yl] benzenesulfonamide;
4-[6-(4-fluoro-3-trifluoromethylphenyl)-1,3-benzodioxol-5-yl]benzenesulfonamide
4-[6-[3-(N,N-dimethylamino)-4-fluorophenyl]-1,3-benzodioxol-5-yl]benzenesulfonamide;

4-[6-(4-chlorophenyl)-1,3-benzodioxol-5-yl]
benzenesulfonamide;
4-[6-(4-chloro-3-methylphenyl)-1,3-benzodioxol-5-yl]
benzenesulfonamide;
4-[6-(4-chloro-3-fluorophenyl)-1,3-benzodioxol-5-yl]
benzenesulfonamide;
4-[6-(3,4-dichlorophenyl)-1,3-benzodioxol-5-yl]
benzenesulfonamide;
4-[6-(4-chloro-3-methoxyphenyl)-1,3-benzodioxol-5-yl]
benzenesulfonamide;
4-[6-(4-chloro-3-trifluoromethylphenyl)-1,3-benzodioxol5-yl]benzenesulfonamide;
4-[6-[4-chloro-3-(N,N-dimethylamino)phenyl]-1,3-benzodioxol-5-yl]benzenesulfonamide;
4-[6-(4-trifluoromethylphenyl)-1,3-benzodioxol-5-yl]
benzenesulfonamide;
4-[6-(3-methyl-4-trifluoromethylphenyl)-1,3-benzodioxol-5-yl]benzenesulfonamide;
4-[6-(3-fluoro-4-trifluoromethylphenyl)-1,3-benzodioxol-5-yl]benzenesulfonamide;
4-[6-(3-chloro-4-trifluoromethylphenyl)-1,3-benzodioxol-5-yl]benzenesulfonamide;
4-[6-(3-methoxy-4-trifluoromethylphenyl)-1,3-benzodioxol-5-yl]benzenesulfonamide;
4-[6-[3,4-di(trifluoromethyl)phenyl]-1,3-benzodioxol-5-yl]
benzenesulfonamide;
4-[6-[3-(N,N-dimethylamino)-4-trifluoromethylphenyl]-1,3-benzodioxol-5-yl]benzenesulfonamide;
4-[6-[4-(N,N-dimethylamino)phenyl]-1,3-benzodioxol-5-yl]benzenesulfonamide;
4-[6-[4-(N,N-dimethylamino)-3-methylphenyl]-1,3-benzodioxol-5-yl]benzenesulfonamide;
4-[6-[4-(N,N-dimethylamino)-3-fluorophenyl]-1,3-benzodioxol-5-yl]benzenesulfonamide;
4-[6-[3-chloro-4-(N,N-dimethylamino)phenyl]-1,3-benzodioxol-5-yl]benzenesulfonamide;
4-[6-[4-(N,N-dimethylamino)-3-methoxyphenyl]-1,3-benzodioxol-5-yl]benzenesulfonamide;
4-[6-[4-(N,N-dimethylamino)-3-trifluoromethylphenyl]-1,3-benzodioxol-5-yl]benzenesulfonamide;
4-[6-[3,4-di((N,N-dimethylamino))phenyl]-1,3-benzodioxol-5-yl]benzenesulfonamide;
4-[6-(3,5-dimethylphenyl)-1,3-benzodioxol-5-yl]
benzenesulfonamide;
4-[6-(3,5-difluorophenyl)-1,3-benzodioxol-5-yl]
benzenesulfonamide;
4-[6-(3,5-dichlorophenyl)-1,3-benzodioxol-5-yl]
benzenesulfonamide;
4-[6-(3,5-dimethoxyphenyl)-1,3-benzodioxol-5-yl]
benzenesulfonamide;
4-[6-[3,5-di(trifluoromethyl)phenyl]-1,3-benzodioxol-5-yl]
benzenesulfonamide;
4-[6-[3,5-di(N,N-dimethylamino)phenyl]-1,3-benzodioxol-5-yl]benzenesulfonamide;
4-[6-(3,5-dimethyl-4-methylphenyl)-1,3-benzodioxol-5-yl]
benzenesulfonamide;
4-[6-(3,5-difluoro-4-methylphenyl)-1,3-benzodioxol-5-yl]
benzenesulfonamide;
4-[6-(3,5-dichloro-4-methylphenyl)-1,3-benzodioxol-5-yl]
benzenesulfonamide;
4-[6-(3,5-dimethoxy-4-methylphenyl)-1,3-benzodioxol-5-yl]benzenesulfonamide;
4-[6-[3,5-di(trifluoromethyl)-4-methylphenyl]-1,3-benzodioxol-5-yl]benzenesulfonamide;
4-[6-[3,5-di(N,N-dimethylamino)-4-methylphenyl]-1,3-benzodioxol-5-yl]benzenesulfonamide;
4-[6-(3,5-dimethyl-4-methoxyphenyl)-1,3-benzodioxol-5-yl]benzenesulfonamide;
4-[6-(3,5-difluoro-4-methoxyphenyl)-1,3-benzodioxol-5-yl]
benzenesulfonamide;
4-[6-(3,5-dichloro-4-methoxyphenyl)-1,3-benzodioxol-5-yl]benzenesulfonamide;
4-[6-(3,5-dimethoxy-4-methoxyphenyl)-1,3-benzodioxol-5-yl]benzenesulfonamide;
4-[6-[3,5-di(trifluoromethyl)-4-methoxyphenyl]-1,3-benzodioxol-5-yl]benzenesulfonamide;
4-[6-[3,5-di(N,N-dimethylamino)-4-methoxyphenyl]-1,3-benzodioxol-5-yl]benzenesulfonamide;
4-[6-(3,5-dimethyl-4-fluorophenyl)-1,3-benzodioxol-5-yl]
benzenesulfonamide;
4-[6-(3,5-difluoro-4-fluorophenyl)-1,3-benzodioxol-5-yl]
benzenesulfonamide;
4-[6-(3,5-dichloro-4-fluorophenyl)-1,3-benzodioxol-5-yl]
benzenesulfonamide;
4-[6-(3,5-dimethoxy-4-fluorophenyl)-1,3-benzodioxol-5-yl]
benzenesulfonamide;
4-[6-[3,5-di(trifluoromethyl)-4-fluorophenyl]-1,3-benzodioxol-5-yl]benzenesulfonamide;
4-[6-[3,5-di(N,N-dimethylamino)-4-fluorophenyl]-1,3-benzodioxol-5-yl]benzenesulfonamide;
4-[6-(4-chloro-3,5-dimethylphenyl)-1,3-benzodioxol-5-yl]
benzenesulfonamide;
4-[6-(4-chloro-3,5-difluorophenyl)-1,3-benzodioxol-5-yl]
benzenesulfonamide;
4-[6-(3,4,5-trichlorophenyl)-1,3-benzodioxol-5-yl]
benzenesulfonamide;
4-[6-(4-chloro-3,5-dimethoxyphenyl)-1,3-benzodioxol-5-yl]benzenesulfonamide;
4-[6-[4-chloro-3,5-di(trifluoromethyl)phenyl]-1,3-benzodioxol-5-yl]benzenesulfonamide;
4-[6-[4-chloro-3,5-di(N,N-dimethylamino)phenyl]-1,3-benzodioxol-5-yl]benzenesulfonamide;
4-[6-(3,5-dimethyl-4-trifluoromethylphenyl)-1,3-benzodioxol-5-yl]benzenesulfonamide;
4-[6-(3,5-difluoro-4-trifluoromethylphenyl)-1,3-benzodioxol-5-yl]benzenesulfonamide;
4-[6-(3,5-dichloro-4-trifluoromethylphenyl)-1,3-benzodioxol-5-yl]benzenesulfonamide;
4-[6-(3,5-dimethoxy-4-trifluoromethylphenyl)-1,3-benzodioxol-5-yl]benzenesulfonamide;
4-[6-[3,4,5-tri(trifluoromethyl)phenyl]-1,3-benzodioxol-5-yl]benzenesulfonamide;
4-[6-[3,5-di(N,N-dimethylamino)-4-trifluoromethylphenyl]
1,3-benzodioxol-5-yl]benzenesulfonamide;
4-[6-[3,5-dimethyl-4-(N,N-dimethylamino)phenyl]-1,3-benzodioxol-5-yl]benzenesulfonamide;
4-[6-[4-(N,N-dimethylamino)-3,5-difluorophenyl]-1,3-benzodioxol-5-yl]benzenesulfonamide;
4-[6-[3,5-dichloro-4-(N,N-dimethylamino)phenyl]-1,3-benzodioxol-5-yl]benzenesulfonamide;
4-[6-[3,5-dimethoxy-4-(N,N-dimethylamino)phenyl]-1,3-benzodioxol-5-yl]benzenesulfonamide;
4-[6-[4-(N,N-dimethylamino)-3,5-di(trifluoromethyl)
phenyl]-1,3-benzodioxol-5-yl]benzenesulfonamide;
4-[6-[3,4,5-tri(N,N-dimethylamino)phenyl]-1,3-benzodioxol-5-yl]benzenesulfonamide;
4-[4,5-difluoro-2-biphenyl]benzenesulfonamide;
4-[4,5-difluoro-2-(3-methylphenyl)phenyl]
benzenesulfonamide;
4-[4,5-difluoro-2-(3-fluorophenyl)phenyl]
benzenesulfonamide;
4-[2-(3-chlorophenyl)-4,5-difluorophenyl]
benzenesulfonamide;
4-[4,5-difluoro-2-(3-methoxyphenyl)phenyl]
benzenesulfonamide;

4-[4,5-difluoro-2-(3-trifluoromethylphenyl)phenyl]
benzenesulfonamide;
4-[4,5-difluoro-2-[3-(N,N-dimethylamino)phenyl]phenyl]
benzenesulfonamide;
4-[4,5-difluoro-2-(4-methylphenyl)phenyl]
benzenesulfonamide;
4-[4,5-difluoro-2-(3,4-dimethylphenyl)phenyl]
benzenesulfonamide;
4-[4,5-difluoro-2-(3-fluoro-4-methylphenyl)phenyl]
benzenesulfonamide;
4-[2-(3-chloro-4-methylphenyl)-4,5-difluorophenyl]
benzenesulfonamide;
4-[4,5-difluoro-2-(3-methoxy-4-methylphenyl)phenyl]
benzenesulfonamide;
4-[4,5-difluoro-2-(4-methyl-3-trifluoromethylphenyl)
phenyl]benzenesulfonamide;
4-[4,5-difluoro-2-[3-(N,N-dimethylamino)-4-
methylphenyl]phenyl]benzenesulfonamide;
4-[4,5-difluoro-2-(4-methoxyphenyl)phenyl]
benzenesulfonamide;
4-[4,5-difluoro-2-(4-methoxy-3-methylphenyl)phenyl]
benzenesulfonamide;
4-[4,5-difluoro-2-(3-fluoro-4-methoxyphenyl)phenyl]
benzenesulfonamide;
4-[2-(3-chloro-4-methoxyphenyl)-4,5-difluorophenyl]
benzenesulfonamide;
4-[4,5-difluoro-2-(3,4-dimethoxyphenyl)phenyl]
benzenesulfonamide;
4-[4,5-difluoro-2-(4-methoxy-3-trifluoromethylphenyl)
phenyl]benzenesulfonamide;
4-[4,5-difluoro-2-[3-(N,N-dimethylamino)-methoxyphenyl]
phenyl]benzenesulfonamide;
4-[4,5-difluoro-2-(4-fluorophenyl)phenyl]
benzenesulfonamide;
4-[4,5-difluoro-2-(4-fluoro-3-methylphenyl)phenyl]
benzenesulfonamide;
4-[4,5-difluoro-2-(3,4-difluorophenyl)phenyl]
benzenesulfonamide;
4-[4,5-difluoro-2-(3-chloro-4-fluorophenyl)phenyl]
benzenesulfonamide;
4-[4,5-difluoro-2-(4-fluoro-3-methoxyphenyl)phenyl]
benzenesulfonamide;
4-[4,5-difluoro-2-(4-fluoro-3-trifluoromethylphenyl)
phenyl]benzenesulfonamide;
4-[4,5-difluoro-2-[3-(N,N-dimethylamino)-4-fluorophenyl]
phenyl]benzenesulfonamide;
4-[2-(4-chlorophenyl)-4,5-difluorophenyl]
benzenesulfonamide;
4-[2-(4-chloro-3-methylphenyl)-4,5-difluorophenyl]
benzenesulfonamide;
4-[2-(4-chloro-3-fluorophenyl)-4,5-difluorophenyl]
benzenesulfonamide;
4-[2-(3,4-dichlorophenyl)-4,5-difluorophenyl]
benzenesulfonamide;
4-[2-(4-chloro-3-methoxyphenyl)-4,5-difluorophenyl]
benzenesulfonamide;
4-[2-(4-chloro-3-trifluoromethylphenyl)-4,5-
difluorophenyl]benzenesulfonamide;
4-[2-[4-chloro-3-(N,N-dimethylamino)phenyl]-4,5-
difluorophenyl]benzenesulfonamide;
4-[4,5-difluoro-2-(4-trifluoromethylphenyl)phenyl]
benzenesulfonamide;
4-[4,5-difluoro-2-(3-methyl-4-trifluoromethylphenyl)
phenyl]benzenesulfonamide;
4-[4,5-difluoro-2-(3-fluoro-4-trifluoromethylphenyl)
phenyl]benzenesulfonamide;
4-[2-(3-chloro-4-trifluoromethylphenyl)-4,5-
difluorophenyl]benzenesulfonamide;

4-[4,5-difluoro-2-(3-methoxy-4-trifluoromethylphenyl)
phenyl]benzenesulfonamide;
4-[4,5-difluoro-2-[3,4-di(trifluoromethyl)phenyl]phenyl]
benzenesulfonamide;
4-[4,5-difluoro-2-[3-(N,N-dimethylamino)-4-
trifluoromethylphenyl]phenyl]benzenesulfonamide;
4-[4,5-difluoro-2-[4-(N,N-dimethylamino)phenyl]phenyl]
benzenesulfonamide;
4-[4,5-difluoro-2-[4-(N,N-dimethylamino)-3-
methylphenyl]phenyl]benzenesulfonamide;
4-[4,5-difluoro-2-[4-(N,N-dimethylamino)-3-fluorophenyl]
phenyl]benzenesulfonamide;
4-[2-[3-chloro-4-(N,N-dimethylamino)phenyl]-4-
difluorophenyl]benzenesulfonamide;
4-[4,5-difluoro-2-[4-(N,N-dimethylamino)-3-
methoxyphenyl]phenyl]benzenesulfonamide;
4-[4,5-difluoro-2-[4-(N,N-dimethylamino)-3-
trifluoromethylphenyl]phenyl]benzenesulfonamide;
4-[4,5-difluoro-2-[3,4-di(N,N-dimethylamino)phenyl]
phenyl]benzenesulfonamide
4-[4,5-difluoro-2-(3,5-dimethylphenyl)phenyl]
benzenesulfonamide;
4-[4,5-difluoro-2-(3,5-difluorophenyl)phenyl]
benzenesulfonamide;
4-[2-(3,5-dichlorophenyl)-4,5-difluorophenyl]
benzenesulfonamide;
4-[4,5-difluoro-2-(3,5-dimethoxyphenyl)phenyl]
benzenesulfonamide;
4-[4,5-difluoro-2-[3,5-di(trifluoromethyl)phenyl]phenyl]
benzenesulfonamide;
4-[4,5-difluoro-2-[3,5-di(N,N-dimethylamino)phenyl]
phenyl]benzenesulfonamide;
4-[4,5-difluoro-2-(3,4,5-trimethylphenyl)phenyl]
benzenesulfonamide;
4-[4,5-difluoro-2-(3,5-difluoro-4-methylphenyl)phenyl]
benzenesulfonamide;
4-[2-(3,5-dichloro-4-methylphenyl)-4,5-difluorophenyl]
benzenesulfonamide;
4-[4,5-difluoro-2-(3,5-dimethoxy-4-methylphenyl)phenyl]
benzenesulfonamide;
4-[4,5-difluoro-2-[3,5-di(trifluoromethyl)-4-methylphenyl]
phenyl]benzenesulfonamide;
4-[4,5-difluoro-2-[3,5-di(N,N-dimethylamino)-4-
methylphenyl]phenyl]benzenesulfonamide;
4-[4,5-difluoro-2-(3,5-dimethyl-4-methoxyphenyl)phenyl]
benzenesulfonamide;
4-[4,5-difluoro-2-(3,5-difluoro-4-methoxyphenyl)phenyl]
benzenesulfonamide;
4-[2-(3,5-dichloro-4-methoxyphenyl)-4,5-difluorophenyl]
benzenesulfonamide;
4-[4,5-difluoro-2-(3,4,5-trimethoxyphenyl)phenyl]
benzenesulfonamide;
4-[4,5-difluoro-2-[3,5-di(trifluoromethyl)-4-
methoxyphenyl]phenyl]benzenesulfonamide;
4-[4,5-difluoro-2-[3,5-di(N,N-dimethylamino)-4-
methoxyphenyl]phenyl]benzenesulfonamide;
4-[4,5-difluoro-2-(3,5-dimethyl-4-fluorophenyl)phenyl]
benzenesulfonamide;
4-[4,5-difluoro-2-(3,4,5-difluorophenyl)phenyl]
benzenesulfonamide;
4-[2-(3,5-dichloro-4-fluorophenyl)-4,5-difluorophenyl]
benzenesulfonamide;
4-[4,5-difluoro-2-(3,5-dimethoxy-4-fluorophenyl)phenyl]
benzenesulfonamide;
4-[4,5-difluoro-2-[3,5-di(trifluoromethyl)-4-fluorophenyl]
phenyl]benzenesulfonamide;
4-[4,5-difluoro-2-[3,5-di(N,N-dimethylamino)-4-
fluorophenyl]phenyl]benzenesulfonamide;

4-[2-(4-chloro-3,5-dimethylphenyl)-4,5-difluorophenyl] benzenesulfonamide;
4-[2-(4-chloro-3,5-difluorophenyl)-4,5-difluorophenyl] benzenesulfonamide;
4-[4,5-difluoro-2-(3,4,5-trichlorophenyl)phenyl] benzenesulfonamide;
4-[2-(4-chloro-3,5-dimethoxyphenyl)-4,5-difluorophenyl] benzenesulfonamide;
4-[2-[4-chloro-3,5-di(trifluoromethyl)phenyl]-4,5-difluorophenyl]benzenesulfonamide;
4-[2-[4-chloro-3,5-di(N,N-dimethylamino)phenyl]-4,5-difluorophenyl]benzenesulfonamide;
4-[4,5-difluoro-2-(3,5-dimethyl-4-trifluoromethylphenyl) phenyl]benzenesulfonamide;
4-[4,5-difluoro-2-(3,5-difluoro-4-trifluoromethylphenyl) phenyl]benzenesulfonamide;
4-[2-(3,5-dichloro-4-trifluoromethylphenyl)-4,5-difluorophenyl]benzenesulfonamide;
4-[4,5-difluoro-2-(3,5-dimethoxy-4-trifluoromethylphenyl) phenyl]benzenesulfonamide;
4-[4,5-difluoro-2-[3,4,5-tri(trifluoromethyl)phenyl]phenyl] benzenesulfonamide;
4-[4,5-difluoro-2-[3,5-di(N,N-dimethylamino)-4-trifluoromethylphenyl]phenyl]benzenesulfonamide;
4-[4,5-difluoro-2-[3,5-dimethyl-4-(N,N-dimethylamino) phenyl]phenyl]benzenesulfonamide;
4-[4,5-difluoro-2-[3,5-difluoro-4-(N,N-dimethylamino) phenyl]phenyl]benzenesulfonamide;
4-[2-[3,5-dichloro-4-(N,N-dimethylamino)phenyl]-4,5-difluorophenyl]benzenesulfonamide;
4-[4,5-difluoro-2-[3,5-dimethoxy-4-(N,N-dimethylamino) phenyl]phenyl]benzenesulfonamide;
4-[4,5-difluoro-2-[3,5-di(trifluoromethyl)-4-(N,N-dimethylamino)phenyl]phenyl]benzenesulfonamide;
4-[4,5-difluoro-2-[3,4,5-tri((N,N-dimethylamino)phenyl] phenyl]benzenesulfonamide;
4-[3,4,5,6-tetrafluoro-2-biphenyl]benzenesulfonamide;
4-[2-(3-methylphenyl)-3,4,5,6-tetrafluorophenyl] benzenesulfonamide;
4-[2-(3-fluorophenyl)-3,4,5,6-tetrafluorophenyl] benzenesulfonamide;
4-[2-(3-chlorophenyl)-3,4,5,6-tetrafluorophenyl] benzenesulfonamide;
4-[2-(3-methoxyphenyl)-3,4,5,6-tetrafluorophenyl] benzenesulfonamide;
4-[3,4,5,6-tetrafluoro-2-(3-trifluoromethylphenyl)phenyl] benzenesulfonamide;
4-[2-[3-(N,N-dimethylamino)phenyl]-3,4,5,6-tetrafluorophenyl]benzenesulfonamide;
4-[2-(4-methylphenyl)-3,4,5,6-tetrafluorophenyl] benzenesulfonamide;
4-[2-(3,4-dimethylphenyl)-3,4,5,6-tetrafluorophenyl] benzenesulfonamide;
4-[2-(3-fluoro-4-methylphenyl)-3,4,5,6-tetrafluorophenyl] benzenesulfonamide;
4-[2-(3-chloro-4-methylphenyl)-3,4,5,6-tetrafluorophenyl] benzenesulfonamide;
4-[2-(3-methoxy-4-methylphenyl)-3,4,5,6-tetrafluorophenyl]benzenesulfonamide;
4-[2-(4-methyl-3-trifluoromethylphenyl)-3,4,5,6-tetrafluorophenyl]benzenesulfonamide;
4-[2-[3-(N,N-dimethylamino)-4-methylphenyl]-3,4,5,6-tetrafluorophenyl]benzenesulfonamide;
4-[2-(4-methoxyphenyl)-3,4,5,6-tetrafluorophenyl] benzenesulfonamide;
4-[2-(3-methyl-4-methoxyphenyl)-3,4,5,6-tetrafluorophenyl]benzenesulfonamide;
4-[2-(3-fluoro-4-methoxyphenyl)-3,4,5,6-tetrafluorophenyl]benzenesulfonamide;
4-[2-(3-chloro-4-methoxyphenyl)-3,4,5,6-tetrafluorophenyl]benzenesulfonamide;
4-[2-(3,4-dimethoxyphenyl)-3,4,5,6-tetrafluorophenyl] benzenesulfonamide;
4-[2-(4-methoxy-3-trifluoromethylphenyl)-3,4,5,6-tetrafluorophenyl]benzenesulfonamide;
4-[2-[3-(N,N-dimethylamino)-4-methoxyphenyl]-3,4,5,6-tetrafluorophenyl]benzenesulfonamide;
4-[2-(4-fluorophenyl)-3,4,5,6-tetrafluorophenyl] benzenesulfonamide;
4-[2-(4-fluoro-3-methylphenyl)-3,4,5,6-tetrafluorophenyl] benzenesulfonamide;
4-[2-(3,4-difluorophenyl)-3,4,5,6-tetrafluorophenyl] benzenesulfonamide;
4-[2-(3-chloro-4-fluorophenyl)-3,4,5,6-tetrafluorophenyl] benzenesulfonamide;
4-[2-(4-fluoro-3-methoxyphenyl)-3,4,5,6-tetrafluorophenyl]benzenesulfonamide;
4-[2-(4-fluoro-3-trifluoromethylphenyl)-3,4,5,6-tetrafluorophenyl]benzenesulfonamide;
4-[2-[3-(N,N-dimethylamino)-4-fluorophenyl]-3,4,5,6-tetrafluorophenyl]benzenesulfonamide;
4-[2-(4-chlorophenyl)-3,4,5,6-tetrafluorophenyl] benzenesulfonamide;
4-[2-(4-chloro-3-methylphenyl)-3,4,5,6-tetrafluorophenyl] benzenesulfonamide;
4-[2-(4-chloro-3-fluorophenyl)-3,4,5,6-tetrafluorophenyl] benzenesulfonamide;
4-[2-(3,4-dichlorophenyl)-3,4,5,6-tetrafluorophenyl] benzenesulfonamide;
4-[2-(4-chloro-3-methoxyphenyl)-3,4,5,6-tetrafluorophenyl]benzenesulfonamide;
4-[2-(4-chloro-3-trifluoromethylphenyl)-3,4,5,6-tetrafluorophenyl]benzenesulfonamide;
4-[2-[4-chloro-3-(N,N-dimethylamino)phenyl]-3,4,5,6-tetrafluorophenyl]benzenesulfonamide;
4-[3,4,5,6-tetrafluoro-2-(4-trifluoromethylphenyl)phenyl] benzenesulfonamide;
4-[2-(3-methyl-4-trifluoromethylphenyl)-3,4,5,6-tetrafluorophenyl]benzenesulfonamide;
4-[2-(3-fluoro-4-trifluoromethylphenyl)-3,4,5,6-tetrafluorophenyl]benzenesulfonamide;
4-[2-(3-chloro-4-trifluoromethylphenyl)-3,4,5,6-tetrafluorophenyl]benzenesulfonamide;
4-[2-(3-methoxy-4-trifluoromethylphenyl)-3,4,5,6-tetrafluorophenyl]benzenesulfonamide;
4-[2-[3,4-di(trifluoromethyl)phenyl]-3,4,5,6-tetrafluorophenyl]benzenesulfonamide;
4-[2-[3-(N,N-dimethylamino)-4-trifluoromethylphenyl]-3,4,5,6-tetrafluorophenyl]benzenesulfonamide;
4-[2-[4-(N,N-dimethylamino)phenyl]-3,4,5,6-tetrafluorophenyl]benzenesulfonamide;
4-[2-[4-(N,N-dimethylamino)-3-methylphenyl]-3,4,5,6-tetrafluorophenyl]benzenesulfonamide;
4-[2-[4-(N,N-dimethylamino)-3-fluorophenyl]-3,4,5,6-tetrafluorophenyl]benzenesulfonamide;
4-[2-[3-chloro-4-(N,N-dimethylamino)phenyl]-3,4,5,6-tetrafluorophenyl]benzenesulfonamide;
4-[2-[4-N,N-dimethylamino)-3-methoxyphenyl]-3,4,5,6-tetrafluorophenyl]benzenesulfonamide;
4-[2-[4-(N,N-dimethylamino)-3-trifluoromethylphenyl]-3,4,5,6-tetrafluorophenyl]benzenesulfonamide;
4-[2-[3,4-di(N,N-dimethylamino)phenyl]-3,4,5,6-tetrafluorophenyl]benzenesulfonamide;
4-[2-(3,5-dimethylphenyl)-3,4,5,6-tetrafluorophenyl] benzenesulfonamide;

4-[2-(3,5-difluorophenyl)-3,4,5,6-tetrafluorophenyl]benzenesulfonamide;
4-[2-(3,5-dichlorophenyl)-3,4,5,6-tetrafluorophenyl]benzenesulfonamide;
4-[2-(3,5-dimethoxyphenyl)-3,4,5,6-tetrafluorophenyl]benzenesulfonamide;
4-[2-[3,5-di(trifluoromethyl)phenyl]-3,4,5,6-tetrafluorophenyl]benzenesulfonamide;
4-[2-[3,5-di(N,N-dimethylamino)phenyl]-3,4,5,6-tetrafluorophenyl]benzenesulfonamide;
4-[2-(3,4,5-trimethylphenyl)-3,4,5,6-tetrafluorophenyl]benzenesulfonamide;
4-[2-(3,5-difluoro-4-methylphenyl)-3,4,5,6-tetrafluorophenyl]benzenesulfonamide;
4-[2-(3,5-dichloro-4-methylphenyl)-3,4,5,6-tetrafluorophenyl]benzenesulfonamide;
4-[2-(3,5-dimethoxy-4-methylphenyl)-3,4,5,6-tetrafluorophenyl]benzenesulfonamide;
4-[2-[3,5-di(trifluoromethyl)-4-methylphenyl]-3,4,5,6-tetrafluorophenyl]benzenesulfonamide;
4-[2-[3,5-di(N,N-dimethylamino)-4-methylphenyl]-3,4,5,6-tetrafluorophenyl]benzenesulfonamide;
4-[2-(3,5-dimethyl-4-methoxyphenyl)-3,4,5,6-tetrafluorophenyl]benzenesulfonamide;
4-[2-(3,5-difluoro-4-methoxyphenyl)-3,4,5,6-tetrafluorophenyl]benzenesulfonamide;
4-[2-(3,5-dichloro-4-methoxyphenyl)-3,4,5,6-tetrafluorophenyl]benzenesulfonamide;
4-[2-(3,4,5-trimethoxyphenyl)-3,4,5,6-tetrafluorophenyl]benzenesulfonamide;
4-[2-[3,5-di(trifluoromethyl)-4-methoxyphenyl]-3,4,5,6-tetrafluorophenyl]benzenesulfonamide;
4-[2-[3,5-di(N,N-dimethylamino]-4-methoxyphenyl]-3,4,5,6-tetrafluorophenyl]benzenesulfonamide;
4-[2-(3,5-dimethyl-4-fluorophenyl)-3,4,5,6-tetrafluorophenyl]benzenesulfonamide;
4-[2-(3,4,5-trifluorophenyl)-3,4,5,6-tetrafluorophenyl]benzenesulfonamide;
4-[2-(3,5-dichloro-4-fluorophenyl)-3,4,5,6-tetrafluorophenyl]benzenesulfonamide;
4-[2-(3,5-dimethoxy-4-fluorophenyl)-3,4,5,6-tetrafluorophenyl]benzenesulfonamide;
4-[2-[3,5-di(trifluoromethyl)-4-fluorophenyl]-3,4,5,6-tetrafluorophenyl]benzenesulfonamide;
4-[2-[3,5-di(N,N-dimethylamino)-4-fluorophenyl]-3,4,5,6-tetrafluorophenyl]benzenesulfonamide;
4-[2-(4-chloro-3,5-dimethylphenyl)-3,4,5,6-tetrafluorophenyl]benzenesulfonamide;
4-[2-(4-chloro-3,5-difluorophenyl)-3,4,5,6-tetrafluorophenyl]benzenesulfonamide;
4-[3,4,5,6-tetrafluoro-2-(3,4,5-trichloro-4-chlorophenyl)phenyl]benzenesulfonamide;
4-[2-(4-chloro-3,5-dimethoxyphenyl)-3,4,5,6-tetrafluorophenyl]benzenesulfonamide;
4-[2-[4-chloro-3,5-di(trifluoromethyl)phenyl]-3,4,5,6-tetrafluorophenyl]benzenesulfonamide;
4-[2-[4-chloro-3,5-di(N,N-dimethylamino)phenyl]-3,4,5,6-tetrafluorophenyl]benzenesulfonamide;
4-[2-(3,5-dimethyl-4-trifluoromethylphenyl)-3,4,5,6-tetrafluorophenyl]benzenesulfonamide;
4-[2-(3,5-difluoro-4-trifluoromethylphenyl)-3,4,5,6-tetrafluorophenyl]benzenesulfonamide;
4-[2-(3,5-dichloro-4-trifluoromethylphenyl)-3,4,5,6-tetrafluorophenyl]benzenesulfonamide;
4-[2-(3,5-dimethoxy-4-trifluoromethylphenyl)-3,4,5,6-tetrafluorophenyl]benzenesulfonamide;
4-[2-[3,4,5-tri(trifluoromethyl)phenyl]-3,4,5,6-tetrafluorophenyl]benzenesulfonamide;
4-[2-[3,5-di(N,N-dimethylamino)-4-trifluoromethylphenyl]-3,4,5,6-tetrafluorophenyl]benzenesulfonamide;
4-[2-[3,5-dimethyl-4-(N,N-dimethylamino)phenyl]-3,4,5,6-tetrafluorophenyl]benzenesulfonamide;
4-[2-[3,5-difluoro-4-(N,N-dimethylamino)phenyl]-3,4,5,6-tetrafluorophenyl]benzenesulfonamide;
4-[2-[3,5-dichloro-4-(N,N-dimethylamino)phenyl]-3,4,5,6-tetrafluorophenyl]benzenesulfonamide;
4-[2-[3,5-dimethoxy-4-(N,N-dimethylamino)phenyl]-3,4,5,6-tetrafluorophenyl]benzenesulfonamide;
4-[2-[3,5-di(trifluoromethyl)-4-(N,N-dimethylamino)phenyl]-3,4,5,6-tetrafluorophenyl]benzenesulfonamide;
4-[2-[3,4,5-tri(dimethylamino)phenyl]-3,4,5,6-tetrafluorophenyl]benzenesulfonamide;
4-[2-(4-hydroxymethylphenyl)phenyl]benzenesulfonamide;
4-[2-(4-methylthiophenyl)phenyl]benzenesulfonamide;
4-[2-(4-cyanophenyl)phenyl]benzenesulfonamide;
4-[2-(4-aminophenyl)phenyl]benzenesulfonamide;
4-[2-(4-hydroxyphenyl)phenyl]benzenesulfonamide;
4-[2-[4-(N-methylamino)phenyl]phenyl]benzenesulfonamide; and
4-[2-(4-methoxymethylphenyl)phenyl]benzenesulfonamide.

A second family of specific compounds of particular interest within Formula I consists of compounds and pharmaceutically-acceptable salts thereof as follows:
2-[4-(methylsulfonyl)phenyl]-1-phenylbenzene;
1-(3-methylphenyl)-2-[4-(methylsulfonyl)phenyl]benzene;
1-(3-methoxyphenyl)-2-[4-(methylsulfonyl)phenyl]benzene;
1-(3-fluorophenyl)-2-[4-(methylsulfonyl)phenyl]benzene;
1-(3-chlorophenyl)-2-[4-(methylsulfonyl)phenyl]benzene;
1-(4-methylphenyl)-2-[4-(methylsulfonyl)phenyl]benzene;
1-(3,4-dimethylphenyl)-2-[4-(methylsulfonyl)phenyl]benzene;
1-(3-methoxy-4-methylphenyl)-2-[4-(methylsulfonyl)phenyl]benzene;
1-(3-fluoro-4-methylphenyl)-2-[4-(methylsulfonyl)phenyl]benzene;
1-(3-chloro-4-methylphenyl)-2-[4-(methylsulfonyl)phenyl]benzene;
1-(4-methoxyphenyl)-2-[4-(methylsulfonyl)phenyl]benzene;
1-(3-methyl-4-methoxyphenyl)-2-[4-(methylsulfonyl)phenyl]benzene;
1-(3,4-dimethoxyphenyl)-2-[4-(methylsulfonyl)phenyl]benzene;
1-(3-fluoro-4-methoxyphenyl)-2-[4-(methylsulfonyl)phenyl]benzene;
1-(3-chloro-4-methoxyphenyl)-2-[4-(methylsulfonyl)phenyl]benzene;
1-(4-fluorophenyl)-2-[4-(methylsulfonyl)phenyl]benzene;
1-(4-fluoro-3-methylphenyl)-2-[4-(methylsulfonyl)phenyl]benzene;
1-(4-fluoro-3-methoxyphenyl)-2-[4-(methylsulfonyl)phenyl]benzene;
1-(3,4-difluorophenyl)-2-[4-(methylsulfonyl)phenyl]benzene;
1-(3-chloro-4-fluorophenyl)-2-[4-(methylsulfonyl)phenyl]benzene;
1-(4-chlorophenyl)-2-[4-(methylsulfonyl)phenyl]benzene;
1-(4-chloro-3-methylphenyl)-2-[4-(methylsulfonyl)phenyl]benzene;
1-(4-chloro-3-methoxyphenyl)-2-[4-(methylsulfonyl)phenyl]benzene;
1-(4-chloro-3-fluorophenyl)-2-[4-(methylsulfonyl)phenyl]benzene;

1-(3,4-dichlorophenyl)-2-[4-(methylsulfonyl)phenyl]
benzene;
1-(3,5-dimethylphenyl)-2-[4-(methylsulfonyl)phenyl]
benzene;
1-(3,5-dimethoxyphenyl)-2-[4-(methylsulfonyl)phenyl]
benzene;
1-(3,5-difluorophenyl)-2-[4-(methylsulfonyl)phenyl]
benzene;
1-(3,5-dichlorophenyl)-2-[4-(methylsulfonyl)phenyl]
benzene;
1-(3,4,5-trimethylphenyl)-2-[4-(methylsulfonyl)phenyl]
benzene;
1-(3,5-dimethoxy-4-methylphenyl)-2-[4-(methylsulfonyl)
phenyl]benzene;
1-(3,5-difluoro-4-methylphenyl)-2-[4-(methylsulfonyl)
phenyl]benzene;
1-(3,5-dichloro-4-methylphenyl)-2-[4-(methylsulfonyl)
phenyl]benzene;
1-(3,5-dimethyl-4-methoxyphenyl)-2-[4-(methylsulfonyl)
phenyl]benzene;
1-(3 4,5-trimethoxyphenyl)-2-[4-(methylsulfonyl)phenyl]
benzene;
1-(3,5-difluoro-4-methoxyphenyl)-2-[4-(methylsulfonyl)
phenyl]benzene;
1-(3,5-dichloro-4-methoxyphenyl)-2-[4-(methylsulfonyl)
phenyl]benzene;
1-(3,5-dimethyl-4-fluorophenyl)-2-[4-(methylsulfonyl)
phenyl]benzene;
1-(3,5-dimethoxy-4-fluorophenyl)-2-[4-(methylsulfonyl)
phenyl]benzene;
1-(3,4,5-trifluorophenyl)-2-[4-(methylsulfonyl)phenyl]
benzene;
1-(3,5-dichloro-4-fluorophenyl)-2-[4-(methylsulfonyl)
phenyl]benzene;
1-(4-chloro-3,5-dimethylphenyl)-2-[4-(methylsulfonyl)
phenyl]benzene;
1-(4-chloro-3,5-dimethoxyphenyl)-2-[4-(methylsulfonyl)
phenyl]benzene;
1-(4-chloro-3,5-difluorophenyl)-2-[4-(methylsulfonyl)
phenyl]benzene;
1-3,4,5-trichlorophenyl)-2-[4-(methylsulfonyl)phenyl]
benzene;
6-[4-(methylsulfonyl)phenyl]-1-phenyl-1,3-benzodioxole;
1-(3-methylphenyl)-6-[4-(methylsulfonyl)phenyl]-1,3-benzodioxole;
1-(3-fluorophenyl)-6-[4-(methylsulfonyl)phenyl]-1,3-benzodioxole;
1-(3-chlorophenyl)-6-[4-(methylsulfonyl)phenyl]-1,3-benzodioxole;
1-(3-methoxyphenyl)-6-[4-(methylsulfonyl)phenyl]-1,3-benzodioxole;
1-(4-methylphenyl)-6-[4-(methylsulfonyl)phenyl]-1,3-benzodioxole;
1-(3,4-dimethylphenyl)-6-[4-(methylsulfonyl)phenyl]-1,3-benzodioxole;
1-(3-fluoro-4-methylphenyl)-6-[4-(methylsulfonyl)phenyl]-1,3-benzodioxole;
1-(3-chloro-4-methylphenyl)-6-[4-(methylsulfonyl)phenyl]-1,3-benzodioxole;
1-(3-methoxy-4-methylphenyl)-6-[4-(methylsulfonyl)
phenyl]-1,3-benzodioxole;
1-(4-methoxyphenyl)-6-[4-(methylsulfonyl)phenyl]-1,3-benzodioxole;
1-(3-methyl-4-methoxyphenyl)-6-[4-(methylsulfonyl)
phenyl]-1,3-benzodioxole;
1-(3-fluoro-4-methoxyphenyl)-6-[4-(methylsulfonyl)
phenyl]-1,3-benzodioxole;
1-(3-chloro-4-methoxyphenyl)-6-[4-(methylsulfonyl)
phenyl]-1,3-benzodioxole;
1-(3,4-dimethoxyphenyl)-6-[4-(methylsulfonyl)phenyl]-1,3-benzodioxole;
1-(4-fluorophenyl)-6-[4-(methylsulfonyl)phenyl]-1,3-benzodioxole;
1-(4-fluoro-3-methylphenyl)-6-[4-(methylsulfonyl)phenyl]-1,3-benzodioxole;
1-(3,4-difluorophenyl)-6-[4-(methylsulfonyl)phenyl]-1,3-benzodioxole;
1-(3-chloro-4-fluorophenyl)-6-[4-(methylsulfonyl)phenyl]-1,3-benzodioxole;
1-(4-fluoro-3-methoxyphenyl)-6-[4-(methylsulfonyl)
phenyl]-1,3-benzodioxole;
1-4-chlorophenyl)-6-[4-(methylsulfonyl)Phenyl]-1,3-benzodioxole;
1-4-chloro-3-methylphenyl)-6-[4-(methylsulfonyl)phenyl]-1,3-benzodioxole;
1-4-chloro-3-fluorophenyl)-6-[4-(methylsulfonyl)phenyl]-1,3-benzodioxole;
1-(3,4-dichlorophenyl)-6-[4-(methylsulfonyl)phenyl]-1,3-benzodioxole;
1-(4-chloro-3-methoxyphenyl)-6-[4-(methylsulfonyl)
phenyl]-1,3-benzodioxole;
1-(3,5-dimethylphenyl)-6-[4-(methylsulfonyl)phenyl]-1,3-benzodioxole;
1-(3,5-difluorophenyl)-6-[4-(methylsulfonyl)phenyl]-1,3-benzodioxole;
1-(3,5-dichlorophenyl)-6-[4-(methylsulfonyl)phenyl]-1,3-benzodioxole;
1-(3,5-dimethoxyphenyl)-6-[4-(methylsulfonyl)phenyl]-1,3-benzodioxole;
1-(3 4,5-trimethylphenyl)-6-[4-(methylsulfonyl)phenyl]-1,3-benzodioxole;
1-(3,5-difluoro-4-methylphenyl)-6-[4-(methylsulfonyl)
phenyl]-1,3-benzodioxole;
1-(3,5-dichloro-4-methylphenyl)-6-[4-(methylsulfonyl)
phenyl]-1,3-benzodioxole;
1-(3,5-dimethoxy-4-methylphenyl)-6-[4-(methylsulfonyl)
phenyl]-1,3-benzodioxole;
1-(3,5-dimethyl-4-methoxyphenyl)-6-[4-(methylsulfonyl)
phenyl]-1,3-benzodioxole;
1-(3,5-difluoro-4-methoxyphenyl)-6-[4-(methylsulfonyl)
phenyl]-1,3-benzodioxole;
1-(3,5-dichloro-4-methoxyphenyl)-6-[4-(methylsulfonyl)
phenyl]-1,3-benzodioxole;
1-(3 4,5-trimethoxyphenyl)-6-[4-(methylsulfonyl)phenyl]-1,3-benzodioxole;
1-(3,5-dimethyl-4-fluorophenyl)-6-[4-(methylsulfonyl)
phenyl]-1,3-benzodioxole;
1-(3,4,5-trifluorophenyl)-6-[4-(methylsulfonyl)phenyl]-1,3-benzodioxole;
1-(3,5-dichloro-4-fluorophenyl)-6-[4-(methylsulfonyl)
phenyl]-1,3-benzodioxole;
1-(3,5-dimethoxy-4-fluorophenyl)-6-[4-(methylsulfonyl)
phenyl]-1,3-benzodioxole;
1-(4-chloro-3,5-dimethylphenyl)-6-[4-(methylsulfonyl)
phenyl]-1,3-benzodioxole;
1-(4-chloro-3,5-difluorophenyl)-6-[4-(methylsulfonyl)
phenyl]-1,3-benzodioxole;
1-(3,4,5-trichlorophenyl)-6-[4-(methylsulfonyl)phenyl]-1,3-benzodioxole;
1-(4-chloro-3,5-dimethoxyphenyl)-6-[4-(methylsulfonyl)
phenyl]-1,3-benzodioxole;
1,2-difluoro-5-[4-(methylsulfonyl)phenyl]-4-phenylbenzene;
1,2-difluoro-4-(3-methylphenyl)-5-[4-(methylsulfonyl)
phenyl]benzene;

1,2-difluoro-4-(3-fluorophenyl)-5-[4-(methylsulfonyl)phenyl]benzene;
4-(3-chlorophenyl)-1,2-difluoro-5-[4-(methylsulfonyl)phenyl]benzene;
1,2-difluoro-4-(3-methoxyphenyl)-5-[4-(methylsulfonyl)phenyl]benzene;
1,2-difluoro-4-(4-methylphenyl)-5-[4-(methylsulfonyl)phenyl]benzene;
1,2-difluoro-4-(3,4-dimethylphenyl)-5-[4-(methylsulfonyl)phenyl]benzene;
1,2-difluoro-4-(3-fluoro-4-methylphenyl)-5-[4-(methylsulfonyl)phenyl]benzene;
4-(3-chloro-4-methylphenyl)-1,2-difluoro-5-[4-(methylsulfonyl)phenyl]benzene;
1,2-difluoro-4-(3-methoxy-4-methylphenyl)-5-[4-(methylsulfonyl)phenyl]benzene;
1,2-difluoro-4-(4-methoxyphenyl)-5-[4-(methylsulfonyl)phenyl]benzene;
1,2-difluoro-4-(4-methoxy-3-methylphenyl)-5-[4-(methylsulfonyl)phenyl]benzene;
1,2-difluoro-4-(3-fluoro-4-methoxyphenyl)-5-[4-(methylsulfonyl)phenyl]benzene;
4-(3-chloro-4-methoxyphenyl)-1,2-difluoro-5-[4-(memhylsulfonyl)phenyl]benzene;
1,2-difluoro-4-(3,4-dimethoxyphenyl)-5-[4-(methylsulfonyl)phenyl]benzene;
1,2-difluoro-4-(4-fluorophenyl)-5-[4-(methylsulfonyl)phenyl]benzene;
1,2-difluoro-4-(4-fluoro-3-methylphenyl)-5-[4-(methylsulfonyl)phenyl]benzene;
1,2-difluoro-4-(3,4-difluorophenyl)-5-[4-(methylsulfonyl)phenyl]benzene;
4-(3-chloro-4-fluorophenyl)-1,2-difluoro-5-[4-(methylsulfonyl)phenyl]benzene;
1,2-difluoro-4-(4-fluoro-3-methoxyphenyl)-5-[4-(methylsulfonyl)phenyl]benzene;
4-(4-chlorophenyl)-1,2-difluoro-5-[4-(methylsulfonyl)phenyl]benzene;
4-(4-chloro-3-methylphenyl)-1,2-difluoro5-[4-(methylsulfonyl)phenyl]benzene;
4-(4-chloro-3-fluorophenyl)-1,2-difluoro-5-[4-(methylsulfonyl)phenyl]benzene;
4-(3,4-dichlorophenyl)-1,2-difluoro-5-[4-(methylsulfonyl)phenyl]benzene;
4-(4-chloro-3-methoxyphenyl)-1,2-difluoro-5-[4-(methylsulfonyl)phenyl]benzene;
1,2-difluoro-4-(3,5-dimethylphenyl)-5-[4-(methylsulfonyl)phenyl]benzene;
1,2-difluoro-4-(3,5-difluorophenyl)-5-[4-(methylsulfonyl)phenyl]benzene;
4-(3,5-dichlorophenyl)-1,2-difluoro-5-[4-(methylsulfonyl)phenyl]benzene;
1,2-difluoro-4-(3,5-dimethoxyphenyl)-5-[4-(methylsulfonyl)phenyl]benzene;
1,2-difluoro-4-(3,4,5-trimethylphenyl)-5-[4-(methylsulfonyl)phenyl]benzene;
1,2-difluoro-4-(3,5-difluoro-4-methylphenyl)-5-[4-(methylsulfonyl)phenyl]benzene;
4-(3,5-dichloro-4-methylphenyl)-1,2-difluoro-5-[4-(methylsulfonyl)phenyl]benzene;
1,2-difluoro-4-(3,5-dimethoxy-4-methylphenyl)-5-[4-(methylsulfonyl)phenyl]benzene;
1,2-difluoro-4-(3,5-dimethyl-4-methoxyphenyl)-5-[4-(methylsulfonyl)phenyl]benzene;
1,2-difluoro-4-(3,5-difluoro-4-methoxyphenyl)-5-[4-(methylsulfonyl)phenyl]benzene;
4-(3,5-dichloro-4-methoxyphenyl)-1,2-difluoro-5-[4-(methylsulfonyl)phenyl]benzene;
1,2-difluoro-4-(3,4,5-trimethoxyphenyl)-5-[4-(methylsulfonyl)phenyl]benzene;
4-(3,5-dimethyl-4-fluorophenyl)-1,2-difluoro-5-[4-(methylsulfonyl)phenyl]benzene;
1,2-difluoro-4-(3,4,5-trifluorophenyl)-5-[4-(methylsulfonyl)phenyl]benzene;
4-(3,5-dichloro-4-fluorophenyl)-1,2-difluoro-5-[4-(methylsulfonyl)phenyl]benzene;
1,2-difluoro-4-(3,5-dimethoxy-4-fluorophenyl)-5-[4-(methylsulfonyl)phenyl]benzene;
4-(4-chloro-3,5-dimethylphenyl)-1,2-difluoro-5-[4-(methylsulfonyl)phenyl]benzene;
4-(4-chloro-3,5rs-difluorophenyl)-1,2-difluoro-5-[4-(methylsulfonyl)phenyl]benzene;
1,2-difluoro-4-(3,4,5-trichlorophenyl)-5-[4-(methylsulfonyl)phenyl]benzene; and
4-(4-chloro-3,5-dimethoxyphenyl)-1,2-difluoro-5-[4-(methylsulfonyl)phenyl]benzene.

Within Formula I there is a subclass of compounds of high interest represented by Formula II:

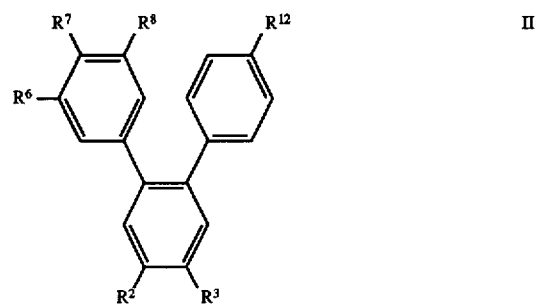

wherein each of $R^2$ and $R^3$ is independently selected from hydrido and halo; or wherein $R^2$ and $R^3$ together form —OCH$_2$O—; wherein each of $R^6$ through $R^8$ is independently selected from hydrido, lower alkyl, halo, lower alkoxy, lower haloalkyl, and lower dialkylamino; or wherein $R^6$ and $R^7$ together form —OCH$_2$O—; and wherein $R^{12}$ is selected from lower alkylsulfonyl and aminosulfonyl; or a pharmaceutically-acceptable salt thereof.

Within Formula I there is a second subclass of compounds of high interest represented by Formula III:

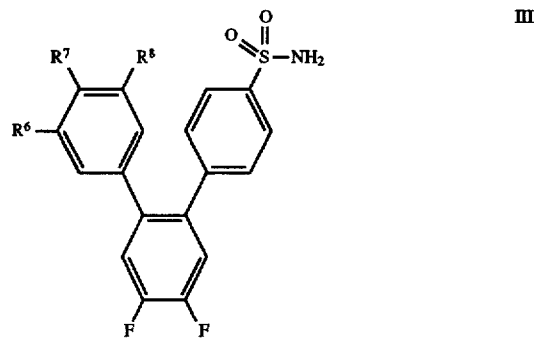

wherein each of $R^6$ through $R^8$ is independently selected from hydrido, halo, lower alkoxy, lower haloalkyl, amino, lower alkylamino, lower dialkylamino, and lower haloalkoxy; or wherein $R^6$ and $R^7$ together form —OCH$_2$O—; or a pharmaceutically-acceptable salt thereof.

The term "hydrido" denotes a single hydrogen atom (H). This hydrido radical may be attached, for example, to an oxygen atom to form a hydroxyl radical or two hydrido radicals may be attached to a carbon atom to form a methylene (—CH$_2$—) radical. Where the term "alkyl" is used, either alone or within other terms such as "haloalkyl" and "alkylsulfonyl", it embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tertbutyl, pentyl, isoamyl, hexyl and the like. The term "halo" means halogens such as fluorine, chlorine, bromine or iodine atoms. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1–6 carbon atoms. Examples of haloalkyl radicals include fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl difluoroethyl, difluoropropyl; dichloroethyl and dichloropropyl. The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. The terms "alkoxy" and "alkoxyalkyl" embrace linear or branched oxy-containing radicals each having alkyl portions of one to about ten carbon atoms, such as methoxy radical. More preferred alkoxy radicals are "lower alkoxy" radicals having one to six carbon atoms. Examples of such radicals include methoxy, ethoxy, propoxy, butoxy, tert-butoxy and methylenedioxy. The term "alkoxyalkyl" also embraces alkyl radicals having two or more alkoxy radicals attached to the alkyl radical, that is, to form monoalkoxyalkyl and dialkoxyalkyl radicals. More preferred alkoxyalkyl radicals are "lower alkoxyalkyl" radicals having one to six carbon atoms and one or two alkoxy radicals. Examples of such radicals include methoxymethyl, methoxyethyl, ethoxyethyl, methoxybutyl and methoxypropyl. The "alkoxy" radicals may be further substituted with one or more halo atoms, such as fluoro, chloro or bromo, to provide "haloalkoxy" radicals. Examples of such radicals include fluoromethoxy, chloromethoxy, trifluoromethoxy, trifluoroethoxy, fluoroethoxy and fluoropropoxy. The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl. The term "heterocyclic" embraces saturated, partially saturated and unsaturated heteroatom-containing ring-shaped radicals, where the heteroatoms may be selected from nitrogen, sulfur and oxygen. Examples of saturated heterocyclic radicals include saturated 3 to 6-membered heteromonocylic group containing 1 to 4 nitrogen atoms[e.g. pyrrolidinyl, imidazolidinyl, piperidino, piperazinyl, etc.]; saturated 3 to 6-membered heteromonocyclic group containing 1 to 2 oxygen atoms and 1 to 3 nitrogen atoms [e.g. morpholinyl, etc.]; saturated 3 to 6-membered heteromonocyclic group containing 1 to 2 sulfur atoms and 1 to 3 nitrogen atoms [e.g., thiazolidinyl, etc.]. Examples of partially saturated heterocyclic radicals include dihydrothiophene, dihydropyran, dihydrofuran and dihydrothiazole. The term "heteroaryl" embraces unsaturated heterocyclic radicals. Examples of unsaturated heterocyclic radicals, also termed "heteroaryl" radicals include unsaturated 5 to 6 membered heteromonocyclic group containing 1 to 4nitrogen atoms, for example, pyrrolyl, pyrrolinyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl, etc.] tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b] pyridazinyl, etc.], etc.; unsaturated 3 to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl 1,3,4-oxadiazolyl, 1,2,5-oxadiazolyl, etc.]etc.; unsaturated condensed heterocyclic group containing 1 to 2 oxygen atoms and 1 to 3 nitrogen atoms [e.g. benzoxazolyl, benzoxadiazolyl, etc.]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4thiadiazolyl, 1,2,5-thiadiazolyl, etc.] etc.; unsaturated condensed heterocyclic group containing 1 to 2 sulfur atoms and 1 to 3 nitrogen atoms [e.g., benzothiazolyl, benzothiadiazolyl, etc.] and the like. The term also embraces radicals where heterocyclic radicals are fused with aryl radicals. Examples of such fused bicyclic radicals include benzofuran, benzothiophene, and the like. Said "heterocyclic group" may have 1 to 3 substituents such as lower alkyl, hydroxy, oxo, amino and lower alkylamino. Preferred heterocyclic radicals include five to ten membered fused or unfused radicals. More preferred examples of heteroaryl radicals include benzofuryl, 2,3-dihydrobenzofuryl, benzothienyl, indolyl, dihydroindolyl, chromanyl, benzopyran, thiochromanyl, benzothiopyran, benzodioxolyl, benzodioxanyl, pyridyl, thienyl, thiazolyl, oxazolyl, furyl, and pyrazinyl. The term "sulfonyl", whether used alone or linked to other terms such as alkylsulfonyl, denotes respectively divalent radicals —$SO_2$—. "Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Examples of such lower alkylsulfonyl radicals include methylsulfonyl, ethylsulfonyl and propylsulfonyl. The terms "sulfamyl," "aminosulfonyl" and "sulfonamidyl" denotes a sulfonyl radical substituted with an amine radical, forming a sulfonamide (—$SO_2NH_2$). The terms "carboxy" or "carboxyl", whether used alone or with other terms, such as "carboxyalkyl", denotes —$CO_2H$. The term "alkylthio" embraces radicals containing a linear or branched alkyl radical, of one to ten carbon atoms, attached to a divalent sulfur atom. An example of "alkylthio" is methylthio, ($CH_3$—S—). The terms "N-alkylamino" and "N,N-dialkylamino" denote amino groups which have been substituted with one alkyl radical and with two alkyl radicals, respectively. More preferred alkylamino radicals are "lower alkylamino" radicals having one or two alkyl radicals of one to six carbon atoms, attached to a nitrogen atom. Suitable "alkylamino" may be mono or dialkylamino such as N-methylamino, N-ethylamino; N,N-dimethylamino, N,N-diethylamino or the like.

The present invention comprises a pharmaceutical composition for the treatment of inflammation and inflammation-associated disorders, such as arthritis, comprising a therapeutically-effective amount of a compound of Formula I in association with at least one pharmaceutically-acceptable carrier, adjuvant or diluent.

The present invention also comprises a therapeutic method of treating inflammation or an inflammation-associated disorder in a subject, the method comprising administering to a subject having or susceptible to such inflammation or inflammation associated disorder a therapeutically-effective amount of a compound of Formula I.

Also included in the family of compounds of Formula I are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, β-hydroxybutyric, salicyclic, galactaric and galacturonic acid. Suitable pharmaceutically-acceptable base addition salts of compounds of Formula I include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

General Synthetic Procedures

The compounds of the invention can be synthesized according to the following procedures of Schemes I-XI, wherein the $R^1$–$R^{14}$ substituents are as defined for Formula I. above, except where further noted.

SCHEME I

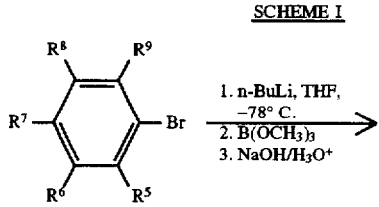

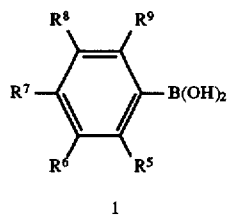

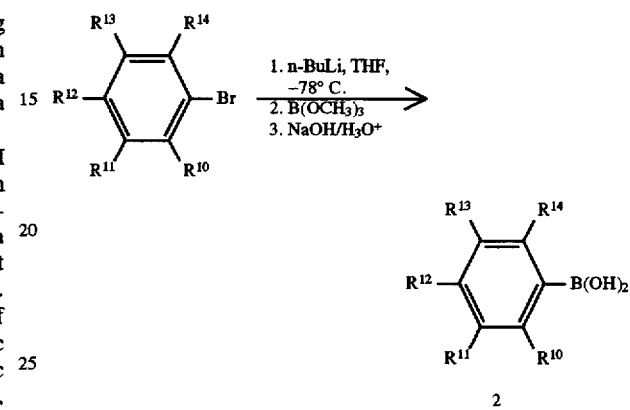

Synthetic Scheme I shows the three step procedure for the preparation of the prerequisite substituted phenylboronic acids 1 and 2 from commercially available phenyl bromides. In step one, halogen-metal interchange in THF at −78° C. generates the corresponding organolithium reagents. In step two, the organolithium species are reacted with trimethyl borate to give the corresponding methyl esters. In step three, hydrolysis with aqueous sodium hydroxide provides the substituted phenylboronic acids 1 and 2, respectively.

SCHEME II

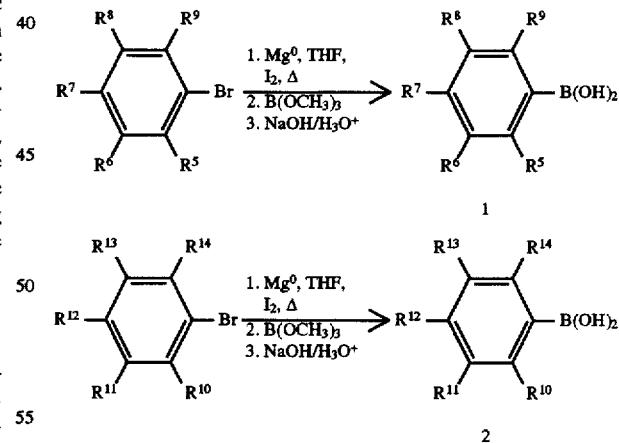

Synthetic Scheme II shows an alternative three step procedure for the preparation of the prerequisite substituted phenylboronic acids 1 and 2 from commercially available phenyl bromides. In step one, reaction with magnesium metal in THF at reflux in the presence of an iodine catalyst generates the corresponding Grignard reagents. In step two, the Grignard reagents are reacted with trimethyl borate to give the corresponding methyl esters. In step three, hydrolysis with aqueous sodium hydroxide provides the substituted phenylboronic acids 1 and 2, respectively.

SCHEME III

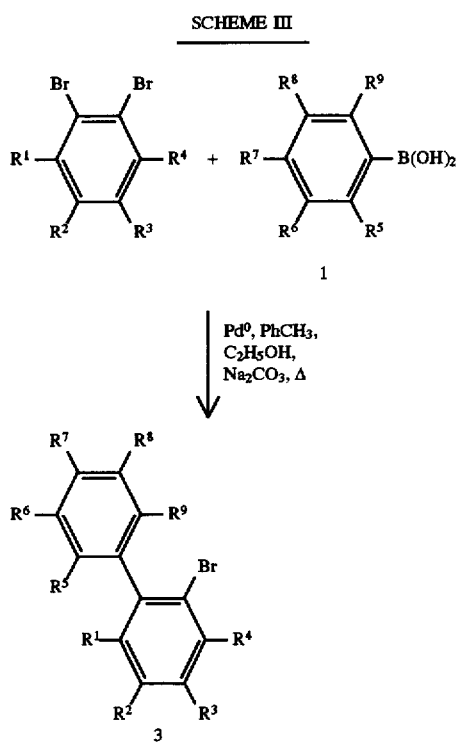

Synthetic Scheme III shows the procedure for the preparation of the substituted 2-bromo-biphenyl intermediates 3 from commercially available 1,2-dibromobenzenes and the appropriate substituted phenylboronic acid 1-(prepared in Synthetic Schemes I and II). Using a coupling procedure similar to the one developed by Suzuki et al. [Synth. Commun., 11, 513 (1981)], 1,2-dibromobenzenes are reacted with 1 in toluene/ethanol at reflux in the presence of a Pd°. catalyst, e.g., tetrakis(triphenylphosphine)palladium (O), and 2M sodium carbonate to give the corresponding substituted 2-bromobiphenyl intermediates 3.

SCHEME IV

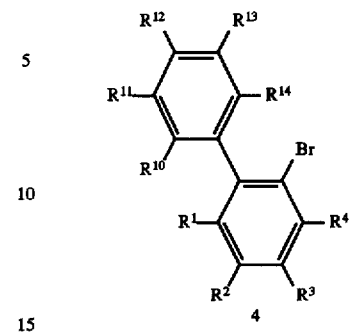

Synthetic Scheme IV shows the procedure for the preparation of the substituted 2-bromobiphenyl intermediates 4 from commercially available 1,2-dibromobenzenes and the appropriate substituted phenylboronic acids 2-(prepared in Synthetic Schemes I and II). Using a coupling procedure similar to the one developed by Suzuki et al. (Synthetic Scheme III), 1,2-dibromobenzenes are reacted with 2 in toluene/ethanol at reflux in the presence of a Pd° catalyst, e.g., tetrakis (triphenylphosphine)palladium(O), and 2M sodium carbonate to give the corresponding substituted 2-bromobiphenyl intermediates 4.

SCHEME V

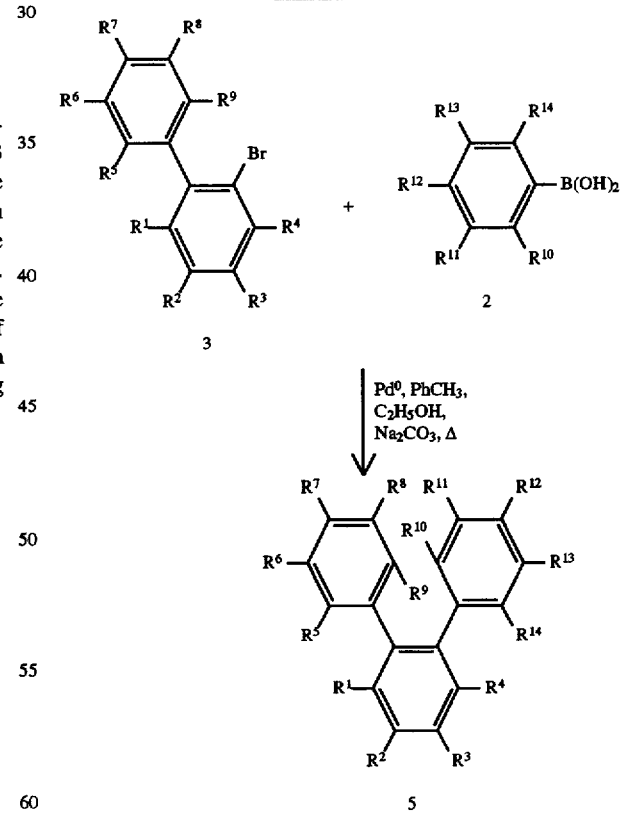

Synthetic Scheme V shows the procedure for the preparation of 1,2-diarylbenzene antiinflammatory agents 5 from 2-bromo-biphenyl intermediates 3-(prepared in Synthetic Scheme III) and the appropriate substituted phenylboronic acids 2-(prepared in Synthetic Schemes I and II). Using a coupling procedure similar to the one developed by Suzuki et al. (Synthetic Scheme III), intermediates 3 are reacted with 2 in toluene/ethanol at reflux in the presence of a Pd° catalyst, e.g., tetrakis(triphenylphosphine)palladium(O), and 2M sodium carbonate to give the corresponding 1,2-diarylbenzene antiinflammatory agents 5 of this invention.

SCHEME VI

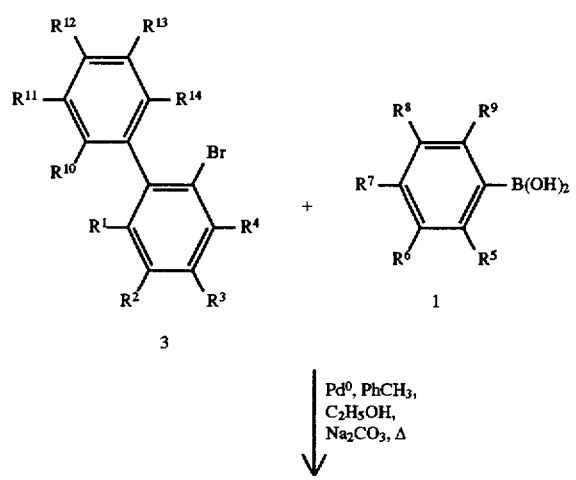

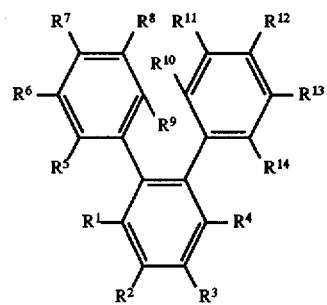

5

Synthetic Scheme VI shows the procedure for the preparation of 1,2-diarylbenzene antiinflammatory agents 5 from 2-bromo-biphenyl intermediates 4-(prepared in Synthetic Scheme IV) and the appropriate substituted phenylboronic acids 1-(prepared in Synthetic Schemes I and II). Using a coupling procedure similar to the one developed by Suzuki et al. (Synthetic Scheme III), intermediates 4 are reacted with 1 in toluene/ethanol at reflux in the presence of a Pd° catalyst, e.g., tetrakis(triphenylphosphine)palladium(O), and 2M sodium carbonate to give the corresponding 1,2-diarylbenzene antiinflammatory agents 5 of this invention.

SCHEME VII

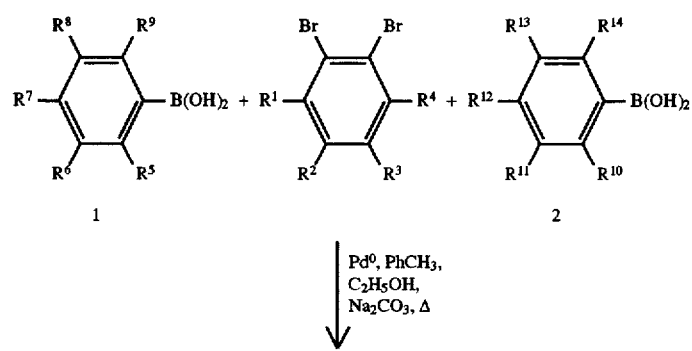

-continued
SCHEME VII

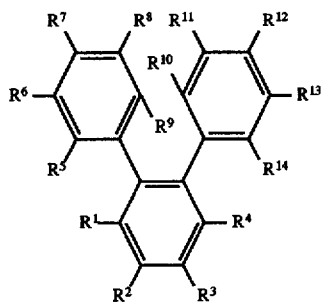

5

Synthetic Scheme VII shows an alternative one step procedure for the preparation of 1,2-diarylbenzene antiinflammatory agents 5 from commercially available 1,2-dibromobenzenes and the appropriate substituted phenylboronic acids 1 and 2-(prepared in Synthetic Schemes I and II). Using a coupling procedure similar to the one developed by Suzuki et al. (Synthetic Scheme III), an equimolar mixture of 1,2-dibromobenzenes, 1 and 2 are reacted in toluene/ethanol at reflux in the presence of a Pd° catalyst, e.g., tetrakis(triphenylphosphine)palladium(O), and 2M sodium carbonate to give the corresponding 1,2-diarylbenzene antiinflammatory agents 5 of this invention.

SCHEME VIII

-continued
SCHEME VIII

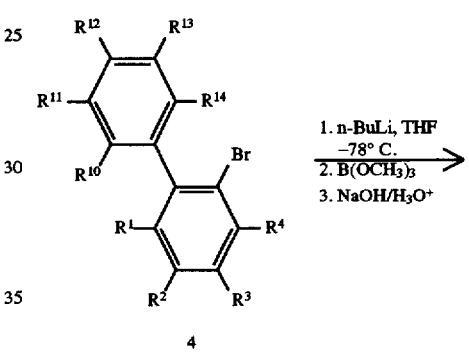

Synthetic Scheme VIII shows the three step procedure for the preparation of the 2-arylphenylboronic acids 6 and 7 from corresponding 2-bromobiphenyl intermediates 3-(prepared in Synthetic Scheme III) and 4-(prepared in Synthetic Scheme IV), respectively. In step one, halogen-metal interchange in THF at −78° C. generates the corresponding organolithium reagents. In step two, the organolithium species are reacted with trimethyl borate to give the corresponding methyl esters. In step three, hydrolysis with aqueous sodium hydroxide provides the substituted phenylboronic acids 6 and 7, respectively.

SCHEME IX

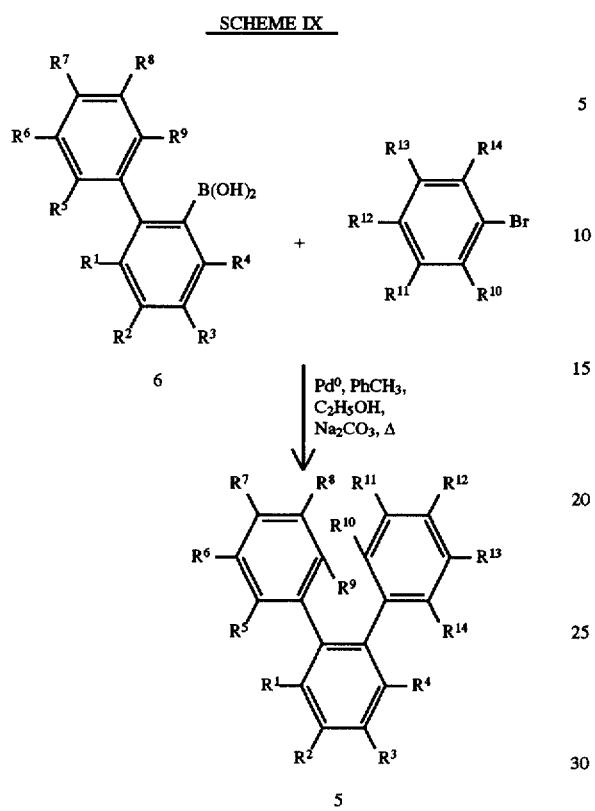

Synthetic Scheme IX shows the procedure for the preparation of 1,2-diarylbenzene antiinflammatory agents 5 from commercially available substituted phenyl bromides and 2-aryl-phenylboronic acids 6-(prepared in Synthetic Scheme VIII). Using a coupling procedure similar to the one developed by Suzuki et al. (Synthetic Scheme III), substituted phenyl bromides are reacted with 6 in toluene/ethanol at reflux in the presence of a Pd° catalyst, e.g., tetrakis (triphenylphosphine)palladium(O), and 2M sodium carbonate to give the corresponding 1,2-diarylbenzene antiinflammatory agents 5 of this invention.

SCHEME X

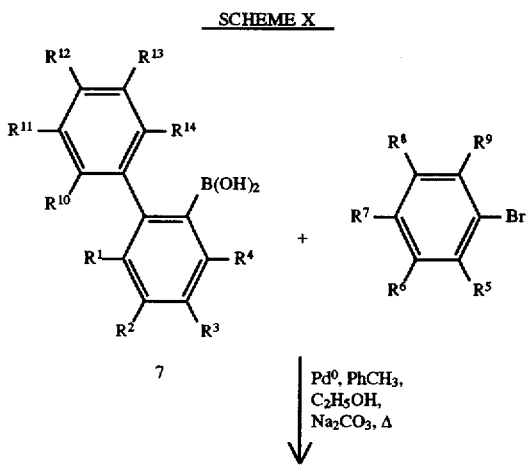

Synthetic Scheme X shows the procedure for the preparation of 1,2-diarylbenzene antiinflammatory agents 5 from commercially available substituted phenyl bromides and 2-aryl-phenylboronic acids 7-(prepared in Synthetic Scheme VIII). Using a coupling procedure similar to the one developed by Suzuki et al. (Synthetic Scheme III), substituted phenyl bromides are reacted with 7 in toluene/ethanol at reflux in the presence of a Pd° catalyst, e.g., tetrakis (triphenylphosphine) palladium(O), and 2M sodium carbonate to give the corresponding 1,2-diarylbenzene antiinflammatory agents 5 of this invention.

SCHEME XI

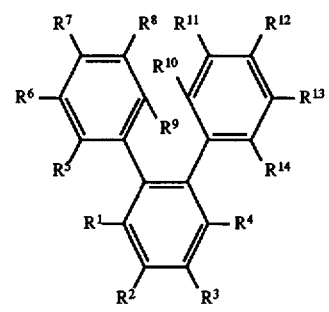

Synthetic Scheme XI shows the three step procedure for the preparation of sulfonamide antiinflammatory agents 9 from their corresponding methyl sulfones 8. Using a procedure similar to the one developed by Huang et al. [*Tetrahedron Lett.*, 35, 7201(1994)], THF solutions of the methylsulfones 8 at −78° C. are treated with base, e.g., n-BuLi, n-$C_3H_7$MgCl, etc., to generate the corresponding carbanions. In step two, the anions are treated with an organoborane, e.g., triethylborane, tributylborane, etc., at −78° C. and warmed to ambient temperature prior to stirring at reflux. In step three, an aqueous solution of sodium acetate and hydroxyamine-O-sulfonic acid is added to provide the corresponding sulfonamide antiinflammatory agents 9 (5 where $R^{12}=SO_2NH_2$) of this invention.

The following examples contain detailed descriptions of the methods of preparation of compounds of Formulas I–II. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated. HRMS is an abbreviation for High resolution mass spectrometry. The term "ND" signifies "not determined."

EXAMPLE 1

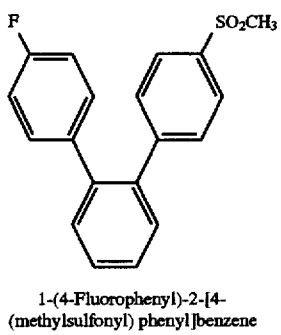

1-(4-Fluorophenyl)-2-[4-(methylsulfonyl) phenyl]benzene

Step 1

Preparation of 1-bromo-2-(4-fluorophenyl)benzene

Under nitrogen, 1.2 g (1.0 mmol) of Pd(PPh$_3$)4 was added to a stirred solution of 9.9 g (42 mmol) of 1,2-dibromobenzene (Aldrich) and 3.0 g (21 mmol) of 4-fluorophenylboronic acid in 42 mL of toluene, 42 mL of ethanol and 42 mL of 2M Na$_2$CO$_3$. After vigorous stirring at reflux for 3 hours, the solvent was removed in vacuo. The residue was dissolved in ethyl acetate. The resulting solution was washed with water and dried over MgSO$_4$. Purification by silica gel chromatography (Waters Prep-500A) with hexane gave 4.35 g (81%) of 1-bromo-2-(4-fluorophenyl) benzene as a colorless oil: NMR (CDCl$_3$) δ 7.07–7.26 (m, 3H), 7.27–7.44 (m, 4H), 7.67(d, J=8 Hz, 1H).

Step 2

Preparation of 4-methylthiophenylboronic acid

Under nitrogen, 113 mL (181 mmol) of n-BuLi (1.6M in hexanes) was added to a stirred solution of 30 g (150 mmol) of 4-bromothioanisole (Lancaster) in 1,500 mL of anhydrous tetrahydrofuran (THF) at —78° C. After 30 minutes, 51 mL (450 mol) of trimethylborate was added. The reaction was warmed to ambient temperature and stirred overnight. The resulting solution was treated with 300 mL of 10% NaOH and stirred vigorously for 1 hour. The THF was removed in vacuo, the pH adjusted to 4–5 and the solid collected by filtration. The solid was washed repeatedly with water and hexane. Drying in vacuo gave 21 g (83%) of 4-methylthiophenylboronic acid as a colorless solid: NMR (DMSO-d$_6$) δ 2.47 (s, 3H), 7.20 (d, J=8 Hz, 2H), 7.71 (d, J=8 Hz, 2H), 7.96 s,

Step 3

Preparation of 1-(4-fluorophenyl)-2-[4-(methylthio) phenyl]benzene

Under nitrogen, 200 mg of Pd(PPh$_3$)$_4$ was added to a stirred solution of 500 mg (2.0 mmol) of 1-bromo-2-(4-fluorophenyl)benzene (Step 1) and 500 mg (3.0 mmol) of 4-methylthiophenylboronic acid (Step 2) in 7 mL of toluene, 7 mL of ethanol and 7 mL of 2M Na$_2$CO$_3$. After vigorous stirring at reflux overnight, the solvent was removed in vacuo. The residue was dissolved in ethyl acetate. The resulting solution was washed with water and dried over MgSO$_4$. Purification by silica gel chromatography (Waters LC-2000) with ethyl acetate/hexane (2:98) as the eluent gave 550 mg of 1-(4-fluorophenyl)-2-[4-(methylthio) phenyl]benzene as a semi-solid: NMR (CDCl$_3$) δ 2.46 (s, 3H), 6.92 (t, J=8 Hz, 2H), 7.02–7.14 (m, 6H) 7.37–7.42 (m, 4H). MS (EI): m/e (rel intensity) 294 (100), 279 (39), 277 (56), 246 (74), 227 (40), 190 (43) 190 (38), 140 (44).

Step 4

Preparation of 1-(4-fluorophenyl)-2-[4-(methylsulfonyl)phenyl]benzene

To a stirred solution of 550 mg (1.9 mmol) of crude 1-(4-fluoro-phenyl)-2-[4-(methylthio)phenyl]benzene (Step 3) in 10 mL of methylene chloride at ambient temperature was slowly added 1.3 g (4.1 mmol) of 3-chloroperoxybenzoic acid (ca. 55%). Stirring was continued for 20 minutes prior to the addition of 1 g of Na$_2$SO$_3$. The reaction was allowed to stir for an additional 10 minutes and the solvent removed in vacuo. The residue was dissolved in ethyl acetate and the resulting solution washed twice with saturated NaHCO3 and dried over MgSO$_4$. Recrystallization from ethyl acetate/hexane gave 437 mg (94%) of 1-(4-fluorophenyl)-2-[4-(methylsulfonyl)phenyl] benzene as a colorless solid: mp 178.0°–179.0° C.; NMR (CDCl$_3$) δ 3.05 (s, 3H), 6.93 (t, J=8 Hz, 2H), 7.03–7.09 (m, 2H), 7.32 (d, J=8 Hz, 2H), 7.38–7.50 (m, 4H), 7.80 (d, J=8 Hz, 2H). MS (FAB): m/e 333 (M+Li). Anal. Calc'd for C$_{19}$H$_{15}$FO$_2$S: C, 69.86; H, 4.60; F, 5.79. Found: C, 69.74; H, 4.72; F, 5.51.

EXAMPLE 2

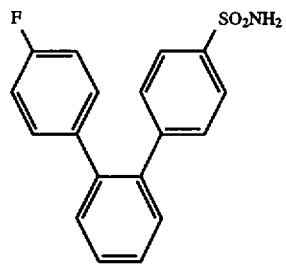

4-[2-(4-Fluorophenyl)phenyl]benzenesulfonamide

Step 1

Preparation of 2-(4-fluorophenyl)phenylboronic acid

Following the general procedure outlined in Synthetic Scheme VIII, 4.35 g (17.3 mmol) of 1-bromo-2-(4-fluorophenyl)benzene (Example 1, Step 1) was converted to 2-(4-fluorophenyl)phenylboronic acid: NMR (CDCl$_3$) δ 4.27 (s, 2H), 7.09–7.20 (m, 2H), 7.25–7.32 (m, 1H), 7.34–7.53 (m, 4H), 7.90 (d, J=8 Hz, 1H).

Step 2

Preparation of 4-[2-(4-fluorophenol)phenyl] benzenesulfonamide

Following the general procedure outlined in Synthetic Scheme IX, 1.5 g (6.9 mmol) of 2-(4-fluorophenyl) phenylboronic acid (Step 1) was reacted with 2.5 g (10.4 mmol) of 4-bromobenzenesulfonamide (Lancaster). Purification by silica gel chromatography (Waters LC-2000) with ethyl acetate/hexane (3:7) and subsequent recrystallization from ethyl acetate/hexane gave 1.04 g (46%) of 4-[2-(4-fluorophenyl)phenyl] benzenesulfonamide as a colorless solid: mp 187.3—188.2° C.; NMR (CDCl$_3$) δ 4.83 (s, 2H), 6.92 (t, J=9 Hz, 2H), 7.02–7.11 (m, 2H), 7.27 (d, J=9 Hz, 2H), 7.36–7.50 (m, 4H), 7.78 (d, J=8 Hz, 2H). MS (EI): m/e (rel intensity) 327 (75) 245 (100); HRMS Calc'd for $C_{18}H_{14}FNO_2S$: 327.0729. Found: 327.0743. Anal. Calc'd for $C_{18}H_{14}FNO_2S$: C, 66.04; H, 4.31; N, 4.28.

Found: C, 65.86; H, 4.51; N, 4.34.

EXAMPLE 3

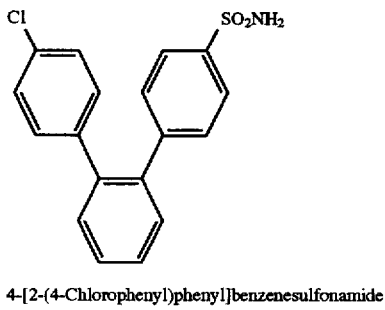

4-[2-(4-Chlorophenyl)phenyl]benzenesulfonamide

Step 1

Preparation of 1-bromo-2-(4-chlorophenyl)benzene

Following the general procedure outlined in Synthetic Scheme III, 9.0 g (38 mmol) of 1,2-dibromobenzene was reacted with 3.0 g (19 mmol) of 4-chlorophenylboronic acid (Lancaster). Purification by silica gel chromatography (Waters Prep-500A) with hexane gave 4.39 g (84%) of 1-bromo-2-(4-chlorophenyl)benzene as a colorless oil: NMR (CDCl$_3$) δ 7.18–7.26 (m, 1H), 7.28–7.44 (m, 6H), 7.68 (dd, J=1.5, 8 Hz, 1H).

Step 2

Preparation of 2-(4-chlorophenyl)phenylboronic acid

Following the general procedure outlined in Synthetic Scheme VIII, 4.39 g (16.4 mmol) of 1-bromo-2-(4chlorophenyl)benzene (Step 1) was converted to 2-(4chlorophenyl)phenylboronic acid: NMR (CDCl$_3$) δ 4.20 (s, 2H), 7.19–7.55 (m, 7H), 7.89 (d, J=8 Hz, 1H).

Step 3

Preparation of 4-[2-(4-chlorophenyl)phenyl]benzenesulfonamide

Following the general procedure outlined in Synthetic Scheme IX, 1.6 g (6.9 mmol) of 2-(4-chlorophenyl)phenylboronic acid (Step 2) was reacted with 1.8 g (7.6 mmol) of 4-bromobenzenesulfonamide. Purification by silica gel chromatography (Waters LC-2000) with ethyl acetate/hexane (3:7) and subsequent recrystallization from ethyl acetate/hexane gave 1.59 g (67%) of 4-[2-(4-chlorophenyl)phenyl]benzenesulfonamide as a colorless solid: mp 206.2°–207.0° C.; NMR (CDCl$_3$) δ 4.77 (s, 2H), 7.04 (d, J=9 Hz, 2H), 7.16–7.31 (m, 4H), 7.36–7.51 (m, 4H), 7.80(d, J=9 Hz, 2H). MS (EI): m/e (rel intensity) 343 (100), 308 (13), 262 (21), 228 (82); HRMS Calc'd for $C_{18}H_{14}ClNO_2S$: 343.0434. Found: 343.0434.

Anal. Calc'd for $C_{18}H_{14}ClNO_2S$: C, 62.88; H, 4.10; N, 4.07.

Found: C, 62.66; H, 4.36; N, 4.09.

EXAMPLE 4

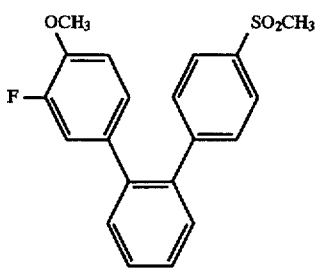

2-Fluoro-1-methoxy-4-[2-[4-(methylsulfonyl)phenyl]phenyl]benzene

Step 1

Preparation of 1-bromo-2-[4-(methylthio)phenyl]benzene

Following the general procedure outlined in Synthetic Scheme IV, 33 g (140 mmol) of 1,2-dibromobenzene was reacted with 12 g (70 mmol) of 4-methylthiophenylboronic acid (Example 1, Step 2). Purification by silica gel chromatography with hexane gave 17.2 g (89%) of 1-bromo-2-[4-(methylthio)phenyl]benzene as a colorless oil: NMR (CDCl$_3$) δ 2.53 (s, 3H), 7.16–7.23 (m, 1H), 7.28–7.39 (m, 6H), 7.66 (d, J=8 Hz, 1H).

Step 2

Preparation of 1-bromo-2-[4-(methylsulfonyl)phenyl]benzene

Following the synthetic procedure outlined in Step 4 of Example 1, 17.1 g (61.3 mmol) of 1-bromo-2-[4-(methylthio)phenyl]benzene (Step 1) was oxidized to its corresponding sulfone. Purification by silica gel chromatography (Waters Prep-500A) with ethyl acetate/hexane (3:7) gave 16.2 g (85%) of 1-bromo-2-[4-(methylsulfonyl) phenyl]benzene as a colorless solid: mp 168.2°–169.5° C.; NMR (CDCl$_3$) δ 3.12 (s, 3H), 7.23–7.33 (m, 2H), 7.40 (dt, J=1.5, 8 Hz, 1H), 7.61 (d, J=8 Hz, 2H), 7.70 (dd, J=1.5, 8 Hz, 1H), 8.01 (d, J=9 Hz, 2H).

Step 3

Preparation of 3-fluoro-4-methoxyphenylboronic acid

Following the general procedure outlined in Synthetic Scheme I, 15 g (73 mmol) of 4-bromo-2-fluoroanisole was converted to 3-fluoro-4-methoxyphenylboronic acid: NMR (CDCl$_3$) δ 3.75 (s, 3H), 6.80 (d, J=8 Hz, 1H), 7.36–7.48 (m, 2H).

Step 4

Preparation of 2-fluoro-1-methoxy-4-[2-[4-(methylsulfonyl)phenyl]phenyl]benzene Following the general procedure outlined in Synthetic Scheme VI, 5.0 g (16 mmol) of 1-bromo-2-[4-(methylsulfonyl)phenyl]benzene (Step 2) was reacted with 4.1 g (24 mmol) of 3-fluoro-4-methoxyphenylboronic acid (Step 3). Purification by silica gel chromatography (Waters Prep-500A) with ethyl acetate/hexane (35:65) and subsequent recrystallization from ethyl acetate/hexane gave 4.82 g (88%) of 2-fluoro-1-methoxy-4-[2-[4-(methylsulfonyl)phenyl]phenyl]benzene as a colorless solid:

mp 136.2°–136.6° C.; NMR (CDCl$_3$) δ 3.06 (s, 3H), 3.87 (s, 3H), 6.72–6.89 (m, 3H), 7.31–7.51 (m, 6H), 7.81(d, J=9 Hz, 2H). MS (EI): m/e (rel intensity) 356 (100), 262 (28) 246 (22); HRMS Calc'd for C$_{20}$H$_{17}$FO$_3$S: 356.0882. Found: 356.0881. Anal. Calc'd for C$_{20}$H$_{17}$FO$_3$S: C, 67.40; H, 4.81; F, 5.33. Found: C, 67.24; H, 4.83; F, 5.25.

EXAMPLE 5

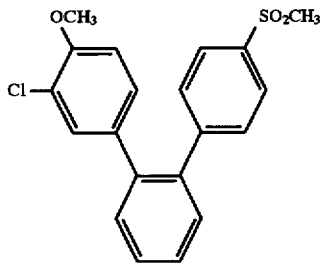

2-Chloro-1-methoxy-4-[2-[4-(methylsulfonyl)phenyl]phenyl]benzene

Step 1

Preparation of 4-bromo-2-chloroanisole

Under nitrogen, 7.3 mL (77 mmol) of dimethylsulfate was added to a stirred suspension of 10 g (48 mmol) of 4-bromo-2-chlorophenol and 5.4 g (38 mmol) of powered K$_2$CO$_3$ in 75 mL of fresh acetone. After 2 hours at reflux, the reaction was cooled to ambient temperature, filtered, and concentrated in vacuo. The residue was dissolved in ethyl acetate; the resulting solution was washed with water and dried over MgSO$_4$. Concentration in vacuo gave 10.2 g (96%) of 4-bromo-2-chloroanisole as a colorless solid: mp 68.5°–70.5° C.; NHR (CDCl$_3$) δ 3.88 (s, 3H), 6.80 (d, J=9 Hz, 1H), 7.33 (dd, J=2, 9 Hz, 1H), 7.50 (d, J=2 Hz, 1H).

Step 2

Preparation of 3-chloro-4-methoxyphenylboronic acid

Following the general procedure outlined in Synthetic Scheme I, 10.2 g (46.2 mmol) of 4-bromo-2-chloroanisole (Step 1) was converted to 3-chloro-4-methoxyphenylboronic acid: NMR (CDCl$_3$) δ 3.83 (s, 3H), 6.57 (s, 2H), 6.83 (d, J=8 Hz, 1H), 7.64 (dd, J=1.5, 8 Hz, 1H), 7.77 (d, J=1.5 Hz, 1H).

Step 3

Preparation of 2-chloro-1-methoxy-4-[2-[4-(methylsulfonyl)phenyl]phenyl]benzene

Following the general procedure outlined in Synthetic Scheme VI, 4.0 g (13 mmol) of 1-bromo-2-[4-(methylsulfonyl)phenyl]benzene (Example 4, Step 2) was reacted with 2.86 g (15.4 mmol) of 3-chloro-4-methoxyphenylboronic acid (Step 2). Purification by silica gel chromatography (Waters PrepLC 500A) with ethyl acetate/hexane (35:65) and subsequent recrystallization from ethyl acetate/hexane gave 3.31 g (69%) of 2-chloro-1-methoxy-4-[2-[4-(methylsulfonyl)phenyl]phenyl]benzene as a colorless solid: mp 161.5°–162.3° C.; NMR (CDCl$_3$) δ 3.05 (s, 3H), 3.88 (s, 3H), 6.75 (d, J=9 Hz, 1H), 6.87 (dd, J=1.5, 9 Hz, 1H), 7.17 (d, J=2 Hz, 1H), 7.34(d, J=9 Hz, 2H), 7.37–7.51 (m, 4H), 7.82 (d, J=8 Hz, 2H). MS (EI): m/e (rel intensity) 372 (100), 243 (24); HRMS Calc'd for C$_{20}$H$_{17}$ClO$_3$S: 372.0587. Found: 372.0557. Anal. Calc'd for C$_{20}$H$_{17}$ClO$_3$S: C, 64.43; H, 4.60; Cl, 9.51. Found: C, 64.17; H, 4.56; Cl, 9.63.

EXAMPLE 6

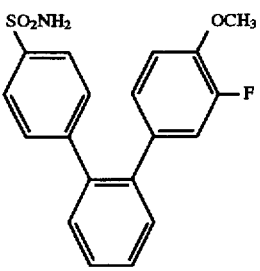

4-[2-(3-Fluoro-4-methoxyphenyl)phenyl]benzenesulfonamide

Step 1

Preparation of 4-[2-(3-fluoro-4-methoxyphenyl)phenyl]benzenesulfonamide

Under nitrogen, 5.8 mL (9.2 mmol) of propylmagnesium chloride (1.6M in Et$_2$O) was added to a stirred solution of 3.0 g (8.4 mmol) of 2-fluoro-1-methoxy-4-[2-[4-(methylsulfonyl)phenyl]phenyl]benzene (the title compound of Example 4, Step 4) in 9.6 mL of anhydrous tetrahydrofuran at 0° C. The resulting solution was warmed to ambient temperature and stirred for 30 minutes. The reaction was cooled to 0° C. prior to the addition of 12.6 mL (12.6 mmol) of triethylborane (1.0M in THF). The reaction was warmed to ambient temperature and stirred for 90 minutes prior to stirring at reflux for 40 hours. The reaction was cooled to 0° C. and treated with 6.4 g (78mmol) of sodium acetate, 3.8 g (34 mmol) of hydroxylamine-O-sulfonic acid, and 11 mL of water; stirring was continued as the reaction slowly warmed to ambient temperature. The reaction mixture was diluted with water and extracted three times with ethyl acetate. The combined ethyl acetate extractions were washed with brine and dried over MgSO$_4$. Purification by silica gel chromatography (Waters LC-2000) with ethyl acetate/hexane (3:7) and subsequent recrystallization from ethyl acetate/hexane gave 2.0 g (67%) of 4-[2-(3-fluoro-4-methoxyphenyl)phenyl]benzenesulfonamide as a colorless solid: mp 143.5°–145.5° C. (dec); NMR (CDCl$_3$) δ 3.96 (s, 3H), 4.90 (s, 2H), 6.74–6.90 (m, 3H), 7.29 (d, J=9 Hz, 2H), 7.35–7.48 (m, 4H), 7.79 (d, J=9 Hz, 2H). MS (FAB): m/e 364 (M+Li); HRMS Calc'd for C$_{19}$H$_{16}$FNO$_3$S: 357.0835.

Found: 357.0809. Anal. Calc'd for C$_{19}$H$_{16}$FNO$_3$S (0.20 ethyl acetate & 0.13 H$_2$O) C, 63.04; H, 4.77; N, 3.71. Found: C, 63.03; H, 4.59; N, 3.52.

EXAMPLE 7

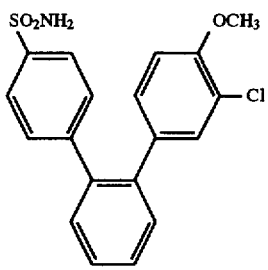

4-[2-(3-Chloro-4-methoxyphenyl)phenyl]benzenesulfonamide

Following the general procedure outlined in Synthetic Scheme XI, 2.5 g (6.7 mmol) of 2-chloro-1-methoxy-4-[2-[4-(methylsulfonyl)phenyl]phenyl]benzene (the title compound of Example 5) was converted to its corresponding sulfonamide. Purification by silica gel chromatography (Waters LC-2000) with ethyl acetate/hexane (3:7) and subsequent recrystallization from ethyl acetate/hexane gave 1.31 g (52%) of 4-[2-(3-chloro-4-methoxyphenyl)phenyl] benzenesulfonamide as a colorless solid: mp 179.5°–180.2° C.; NMR (CDCl$_3$) δ 3.87 (s, 3H), 4.76 (s, 2H), 6.75 (d, J=9 Hz, 1H), 6.86 (dd, J=2, 9 Hz, 1H), 7.20 (d, J=3 Hz, 1H), 7.29 (d, J=9 Hz, 2H), 7.35–7.47 (m, 4H), 7.79 (d, J=8 Hz, 2H). MS (EI): m/e (rel intensity) 373 (100), 258 (17), 243 (29); HRMS Calc'd for C$_{19}$H$_{16}$ClNO$_3$S: 373.0539. Found: 373.0587. Anal. Calc'd for C$_{19}$H$_{16}$ClNO$_3$S: C, 61.04; H, 4.31; N, 3.75. Found: C, 60.76; H, 4.28; N, 3.48.

EXAMPLE 8

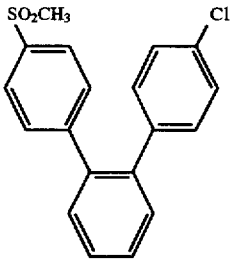

1-(4-Chlorophenyl)-2-[4-(methylsulfonyl)phenyl]benzene

Following the general procedure outlined in Synthetic Scheme VI, 2.3 g (7.4 mmol) of 1-bromo-2-[4-(methylsulfonyl)phenyl]benzene (Example 4, Step 2) was reacted with 1.7 g (11 mmol) of 4-chlorophenylboronic acid. Purification by silica gel chromatography (Waters Prep-500A) with ethyl acetate/hexane (1:3) and subsequent recrystallization from ethyl acetate/hexane gave 1.90 g (74%) of 1-(4-chlorophenyl)-2-[4-(methylsulfonyl)phenyl] benzene as a colorless solid: mp 180.2°–180.6° C.; NMR (CDCl$_3$) δ 3.06 (s, 3H), 7.04 (d, J=8 Hz, 2H), 7.21 (d, J=8 Hz, 2H), 7.33 (d, J=9 Hz, 2H), 7.38–7.51 (m, 4H), 7.81 (d, J=8 Hz, 2H). MS (EI): m/e (rel intensity) 342 (34), 228 (100); HRMS Calc'd for C$_{19}$H$_{15}$ClO$_2$S: 342.0481. Found: 342.0484. Anal. Calc'd for C$_{19}$H$_{15}$ClO$_2$S: C, 66.56; H, 4.41; Cl, 10.34. Found: C, 66.45; H, 4.48; Cl, 10.63.

EXAMPLE 9

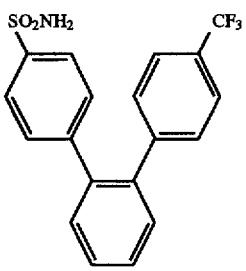

4-[2-[4-(Trifluoromethyl)phenyl]phenyl]benzenesulfonamide

Step 1

Preparation of 4-(trifluoromethyl)phenylboronic acid

Following the general procedure outlined in Synthetic Scheme I, 8.9 g (39 mmol) of 4-bromobenzotrifluoride was converted to 4-(trifluoromethyl)phenylboronic acid.

Step 2

Preparation of 1-[4-(trifluoromethyl)phenyl]-2-[4-(methylsulfonyl)phenyl]benzene Following the general procedure outlined in Synthetic Scheme VI, 4.0 g (13 mmol) of 1-bromo-2-[4-(methylsulfonyl)phenyl]benzene (Example 4, Step 2) was reacted with 3.8 g (20 mmol) of 4-(trifluoromethyl) phenylboronic acid (Step 1). Purification by silica gel chromatography (Waters Prep-500A) with ethyl acetate/hexane (1:3) and subsequent recrystallization from ethyl acetate/ hexane gave 3.80 g (77%) of 1-[4-(trifluoromethyl)phenyl] -2-[4-(methylsulfonyl)phenyl]benzene as a colorless solid: mp 172.8°–173.5° C.; NMR (CDCl$_3$) δ 3.06 (s, 3H), 7.23 (d, J=8 Hz, 2H), 7.33 (d, J=9 Hz, 2H), 7.41–7.46 (m, 2H), 7.48–7.54 (m, 4H), 7.81 (d, J=9 Hz, 2H). MS (ES): m/e 383 (M+Li); HRMS Calc'd for C$_{20}$H$_{15}$F$_3$O$_2$S: 376.0745. Found: 376.0766.

Step 3

Preparation of 4-[2-[4-(trifluoromethyl)phenyl] phenyl]benzenesulfonamide

Following the synthetic procedure outlined in Synthetic Scheme XI, 2.62 g (6.96 mmol) of 1-[4-(trifluoromethyl) phenyl]-2-[4-(methylsulfonyl)phenyl]benzene (Step 2) was converted to its corresponding sulfonamide. Purification by silica gel chromatography (Water Prep-500A) with ethyl acetate/hexane (3:7) and subsequent recrystallization from ethyl acetate/hexane gave 1.85 g (70%) of 4-[2-[4-(trifluoromethyl)phenyl]phenyl]benzenesulfonamide as a colorless solid: mp 187.5°–187.8° C.; NMR (CDCl$_3$) δ 4.79 (s, 2H), 7.20–7.31 (m, 4H), 7.38–7.54 (m, 6H), 7.80 (d, J=8 Hz, 2H). MS (EI): m/e (rel intensity) 377 (14), 297 (25), 228 (100); HRMS Calc'd for C$_{19}$H$_{14}$F$_3$NO$_2$S: 377.0697. Found: 377.0737. Anal. Calc'd for C$_{19}$H$_{14}$F$_3$NO$_2$S: C, 60.47; H, 3.74; N, 3.71. Found: C, 60.43; H, 3.97; N, 3.48.

EXAMPLE 10

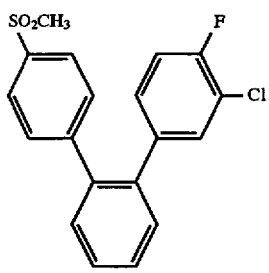

2-Chloro-1-fluoro-4-[2-[4-(methylsulfonyl)phenyl]phenyl]benzene

Step 1

Preparation of 2-chloro-1-fluoro-4-[2-[4-(methylsulfonyl)phenyl]phenyl]benzene

Following the general procedure outlined in Synthetic Scheme VI, 6.43 g (20.6 mmol) of 1-bromo-2-[4-(methylsulfonyl)phenyl]benzene (Example 4, Step 2) was reacted with 5.37 g (30.9 mmol) of 3-chloro-4-fluorophenylboronic acid. Purification by silica gel chromatography (Waters Prep-500A) with ethyl acetate/hexane (1:3) gave 6.64 g (89%) of 2-chloro-1-fluoro-4-[2-[4-(methylsulfonyl)phenyl]phenyl]benzene as a colorless solid: mp 179.5°–181.1° C.; NMR (CDCl$_3$) δ 3.06 (s, 3H), 6.86–6.93 (m, 1H), 6.98 (t, J=8 Hz, 1H), 7.19 (dd, J=2, 7 Hz, 1H), 7.33 (d, J=8 Hz, 2H), 7.38–7.53 (m, 4H), 7.84 (d, J=9 Hz, 2H). MS (FAB): m/e 367 (M+Li); HRMS Calc'd for C$_{19}$H$_{14}$ClFO$_2$S: 360.0387. Found: 360.0401. Anal. Calc'd for C$_{19}$H$_{14}$ClFO$_2$S: C, 63.25; H, 3.91; F, 5.27. Found: C, 62.92; H, 4.02; F, 5.19.

EXAMPLE 11

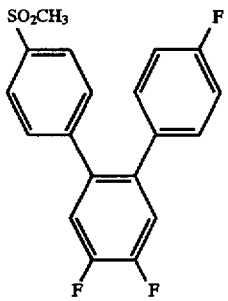

1,2-Difluoro-4-(4-fluorophenyl)-5-[4-(methylsulfonyl)phenyl]benzene

Step 1

Preparation of 1,2-difluoro-4-(4-fluorophenyl)-5-[4-(methylthio)phenyl]benzene

Under nitrogen, 3 g (2.6 mmol) of Pd(PPh$_3$)$_4$ was added to a stirred solution of 5.0 g (18 mmol) of 1,2-dibromo-4,5-difluorobenzene (Aldrich), 4.2 g (25 mmol) of 4-methylthiophenylboronic acid (Example 1, Step 2), and 3.1 g (22 mmol) of 4-fluorophenylboronic acid in 100 mL of toluene, 100 mL of ethanol, and 100 mL of 2M Na$_2$CO$_3$. After vigorous stirring at reflux overnight, the solvent was removed in vacuo and the residue dissolved in ethyl acetate. The resulting solution was washed with water and dried over MgSO$_4$. Purification by silica gel chromatography gave 1,2-difluoro-4-(4-fluorophenyl)-5-[4-(methylthio)phenyl]benzene as a semi-solid which was used without further purification.

Step 2

Preparation of 1,2-difluoro-4-(4-fluorophenyl)-5-[4-(methylsulfonyl)phenyl]benzene To a stirred solution of 6.34 g (ca. 18 mmol) of the crude 1,2-difluoro-4-(4-fluorophenyl)-5-[4-(methylthio)phenyl]benzene (Step 1) in 125 mL of methylene chloride at 0° C. was slowly added 14.6 g (54 mmol) of 3-chloroperoxybenzoic acid (ca 64%); after stirring for 90 minutes, the reaction was diluted with additional methylene chloride, washed with 3 times with 5% NaOH, and dried over MgSO$_4$. Purification by silica gel chromatography (Waters Prep-500A) with ethyl acetate/hexane (1:3) and subsequent recrystallization from ethyl acetate/hexane gave 2.81 g (43%) of 1,2-difluoro-4-(4-fluorophenyl)-5-[4-(methylsulfonyl)phenyl]benzene as a colorless solid: mp 172.8°–173.5° C.; NMR (CDCl$_3$) δ 3.05 (s, 3H), 6.94 (t, J=8 Hz, 2H), 6.98–7.06 (m, 2H), 7.21–7.31 (m, 4H), 7.81 (d, J=8 Hz, 2H). MS (FAB): m/e 369 (M+Li); HRMS Calc'd for C$_{19}$H$_{13}$F$_3$O$_2$S: 362.0588. Found: 362.0586. Anal. Calc'd for C$_{19}$H$_{13}$F$_3$O$_2$S: C, 62.98; H, 3.62; F, 15.73. Found: C, 62.96; H, 3.70; F, 15.76.

EXAMPLE 12

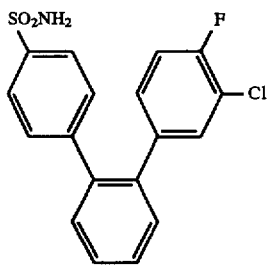

4-[2-(3-Chloro-4-fluorophenyl)phenyl]benzenesulfonamide

Following the general procedure outlined in Synthetic Scheme XI, 5.0 g (14 mmol) of 2-chloro-1-fluoro-4-[2-[4-(methylsulfonyl)phenyl]phenyl]benzene (the title compound of Example 10) was converted to its corresponding sulfonamide. Purification by silica gel chromatography (Waters Prep-500A) with ethyl acetate/hexane (28:72) and subsequent recrystallization from ethyl acetate/hexane gave 1.47 g (29%) of 4-[2-(3-chloro-4-fluorophenyl)phenyl]benzenesulfonamide as a colorless solid: mp 192.5°–193.2° C.; NMR (CDCl$_3$) δ 6.36 (s, 2H), 6.68–6.76 (m, 1H), 6.81 (t, J=9 Hz, 1H), 7.06 (d, J=8 Hz, 2H), 7.17–7.32 (m, 5H), 7.63 (d, J=8, 2H). MS (FAB): m/e 368 (M+Li); HRMS Calc'd for C$_{18}$H$_{13}$ClFNO$_2$S: 361.0340.

Found: 361.0338. Anal. Calc'd for C$_{18}$H$_{13}$ClFNO$_2$S: C, 59.75; H, 3.62; N, 3.87. Found: C, 59.80; H, 3.91; N, 4.05.

EXAMPLE 13

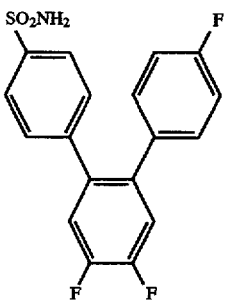

4-[3,4-Difluoro-6-(4-fluorophenyl)phenyl]benzenesulfonamide

Following the general procedure outlined in Synthetic Scheme XI, 2.65 g (7.32 mmol) of 1,2-difluoro-4-(4-fluorophenyl)-5-[4-(methylsulfonyl)phenyl]benzene (the title compound of Example 11) was converted to its corresponding sulfonamide. Purification by silica gel chromatography (Waters LC-2000) with ethyl acetate/hexane (1:3) and subsequent recrystallization from ethyl acetate/hexane gave 1.37 g (52%) of 4-[3,4-difluoro-6-(4-fluorophenyl)phenyl]benzenesulfonamide as a colorless solid: mp 190.2°–191.5° C.; NMR (CDCl$_3$) δ 4.77 (s, 2H), 6.94 (t, J=8 Hz, 2H), 6.98–7.06 (m, 2H), 7.17–7.28 (m, 4H), 7.79 (d, J=8 Hz, 2H). MS (FAB): m/e 370(M+Li); HRMS Calc'd for C$_{18}$H$_{12}$F$_3$NO$_2$S: 363.0541. Found: 363.0576.

Anal. Calc'd for C$_{18}$H$_{12}$F$_3$NO$_2$S: C, 59.50; H, 3.33; N, 3.85. Found: C, 59.52; H, 3.57; N, 3.68.

EXAMPLE 14

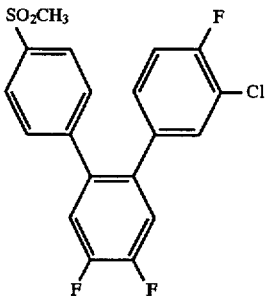

1-(3-Chloro-4-fluorophenyl)-4,5-difluoro-2-[4-(methylsulfonyl)phenyl]benzene

Step 1

Preparation of 1-(3-chloro-4-fluorophenyl)-4,5-difluoro-2-[4-(methylthio)phenyl]benzene Following the general procedure outlined in Synthetic Scheme VII, 4.1 g (15 mmol) of 1,2-dibromo-4,5-difluorobenzene, 3.0 g (18 mmol) of 4-methylthiophenylboronic acid (Example 1, Step 2) and 2.9 g (16.5 mmol) of 3-chloro-4-fluorophenylboronic acid were reacted. Purification by silica gel chromatography gave 3.5 g of 1-(3-chloro-4-fluorophenyl)-4,5-difluoro-2-[4-(methylthio)phenyl]benzene as a semi-solid which was used without further purification.

Step 2

Preparation of 1-(3-chloro-4-fluorophenyl)-4,5-difluoro-2-[4-(methylsulfonyl)phenyl]benzene Following the synthetic procedure outlined in Step 2 of Example 11, 3.50 g (ca. 15 mmol) of crude 1-(3-chloro-4-fluorophenyl)-4,5-difluoro-2-[4-(methylthio)phenyl]benzene (Step 1) was oxidized to its corresponding sulfonamide. Purification by silica gel chromatography (Waters Prep-500A) with ethyl acetate/hexane (1:3) and subsequent recrystallization from ethyl acetate/hexane gave 1.66 g (28%) of 1-(3-Chloro-4-fluorophenyl)-4,5-difluoro-2-[4-(methylsulfonyl)phenyl]benzene as a colorless solid: mp 172.2°–172.5° C.; NMR (CDCl$_3$) δ 3.05 (s, 3H), 6.82–6.89 (m, 1H), 6.99 (t, J=9 Hz, 1H), 7.14 (dd, J=2, 8 Hz, 1H), 7.20–7.32 (m, 4H), 7.84(d, J=8 Hz, 2H); MS (EI): m/e (rel intensity) 396-(22), 317 (12), 282-(100), 262 (25), 243-(10); HRMS Calc'd for C$_{19}$H$_{12}$Cl F$_3$O$_2$S: 396.0199.

Found: 396.0203. Anal. Calc'd for C$_{19}$H$_{12}$ClF$_3$O$_2$S: C, 57.51; H, 3.05; F, 14.36. Found: C, 57.31; H, 2.99; F, 14.48.

EXAMPLE 15

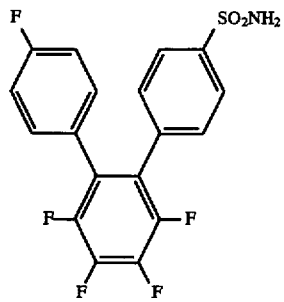

4-[2,3,4,5-Tetrafluoro-6-(4-fluorophenyl)phenyl]benzenesulfonamide

Step 1

Preparation of 1,2,3,4-tetrafluoro-5-(4-fluorophenyl)-6-[4-(methylthio)phenyl]benzene Under nitrogen, 1 g of Pd(PPh$_3$)$_4$ was added to a stirred solution of 4.85 g (15.8 mmol) of 1,2-dibromo-3,4,5,6-tetrafluorobenzene (Aldrich), 2.65 g (18.9 mmol) of 4-fluorophenylboronic acid, and 3.17 g (18.9 mmol) of 4-methylthiophenylboronic acid (Example 1, Step 2) in 80 mL of toluene, 50 mL of ethanol, and 35 mL of 2M Na$_2$CO$_3$. After vigorous stirring at reflux overnight, the solvent was removed in vacuo. The residue was dissolved in ethyl acetate, washed water, and dried over Na$_2$SO$_4$. Concentration in vacuo gave 7.3 g of 1,2,3,4-tetrafluoro-5-(4-fluorophenyl)-6-[4-(methylthio)phenyl]benzene as a yellow oil which was used without further purification.

Step 2

Preparation of 1,2,3,4-tetrafluoro-5-(4-fluorophenyl)-6-[4-(methylsulfonyl)phenyl]benzene To a stirred solution of 7.3 g of crude 1,2,3,4-tetrafluoro-5-(4-fluorophenyl)-6-[4-(methylthio)phenyl]benzene (Step 1) in 40 mL of methylene chloride was slowly added 15 g (43.5 mmol) of 3-chloroperoxybenzoic acid (ca 55%) at -10° C. Purification by silica gel chromatography (MPLC) with ethyl acetate/hexane (1:5) followed by reversed phase chromatography (Waters DeltaPrep-3000) with acetonitrile/water/TFA (48:52:0.05) gave 1.2 g (19% overall for both steps) of 1,2,3,4-tetrafluoro-5-(4-fluorophenyl)-6-[4-(methylsulfonyl)phenyl]benzene as a colorless solid:

mp 134.0°–135.0° C.; NMR (CDCl$_3$) δ 3.05 (s, 3H), 6.91–7.03 (m, 4H), 7.26(d, J=8.5 Hz, 2H), 7.84(d, J=8.5 Hz,

2H). MS (FAB): m/e 405 (M+Li); HRMS Calc'd for C$_{19}$H$_{11}$F$_5$O$_2$S: 398.0400, found: 398.0393.

Step 3

Preparation of 4-[2,3,4,5-tetrafluoro-6-(4-fluorophenyl)phenyl]benzenesulfonamide Following the general procedure outlined in Synthetic Scheme XI, 1.1 g (2.76 mmol) of 1,2,3,4-tetrafluoro-5 (4-fluorophenyl)-6-[4-(methylsulfonyl)phenyl]benzene (Step 2) was converted to its corresponding sulfonamide. Purification by silica gel chromatography (MPLC) with ethyl acetate/hexane (1:5) gave 80 mg (7%) 4-[2,3,4,5-tetrafluoro-6-(4-fluorophenyl)phenyl]benzenesulfonamide as a colorless solid: mp 202.0°–203.0° C.; NMR (CDCl$_3$) δ 4.78 (br s, 2H), 6.92–7.04 (m, 4H), 7.21(d, J=8.5 Hz, 2H), 7.82(d, J=8.5 Hz, 2H). MS (FAB): m/e 406 (M+Li). Anal. Calc'd for C$_{18}$H$_{10}$F$_5$NO$_2$S. (0.16 H$_2$O): C, 53.76; H, 2.59; N, 3.48. Found: C, 53.73; H, 2.40; N, 3.44.

EXAMPLE 16

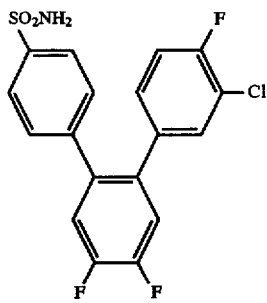

4-[2-(3-Chloro-4-fluorophenyl)-4,5-difluorophenyl]benzenesulfonamide

Following the general procedure outlined in Synthetic Scheme XI, 2.00 g (5.04 mmol) of 1-(3-chloro-4-fluorophenyl)-4,5-difluoro-2-[4-(methylsulfonyl)phenyl]benzene (the title compound of Example 14) was converted to its corresponding sulfonamide. Purification by reverse phase chromatography (Waters DeltaPrep-3000) with acetonitrile/water/TFA (48:52:0.05) and subsequent recrystallization from ethyl acetate/hexane gave 500 mg (25%) of 4-[2-(3-chloro-4-fluorophenyl)-4,5-difluorophenyl] benzenesulfonamide as a colorless solid: mp 162.5°–162.8° C.; NMR (CDCl$_3$) δ 4.80 (s, 2H), 6.81–6.88 (m, 1H), 6.99 (t, J=9 Hz, 1H), 7.15–7.28 (m, 5H), 7.83(d, J=8 Hz, 2H). MS (FAB): m/e 404 (M+Li); HRMS Calc'd for C$_{18}$H$_{11}$ClF$_3$NO$_2$S: 397.0151. Found: 397.0152. Anal. Calc'd for C$_{18}$H$_{11}$ClF$_3$NO$_2$S: C, 54.35; H, 2.79; N, 3.52. Found: C, 54.57; H, 3.00; N, 3.42.

EXAMPLE 17

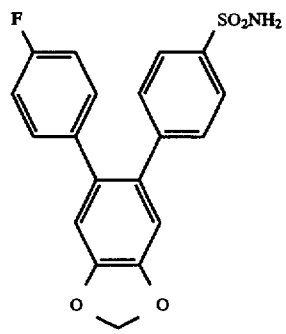

5-(4-Fluorophenyl)-6-[4-(methylsulfonyl)phenyl]-1,3-benzodioxole

Step 1

5-(4-fluorophenyl)-6-[4-(methylthio)phenyl]-1,3-benzodioxole

Under nitrogen, 1 g of Pd(PPh$_3$)$_4$ was added to a stirred solution of 4 g (14.3 mmol) of 5,6-dibromo-1,3-benzodioxole (Lancaster), 2.4 g (17.2 mmol) of 4-fluorophenyl boronic acid, and 2.87 g (17.2 mmol) of 4-methylthiophenylboronic acid (Example 1, Step 2) in 70 mL of toluene, 40 mL of ethanol, and 30 mL of 2M Na$_2$CO$_3$. After vigorous stirring at reflux overnight, the solvent was removed in vacuo. The residue was dissolved in ethyl acetate, washed with water, and dried over Na$_2$SO$_4$. Concentration in vacuo gave 6.9 g of 5-(4-fluorophenyl)-6-[4-(methylthio)phenyl]-1,3-benzodioxole as a semi-solid which was used without further purification.

Step 2

Preparation of 5-(4-fluorophenyl)-6-[4-(methylsulfonyl)phenyl]-1,3-benzodioxole

To a stirred solution of 6.9 g of 5-(4-fluorophenyl)-6-[4-(methylthio)phenyl]-1,3-benzodioxole (Step 1) in 30 mL of methylene chloride was slowly added 12 g (38.2 mmol) of 3-chloroperoxybenzoic acid (ca. 55%) at −10° C. Purification by silica gel chromatography (MPLC) with ethyl acetate/hexane (1:4) followed by reversed phase chromatography (Waters DeltaPrep-3000) with acetonitrile/water/ TFA (45:55:0.05) gave 200 mg (4% overall for both steps) of 5-(4-fluorophenyl)-6-[4-(methylsulfonyl)phenyl]-1,3-benzodioxole as a colorless solid: mp 173.0°–174.0° C.; NMR (CDCl$_3$) δ 3.04 (s, 3H), 6.06 (s, 2H), 6.86–6.92 (m, 4H), 6.96–7.03 (m, 2H), 7.23–7.27 (m, 2H), 7.76(d, J=8.5 Hz, 2H). MS (FAB): m/e 377 (M+Li); HRMS Calc'd for C$_{20}$H$_{15}$FO$_4$S: 370.0675, found: 370.0680. Anal. Calc'd for C$_{20}$H$_{15}$FO$_4$S (0.25 H$_2$O): C, 64.08; H, 4.17. Found: C, 64.08; H, 4.15.

EXAMPLE 18

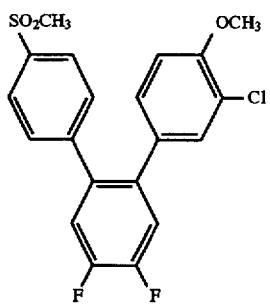

1-(3-Chloro-4-methoxyphenyl)-4,5-difluoro-2-[4-(methylsulfonyl)phenyl]benzene

Step 1

Preparation of 1-bromo-4,5-difluoro-2-[4-(methylthio)phenyl]benzene

Following the general procedure outlined in Synthetic Scheme IV, 40 g (147 mmol) of 1,2-dibromo-4,5-difluorobenzene was reacted with 12.3 g (73 mmol) of 4-methylthiophenylboronic acid (Example 1, Step 2). Purification by silica gel chromatography with hexane gave 40.3 g of 1-bromo-4,5-difluoro-2-[4-(methylthio)phenyl]benzene as a yellow oil which was used without further purification.

Step 2

Preparation of 1-bromo-4,5-difluoro-2-[4-(methylsulfonyl)phenyl]benzene

Following the synthetic procedure outlined in Step 4 of Example 1, 40.3 g (ca. 73 mmol) of 1-bromo-4,5-difluoro-2-[4-(methylthio)phenyl]benzene (Step 1) was oxidized to its corresponding sulfone. Purification by silica gel chromatography (Waters Prep-500A) with ethyl acetate/hexane (1,3) gave 17.4 g (68%) of 1-bromo-4,5-difluoro-2-[4-(methylsulfonyl)phenyl]benzene as a colorless solid: mp 158.5°–159.5° C.; NMR (CDCl$_3$) δ 3.12 (s, 3H), 7.13–7.21 (m, 1H), 7.50–7.60 (m, 3H), 8.02(d, J=9 Hz, 2H).

Step 3

Preparation of 1-(3-chloro-4-methoxyphenyl)-4,5-difluoro-2-[4-(methylsulfonyl)phenyl]benzene Following the general procedure outlined in Synthetic Scheme VI, 4.4 g (13 mmol) of 1-bromo-4,5-difluoro-2-[4-(methylsulfonyl)phenyl]benzene (Step 2) was reacted with 3.1 g (17 mmol) of 3-chloro-4-methoxy phenylboronic acid (Example 5, Step 2). Purification by silica gel chromatography (Waters Prep-500A) with ethyl acetate/hexane (3:7) and subsequent recrystallization from ethyl acetate/hexane gave 4.47 g (95%) of 1-(3-chloro-4-methoxyphenyl)-4,5-difluoro-2-[4-(methylsulfonyl)phenyl]benzene as a colorless solid: mp 147.5°–148.5° C.; NMR (CDCl$_3$) δ 3.05 (s, 3H), 3.88 (s, 3H), 6.75(d, J=9 Hz, 1H), 6.83 (dd, J=2, 9 Hz, 1H), 7.10(d, J=2 Hz, 1H), 7.17–7.32 (m, 4H), 7.83(d, J=9 Hz, 2H). MS (EI): m/e (rel intensity) 408 (33), 314 (15), 294 (52), 279 (63), 251 (100). Anal. Calc'd for C$_{20}$H$_{15}$ClF$_2$O$_3$S (0.27 ethyl acetate): C, 58.53; H, 3.99; F, 8.79. Found: C, 58.75; H, 3.71; F, 8.52.

EXAMPLE 19

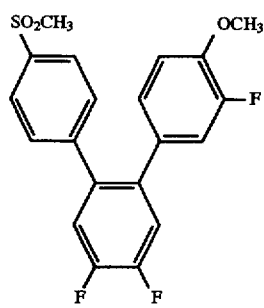

1,2-Difluoro-4-(3-fluoro-4-methoxyphenyl)-5-[4-(methylsulfonyl)phenyl]benzene

Following the general procedure outlined in Synthetic Scheme VI, 3.0 g (8.6 mmol) of 1-bromo-4,5-difluoro-2-[4-(methylsulfonyl)phenyl]benzene (Example 18, Step 2) was reacted with 1.9 g (11 mmol) of 3-fluoro-4-methoxyphenylboronic acid (Example 4, Step 3). Purification by silica gel chromatography (Waters Prep500A) with ethyl acetate/hexane (1:3) and subsequent recrystallization from ethyl acetate/hexane gave 3.19 g (94%) of 1,2-difluoro-4-(3-fluoro-4-methoxyphenyl)-[benzene as a chloroethylsulfonyl)phenyl]benzene as a colorless solid: mp 159.2°–159.7° C.; NMR (CDCl$_3$) δ 3.05 (s, 3H), 3.87 (s, 3H), 6.63–6.85 (m, 3H), 7.16–7.32 (m, 4H), 7.82(d, J=8 Hz, 2H). MS (EI): m/e (rel intensity) 392 (49), 313 (15), 298 (48), 269 (100), 249 (79). Anal. Calc'd for C$_{20}$H$_{15}$F$_3$O$_3$S (0.26 ethyl acetate): C, 60.85; H, 4.15; F, 13.71. Found: C, 61.33; H, 3.90; F, 13.40.

EXAMPLE 20

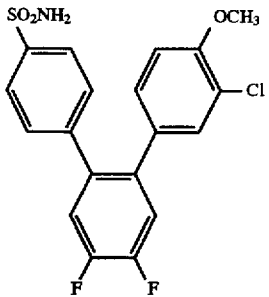

4-[2-(3-Chloro-4-methoxyphenyl)-4,5-difluorophenyl]benzenesulfonamide

Following the general procedure outlined in Synthetic Scheme XI, 4.00 g (9.78 mmol) of 1-(3-chloro-4-methoxyphenyl)-4,5-difluoro-2-[4-(methylsulfonyl)phenyl]benzene (the title compound of Example 18) was converted to its corresponding sulfonamide. Purification by silica gel chromatography (HPLC) with ethyl acetate/hexane (1:3) and subsequent recrystallization from ethyl acetate/hexane gave 0.86 g (21%) of 4-[2-(3-chloro-4-methoxyphenyl)-4,5-difluorophenyl]benzenesulfonamide as a colorless solid: mp 70° C. (dec); NHR (CDCl$_3$) δ 3.87 (s, 3H), 4.84 (s, 2H), 6.75(d, J=9 Hz, 1H), 6.82 (dd, J=2, 9 Hz, 1H), 7.14(d, J=2 Hz, 1H), 7.16–7.28 (m, 4H), 7.81 (d, J=8, 2H). MS (EI): m/e (rel intensity) 409 (22), 294 (15), 279 (28), 251 (100), 231 (20). Anal. Calc'd for C$_{19}$H$_{14}$ClF$_2$NO$_3$S: C, 55.68; H, 3.44; N, 3.42. Found: C, 55.42; H, 3.48; N, 3.33.

EXAMPLE 21

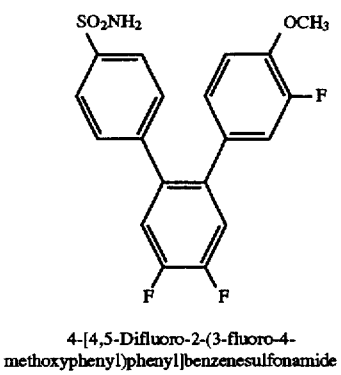

4-[4,5-Difluoro-2-(3-fluoro-4-methoxyphenyl)phenyl]benzenesulfonamide

Following the general procedure outlined in Synthetic Scheme XI; 2.50 g (6.38 mmol) of 1,2-difluoro-4-(3-fluoro-4-methoxyphenyl)-5-[4-(methylsulfonyl)phenyl]benzene (the title compound of Example 19) was converted to its corresponding sulfonamide. Purification by silica gel chromatography (MPLC) with ethyl acetate/hexane (1:3) and subsequent recrystallization from ethyl acetate/hexane gave 0.82 g (33%) of 4-[4,5-difluoro-2-(3-fluoro-4-methoxyphenyl)phenyl]benzenesulfonamide as a colorless solid: mp 132.2°–132.8° C.; NMR (CDCl$_3$) δ 3.87 (s, 3H), 4.85 (s, 2H), 6.71–6.85 (m, 3H), 7.15–7.27 (m, 4H), 7.81(d, J=9 Hz, 2H). MS (EI): m/e (rel intensity) 393(32), 298 (21), 282 (25), 269 (100), 249 (46). Anal. Calc'd for $C_{19}H_{14}F_3NO_3S$: C, 58.01; H, 3.59; N, 3.56. Found: C, 57.75; H, 3.48; N, 3.48.

EXAMPLE 22

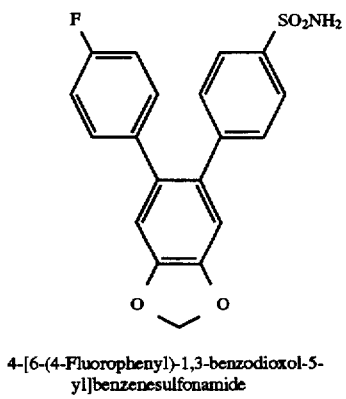

4-[6-(4-Fluorophenyl)-1,3-benzodioxol-5-yl]benzenesulfonamide

Step 1

Preparation of 5-bromo-6-(4-fluorophenyl)-1,3-benzodioxole

Under nitrogen, 1.1 g of Pd(PPh$_3$)$_4$ was added to a stirred solution of 10.4 g (37.2 mmol) of 5,6-dibromo-1,3-benzodioxole and 2.6 g (18.6 mmol) of 4-fluorophenylboronic acid in 100 mL of toluene, 60 mL of ethanol, and 40 mL of M Na$_2$CO$_3$. After vigorous stirring at reflux overnight, the solvent was removed in vacuo. The residue was dissolved in ethyl acetate, washed with water, and dried over Na$_2$SO$_4$. Purification by silica gel chromatography (Waters Prep-500A) with hexane as the eluent gave 3.9 g (71%) of 5-bromo-6 (4-fluorophenyl)-1,3-benzodioxole as a colorless solid: mp 86.0°–87.5° C.; NMR (CDCl$_3$) δ 6.02 (s, H), 6.77 (s, 1H), 7.04–7.13 (m, 3H), 7.28–7.35 (m, 2H).

Step 2

Preparation of [6 (4-fluorophenyl)-1,3-benzodioxol-5-yl]boronic acid

Under nitrogen, 6.3 mL (15.8 mmol) of n-BuLi (2.5M in hexanes) was added to a stirred solution of 3.9 g (13.2 mmol) of 5-bromo-6-(4-fluorophenyl)-1,3-benzodioxole (Step 1) in 30 mL of anhydrous THF at −78° C. After 30 minutes, 4.5 mL (39.4 mmol) of trimethylborate was added. The reaction was warmed to ambient temperature and stirred for 3 hours prior to the addition of 60 mL of 5% NaOH. The reaction was stirred for an additional 60 minutes, the THF removed in vacuo, and the pH adjusted to ca. 4. The residue was dissolved in ethyl acetate; the resulting solution was dried over Na$_2$SO4 and concentrated in vacuo to give 1.7 g (50%) of [6 (4-fluorophenyl)-1,3-benzodioxol-5-yl] boronic acid as a pale yellow solid: NMR (CDCl$_3$) δ 4.00 (br s, 2H), 6.06 (s, 2H), 6.75 (s, 1H), 7.08–7.17 (m, 2H), 7.26 (s, 1H), 7.31–7.39 (m, 2H).

Step 3

Preparation of 4-[6 (4-fluorophenyl)-1,3-benzodioxol-5-yl]benzenesulfonamide

Under nitrogen, 500 mg of Pd(PPh$_3$)$_4$ was added to a stirred solution of 1.55 g (6.0 mmol) of [6-(4-fluorophenyl)-1,3-benzodioxol-5-yl]boronic acid (Step 2) and 1.09 g (4.62 mmol)of 4-bromobenzenesulfonamide (Lancaster) in 30 mL of toluene, 20 mL of ethanol, and 15 mL of 2M Na$_2$CO$_3$. After vigorous stirring at reflux for 6hours, the solvent was removed in vacuo and the residue dissolved in ethyl acetate. The resulting solution was washed with water and dried over Na$_2$SO$_4$. Purification by silica gel chromatography (MPLC) with ethyl acetate/hexane (3:7) gave 1.3 g (76%) of 4-[6-(4-fluorophenyl)-1,3-benzodioxol-5-yl]benzenesulfonamide as a colorless solid: mp 191.0°–192.5° C.; NMR (CDCl$_3$) δ 4.80 (s, 2H), 6.06 (s, 2H), 6.83–6.92 (m, 4H), 6.97–7.06 (m, 2H), 7.20(d, J=8.5 Hz, 2H), 7.74(d, J=8.5 Hz, 2H). MS (FAB): m/e 372 (H+H). Anal. Calc'd for $C_{19}H_{14}FNO_4S$: C, 61.45; H, 3.80; N, 3.77. Found: C, 61.48; H, 3.92; N, 3.68.

EXAMPLE 23

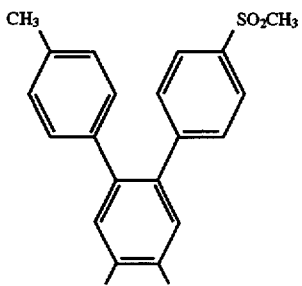

1,2-Difluoro-4-(4-methylphenyl)-5-[4-(methylsulfonyl)phenyl]benzene

Following the general procedure outlined in Synthetic Scheme VI, 2.56 g (7.37 mmol) of 1-bromo-4,5-difluoro-2-[(4-methylsulfonyl)phenyl]benzene (Example 18; Step 2) was reacted with 1.35 g (9.93 mmol) of 4-methylphenylboronic acid. Purification by silica gel chromatography (MPLC) with ethyl acetate/hexane (3:7) gave 2.55 g (97%) of 1,2-difluoro-4-(4-methylphenyl)-5-[4-(methylsulfonyl)phenyl]benzene as a colorless solid: mp 147.0°–148.0° C.; NMR (CDCl₃) δ 2.32 (s, 3H), 3.05 (s, 3H), 6.92(d, J=8 Hz, 2H), 7.03(d, J=8 Hz, 2H), 7.17–7.32(m, 4H), 7.79(d, J=8 Hz, 2H). MS (FAB): m/e 365(M+Li). Anal. Calc'd for C₂₀H₁₆F₂O₂S: C, 67.03; H, 4.50. Found: C, 67.18; H, 4.48.

EXAMPLE 24

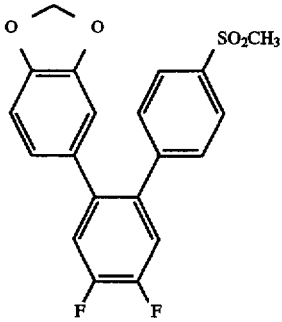

5-[4,5-Difluoro-2-[4-(methylsulfonyl)phenyl]phenyl]-1,3-benzodioxole

Step 1

Preparation of (1,3-benzodioxol-5-yl)boronic acid

Following the synthetic procedure outlined in Step 2 of Example 1, 15.2 g (75.6 mole) of 5-bromo-1,3-benzodioxole (Aldrich) was converted to (1,3-benzodioxol-5-yl)boronic acid as a colorless solid: NMR (CDCl₃) δ 5.98 (s, 2H), 6.88 (t, J=8 Hz, 1H), 7.26–7.41 (m, 2H), 7.80 (br s, 2H).

Step 2

Preparation of 5-[4,5-difluoro-2-[4-(methylsulfonyl) phenyl]phenyl]-1,3-benzodioxole Following the general procedure outlined in Synthetic Scheme I, 2.24 g (6.45 mmol) of 1-bromo-4,5-difluoro-2-[4-(methylsulfonyl)phenyl]benzene (Example 18, Step 2) was reacted with 1.39 g (8.38 mmol) of (1,3-benzodioxol-5-yl)boronic acid (Step 1). Purification by silica gel chromatography (MPLC) with ethyl acetate/hexane (1:4) gave 2.47 g (99%) of 5-[4,5-difluoro-2-[4-(methylsulfonyl) phenyl]phenyl]-1,3-benzodioxole as a colorless solid: mp 110.0°–111.0° C.; NMR (CDCl₃) δ 3.05 (s, 3H), 5.95 (s, 2H), 6.47–6.52 (m, 2H), 6.67(d, J=8.5 Hz, 1H), 7.16–7.24 (m, 2H), 7.32(d, J=8.5 Hz, 2H), 7.82 (d, J=8.5 Hz, 2H). MS (FAB): m/e 395 (M+Li). Anal. Calc'd for C₂₀H₁₄F₂O₄S: C, 61.85; H, 3.63; Found: C, 1.92; H, 3.66.

EXAMPLE 25

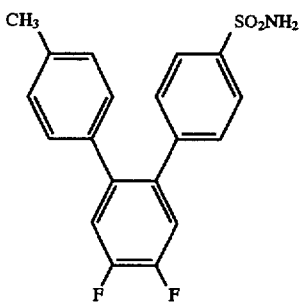

4-[4,5-Difluoro-2-(4-methylphenyl)phenyl]benzenesulfonamide

Following the general procedure outlined in Synthetic Scheme XI, 2.43 g (6.78 mmol) of 1,2-difluoro-4-(4-methylphenyl)-5-[4-(methylsulfonyl)phenyl]benzene (the title compound of Example 23) was converted to its corresponding sulfonamide. Purification by silica gel chromatography (MPLC) with ethyl acetate/hexane (1:5) gave 1.90 g (78%) of 4-[4,5-difluoro-2-(4-methylphenyl)phenyl] benzenesulfonamide as a colorless solid: mp 103.0°–104.0° C.; NMR (CDCl₃) δ 2.32 (s, 3H), 4.81 (s, 2H), 6.93(d, J=8 Hz, 2H), 7.04(d, J=8 Hz, 2H) 7.16–7.29 (m, 4H), 7.78(d, J=8.5 Hz, 2H). MS (EI): m/e 359 (26), 279 (33), 278 (41), 264 (100), 251 (36), 119 (62 , 80(70), 64 (56). Anal. Calc'd for C₁₉H₁₅F₂NO₂S: C, 63.50; H, 4.21; N, 3.90. Found: C, 63.55; H, 4.24; N, 3.80.

EXAMPLE 26

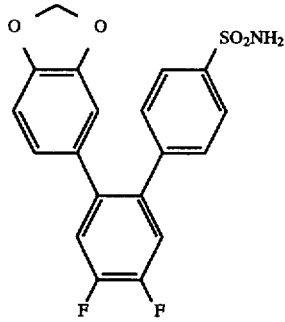

4-[2-(1,3-Benzodioxol-5-yl)-4,5-difluorophenyl]benzenesulfonamide

Following the general procedure outlined in Synthetic Scheme XI, 2.34 g (6.02 mmol) of 5-[4,5-difluoro-2-[4-(methylsulfonyl)phenyl]phenyl]-1,3-benzodioxole (the title compound of Example 24) was converted to its corresponding sulfonamide. Purification by silica gel chromatography (MPLC) with ethyl acetate/hexane (3:7) gave 1.84 g (78%) of 4-[2-(1,3-benzodioxol-5-yl)-4,5-difluorophenyl] benzenesulfonamide as a colorless solid: mp 142.0°–143.0° C.; NMR (CDCl₃) δ 4.83 (s, 2H), 5.95 (s, 2H), 6.49–6.54 (m, 2H), 6.69(d, J=8 Hz, 1H), 7.15–7.30 (m, H), 7.81(d, J=8 Hz, 2H). MS (EI): m/e 389 (18), 308 (14), 251 (100), 231 (43). Anal. Calc'd for C₁₉H₁₃F₂NO₄S.(0.19 H₂O): C, 58.09; H, 3.43; N, 3.57. Found: C, 58.11; H, 3.51; N, 3.48.

EXAMPLE 27

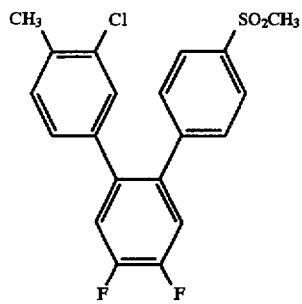

1-(3-Chloro-4-methylphenyl)-4,5-difluoro-2-[4-(methylsulfonyl)phenyl]benzene

Step 1

Preparation of 3-chloro-4-methylphenylboronic acid

Following the general procedure outlined in Synthetic Scheme I, 11.1 g (54 mmol) of 4-bromo-2-chlorotoluene was converted to 3-chloro-4-methylphenylboronic acid as a colorless solid: NMR (CDCl$_3$) δ 2.47 (s, 3H), 7.37(d, J=8 Hz, 1H), 7.98 (d, J=8 Hz, 1H), 8.08 (s, 1H).

Step 2

Preparation of 1-(3-chloro-4-methylphenyl)-4,5-difluoro-2-[4-(methylsulfonyl)phenyl]benzene Following the general procedure outlined in Synthetic Scheme VI, 2.49 g (7.17 mmol) of 1-bromo-4,5-difluoro-2-[4-(methylsulfonyl)phenyl]benzene (Example 18, Step 2) was reacted with 1.59 g (9.33 mmol) of 3-chloro-4-methylphenylboronic acid (Step 1). Purification by silica gel chromatography (HPLC) with ethyl acetate/hexane (1:5) gave 2.65 g (94%) of 1-(3-chloro-4-methylphenyl)-4,5-difluoro-2-[4-(methylsulfonyl)phenyl]benzene as a colorless solid: mp 138.0°–139.0° C.; NMR (CDCl$_3$) δ 2.34 (s, 3H), 3.05 (s, 3H), 6.75 (dd, J=2, 8 Hz, 1H), 7.03–7.10 (m, 2H), 7.18–7.26 (m, 2H), 7.29 (d, J=8 Hz, 2H), 7.83 (d, J=8 Hz, 2H). MS (FAB): m/e 399 (M+Li). Anal. Calc'd for C$_{20}$H$_{15}$ClF$_2$O$_2$S: C, 61.15; H, 3.85. Found: C, 61.12; H, 3.82.

EXAMPLE 28

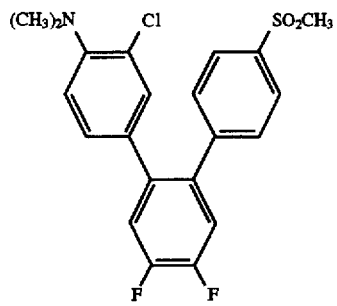

2-Chloro-4-[4,5-difluoro-2-[4-(methylsulfonyl)phenyl]phenyl]-N,N-dimethylbenzenamine

Step 1

Preparation of 4-bromo-2-chloro-N,N-dimethylaniline

Under nitrogen, 11.6 mL (186 mmol) of iodomethane was added to a stirred solution of 12.8 g (62 mmol) of 4-bromo-2-chloroaniline and 42.8 g (310 mmol) of powdered K$_2$CO$_3$ in 200 mL of DMF. Purification by silica gel chromatography (Waters Prep-500A)with ethyl acetate/hexane (5:95) gave 11.3 g (78%) of 4-bromo-2-chloro-N,N-dimethylaniline as a colorless liquid: NMR (CDCl$_3$) δ 2.79 (s, 6H), 6.92(d, J=9 Hz, 1H), 7.25–7.34 (m, 1H), 7.49 (d, J=2 Hz, 1H).

Step 2

Preparation of 3-chloro-4-(N,N-dimethylamino)phenylboronic acid

Following the general procedure outlined in Synthetic Scheme I, 11.3 g (48.2 mmol) of 4-bromo-2-chloro-N,N-dimethylaniline (Step 1) was converted to 3-chloro-4-(N,N-dimethylamino)phenylboronic acid as a colorless solid: NMR (CDCl$_3$) δ 2.93 (s, 6H), 7.12 (d, J=8 Hz, 1H), 8.01 (d, J=8 Hz, 1H), 8.12 (s, 1H).

Step 3

Preparation of 2-chloro-4-[4,5-difluoro-2-[4-(methylsulfonyl) phenyl][phenyl]-N,N-dimethylbenzenamine Following the general procedure outlined in Synthetic Scheme VI, 2.25 g (6.48 mmol) of 1-bromo-4,5-difluoro-2-[4-(methylsulfonyl)phenyl]benzene (Example 18, Step 2) was reacted with 1.68 g (8.42 mmol) of 3-chloro-4-(N,N-dimethylamino)phenylboronic acid (Step 2). Purification by silica gel chromatography (MPLC) with ethyl acetate/ hexane (3:7) gave 2.65 g (97%) of 2-chloro-4-[4,5-difluoro-2-[4-(methylsulfonyl)phenyl]phenyl]-N,N-dimethylbenzenamine as a colorless solid: mp 129.0°–130.0° C.; NMR (CDCl$_3$) β 2.81 (s, 6H), 3.05 (s, 3H), 6.76–6.91 (m, 2H), 7.08(d, J=2 Hz, 1H), 7.17–7.26 (m, 2H), 7.31 (d, J=8.5 Hz, 2H), 7.83(d, J=8.5 Hz, 2H). MS (FAB): m/e 428 (M+Li). Anal. Calc'd for C$_{21}$H$_{18}$ClF$_2$NO$_2$S: C, 59.79; H, 4.30; N, 3.32. Found: C, 59.40; H, 4.29; N, 3.24.

EXAMPLE 29

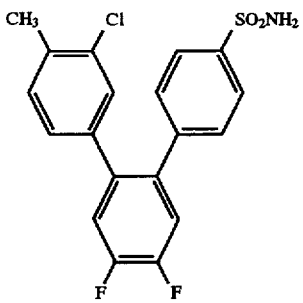

4-[2-(3-Chloro-4-methylphenyl)-4,5-difluorophenyl]benzenesulfonamide

Following the general procedure outlined in Synthetic Scheme XI, 2.54 g (6.47 mmol) of 1-(3-chloro-4-methylphenyl)-4,5-difluoro-2-[4-(methylsulfonyl)phenyl]benzene (the title compound of Example 27) was converted to its corresponding sulfonamide. Purification by silica gel chromatography (MPLC) with ethyl acetate/hexane (1:5) gave 1.80 g (71%) of 4-[2-(3-chloro-4-methylphenyl)-4,5-difluorophenyl]benzenesulfonamide as a colorless solid: mp 139.0°–140.0° C.; NMR (CDCl$_3$) δ 2.33 (s, 3H), 4.81 (s, stopped after ten minutes at 37° C./room temperature by transferring 40 μl of reaction mix into 160 μl ELISA buffer and 25 μM indomethacin. The PGE$_2$ formed was measured by standard ELISA technology (Cayman Chemical). Results are shown in Table II.

TABLE II

| Example | Human COX II ID$_{50}$ μM | Human COX I ID$_{50}$ μM |
|---|---|---|
| 1 | .3 | >100 |
| 2 | <.1 | 19 |
| 3 | <.1 | 3.9 |
| 4 | >100 | >100 |
| 5 | 11.4 | >100 |
| 6 | <.1 | 13.1 |
| 7 | <.1 | 8.2 |
| 8 | .1 | >100 |
| 9 | 2.8 | 32.6 |
| 10 | .4 | >100 |
| 11 | <.1 | >100 |
| 12 | <.1 | 9.2 |
| 13 | <.1 | 5.7 |
| 14 | <.1 | >100 |
| 15 | 7.2 | >100 |
| 16 | <.1 | 5.5 |
| 17 | <.1 | >100 |
| 18 | <.1 | >100 |
| 19 | <.1 | >100 |
| 20 | <.1 | 18.9 |
| 21 | <.1 | 22.5 |
| 22 | <.1 | 5.3 |
| 23 | <.1 | >100 |
| 24 | <.1 | >100 |
| 25 | <.1 | 17.0 |
| 26 | <.1 | 1.7 |
| 27 | <.1 | >100 |
| 28 | <.1 | >100 |
| 29 | <.1 | 16.5 |
| 30 | <.1 | .6 |

Also embraced within this invention is a class of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. The compounds and composition mayi for example; be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline; dextrose or water may be used as a suitable carrier.

The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredient in the range of about 0.1 to 2000 mg, preferably in the range of about 0.5 to 500 mg and most preferably between about 1 and 100 mg. A daily dose of about 0.01 to 100 mg/kg body weight, preferably between about 0.1 and about 50 mg/kg body weight and most preferably from about 1 to 20 mg/kg body weight, may be appropriate. The daily dose can be administered in one to four doses per day.

For therapeutic purposes, the compounds of this invention are ordinarily combined with one or more adjuvants appropriate to the indicated route of administration. If administered per os, the compounds may be admixed with lactose, sucrose; starch powder, cellulose esters of alkanoic acids, cellulose alkyl esters, talc, stearic acid, magnesium stearate; magnesium oxide, sodium and calcium salts of phosphoric and sulfuric acids, gelatin, acacia gum, sodium alginate, polyvinylpyrrolidone; and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A compound of Formula I

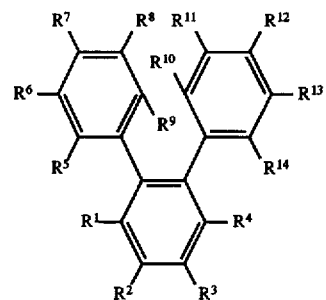

wherein each of R$^1$ through R$^4$ is independently selected from the group consisting of hydrido, halo, and alkoxy; wherein each of R$^5$ through R$^{14}$ is independently selected from the group consisting of hydrido, alkyl, halo, alkoxy, alkylthio, cyano, haloalkyl, amino, alkylamino, dialkylamino, haloalkoxy, hydroxyalkyl, alkoxyalkyl, hydroxyl, mercapto, aminosulfonyl and alkylsulfonyl; provided R$^{12}$ is selected from the group consisting of methylsulfonyl or aminosulfonyl; or a pharmaceutically-acceptable salt thereof.

2H), 6.74 (dd, J=2; 8 Hz, 1H), 7.04 (d, J=8 Hz, 1H), 7.12(d, J=2 Hz, 1H), 7.17–7.25 (m, 4H), 7.80(d, J=8 Hz, 2H). MS (FAB): m/e 400(M+Li). Anal. Calc'd for $C_{19}H_{14}F_2ClNO_2S$: C, 57.95; H, 3.58; N, 3.56.

Found: C, 57.91; H, 3.55; N, 3.54.

EXAMPLE 30

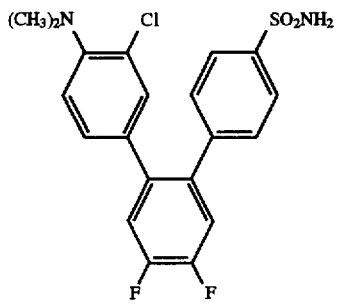

4-[2-[3-Chloro-4-(N,N-dimethylamino)phenyl]-4,5-difluorophenyl]benzenesulfonamide Following the general procedure outlined in Synthetic Scheme XI, 2.50 g (5.93 mmol) of 2-chloro-4-[4,5-difluoro-2-[4-(methylsulfonyl) phenyl]phenyl]-N,N-dimethylbenzenamine (the title compound of Example 28) was converted to its corresponding sulfonamide. Purification by silica gel chromatography (MPLC) with ethyl acetate/hexane (3:7) gave 1.75 g (70%) of 4-[2-[3-chloro-4-(N,N-dimethylamino)phenyl]-4,5-difluorophenyl] benzenesulfonamide as a colorless solid: mp 193.0°–194.0° C.; NMR ($CDCl_3$) δ 2.83 (s, 6H), 4.80 (s, 2H), 6.79 (dd, J=2, 9 Hz, 1H), 6.87–6.95 (m, 1H), 7.13(d, J=2 Hz, 1H), 7.17–7.29 (m, 4H), 7.82(d, J=8 Hz, 2H). MS (0.27 $H_2O$): C, 56.16; H, 4.13; N, 6.55. Found: C, 56.16; H, 4.02; N, 6.39.

BIOLOGICAL EVALUATION
Rat Carrageenan Foot Pad Edema Test

The carrageenan foot edema test was performed with materials, reagents and procedures essentially as described by Winter, et al., (*Proc. Sec. Exp. Biol. Med.*, 111, 544 (1962)). Male Sprague-Dawley rats were selected in each group so that the average body weight was as close as possible. Rats were fasted with free access to water for over sixteen hours prior to the test. The rats were dosed orally (1 mL) with compounds suspended in vehicle containing 0.5% methylcellulose and 0.025% surfactant, or with vehicle alone. One hour later a supplanter injection of 0.1 mL of 1% solution of carrageenan/sterile 0.9% saline was administered and the volume of the injected foot was measured with a displacement plethysmometer connected to a pressure transducer with a digital indicator. Three hours after the injection of the carrageenan, the volume of the foot was again measured. The average foot swelling in a group of drug-treated animals was compared with that of a group of placebo-treated animals and the percentage inhibition of edema was determined (Otterness and Bliven, *Laboratory Models for Testing NSAIDs*, in Non-steroidal Anti-Inflammatory Drugs, (J. Lombardino, ed. 1985)). The % inhibition shows the % decrease from control paw volume determined in this procedure and the data for selected compounds in this invention are summarized in Table I.

Rat Carrageenan-induced Analgesia Test

The analgesia test using rat carrageenan was performed with materials, reagents and procedures essentially as described by Hargreaves, et al., (*Pain*, 32, 77 (1988)). Male Sprague-Dawley rats were treated as previously described for the Carrageenan Foot Pad Edema test. Three hours after the injection of the carrageenan, the rats were placed in a special plexiglass container with a transparent floor having a high intensity lamp as a radiant heat source; positionable under the floor. After an initial twenty minute period, thermal stimulation was begun on either the injected foot or on the contralateral uninjected foot. A photoelectric cell turned off the lamp and timer when light was interrupted by paw withdrawal. The time until the rat withdraws its foot was then measured. The withdrawal latency in seconds was determined for the control and drug-treated groups, and percent inhibition of the hyperalgesic foot withdrawal determined. Results are shown in Table I.

TABLE I

| Examples | RAT PAW EDEMA % Inhibition @ 10 mg/kg body weight | ANALGESIA % Inhibition @ 30 mg/kg body weight |
|---|---|---|
| 1 | 26 | ND |
| 2 | 6 | 28 |
| 3 | 14 | 1 |
| 20 | 19 | 22* |

*Assay performed at 50 mg/kg body weight

Evaluation of COX I and COX II Activity In Vitro

The compounds of this invention exhibited inhibition in vitro of COX II. The COX II inhibition activity of the compounds of this invention illustrated in the Examples was determined by the following methods.

a. Preparation of Recombinant COX Baculoviruses

A 2.0 kb fragment containing the coding region of either human or murine COX-I or human or murine COX-II was cloned into a BamH1 site of the baculovirus transfer vector pVL1393-(Invitrogen) to generate the baculovirus transfer vectors for COX-I and COX-II in a manner similar to the method of D. R. O'Reilly et al (*Baculovirus Expression Vectors: A Laboratory Manual* (1992)). Recombinant baculoviruses were isolated by transfecting 4 µg of baculovirus transfer vector DNA into SF9 insect cells (2×10e8) along with 200 ng of linearized baculovirus plasmid DNA by the calcium phosphate method. See M.D. Summers and G. E. Smith, *A Manual of Methods for Baculovirus Vectors and Insect Cell Culture Procedures*, Texas Agric. Exp. Station Bull. 1555 (1987). Recombinant viruses were purified by three rounds of plaque purification and high titer (10E7–10E8 pfu/ml) stocks of virus were prepared. For large scale production, SF9 insect cells were infected in 10 liter fermentors (0.5×10⁶/ml) with the recombinant baculovirus stock such that the multiplicity of infection was 0.1. After 72 hours the cells were centrifuged and the cell pellet homogenized in Tris/Sucrose (50 mM: 25%, pH 8.0) containing 1% 3-[(3-cholamidopropyl)dimethylammonio]-1-propanesulfonate (CHAPS). The homogenate was centrifuged at 10,000×G for 30 minutes, and the resultant supernatant was stored at −80° C. before being assayed for COX activity.

b. Assay for COX I and COX II activity:

COX activity was assayed as $PGE_2$ formed/µg protein/time using an ELISA to detect the prostaglandin released. CHAPS-solubilized insect cell membranes containing the appropriate COX enzyme were incubated in a potassium phosphate buffer (50 mM, pH 8.0) containing epinephrine, phenol, and heme with the addition of arachidonic acid (10 µM). Compounds were pre-incubated with the enzyme for 10–20 minutes prior to the addition of arachidonic acid. Any reaction between the arachidonic acid and the enzyme was 2. A compound of Formula I

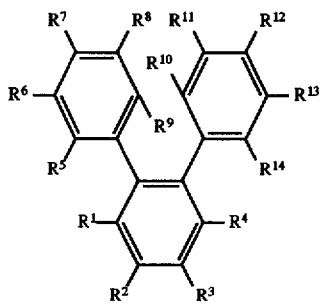

wherein each of $R^1$ through $R^4$ is independently selected from the group consisting of hydrido and halo; or wherein $R^2$ and $R^3$ together form —OCH$_2$O—; wherein each of $R^5$ through $R^8$ is independently selected from the group consisting of hydrido, lower alkyl, halo, lower alkoxy, lower haloalkyl, and lower dialkylamino; or wherein $R^6$ and $R^7$ together form —OCH$_2$O—; wherein $R^{10}$, $R^{11}$, $R^{13}$ and $R^{14}$ are hydrido; and wherein $R^{12}$ is selected from the group consisting of aminosulfonyl and methylsulfonyl; or a pharmaceutically-acceptable salt thereof.

3. A pharmaceutical composition comprising a therapeutically-effective amount of a compound and a pharmaceutically-acceptable carrier or diluent, said compound selected from a family of compounds of Formula I

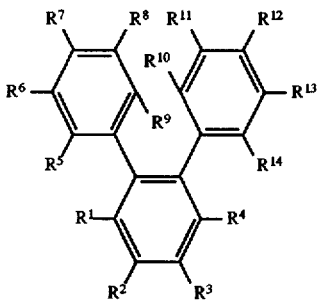

wherein each of $R^1$ through $R^4$ is independently selected from the group consisting of hydrido and halo; or wherein $R^2$ and R together form —OCH$_2$O—; wherein each of $R^5$ through $R^8$ is independently selected from the group consisting of hydrido, lower alkyl, halo, lower alkoxy, lower haloalkyl, and lower dialkylamino; or wherein $R^6$ and $R^7$ together form —OCH$_2$O—; wherein $R^{10}$, $R^{11}$, $R^{13}$ and $R^{14}$ are hydrido; and wherein $R^{12}$ is selected from the group consisting of aminosulfonyl and methylsulfonyl; or a pharmaceutically-acceptable salt thereof.

4. Compound of claim 2 wherein each of $R^1$ through $R^4$ is independently selected from the group consisting of hydrido and halo; or wherein $R^2$ and $R^3$ together form —OCH$_2$O—; wherein each of $R^5$ and $R^9$ is hydrido; wherein each of $R^6$ through $R^8$ is independently selected from the group consisting of hydrido, lower alkyl, halo, lower alkoxy, lower haloalkyl, and lower dialkylamino; or wherein $R^6$ and $R^7$ together form —OCH$_2$O—; wherein $R^{10}$, $R^{11}$, $R^{13}$ and $R^{14}$ are hydrido; and wherein $R^{12}$ is aminosulfonyl; or a pharmaceutically-acceptable salt thereof.

5. Compound of claim 4 wherein each of $R^1$ through $R^4$ is independently selected from the group consisting of hydrido, fluoror, chloro and bromo; or wherein $R^2$ and $R^3$ together form —OCH$_2$O—; wherein each of $R^5$ and $R^9$ is hydrido; wherein each of $R^6$ through $R^8$ is independently selected from the group consisting of hydrido, methyl, ethyl, fluoro, chloro, bromo, methoxy, ethoxy, propoxy, n-butoxy, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, N-ethyl-N-methylamino, N,N-dimethylamino, and N,N-diethylamino; or wherein $R^6$ and $R^7$ together form —OCH$_2$O—; wherein $R^{10}$, $R^{11}$, $R^{13}$ and $R^{14}$ are hydrido; and wherein $R^{12}$ is aminosulfonyl; or a pharmaceutically-acceptable salt thereof.

6. Compound of claim 5 selected from compounds, and their pharmaceutically acceptable salts, of the group consisting of 4-[2-(4-methylphenyl)phenyl]benzenesulfonamide;

4-[2-(3-fluoro-4-methylphenyl)phenyl]benzenesulfonamide;

4-[2-(3-chloro-4-methylphenyl)phenyl]benzenesulfonamide;

4-[2-(4-methoxyphenyl)phenyl]benzenesulfonamide;

4-[2-(3-fluoro-4-methoxyphenyl)phenyl]benzenesulfonamide;

4-[2-(3-chloro-4-methoxyphenyl)phenyl]benzenesulfonamide;

4-[2-(4-fluorophenyl)phenyl]benzenesulfonamide;

4-[2-(3,4-difluorophenyl)phenyl]benzenesulfonamide;

4-[2-(3-chloro-4-fluorophenyl)phenyl]benzenesulfonamide;

4-[2-(4-chlorophenyl)phenyl]benzenesulfonamide;

4-[2-(4-chloro-3-fluorophenyl)phenyl]benzenesulfonamide;

4-[2-(3,4-dichlorophenyl)phenyl]benzenesulfonamide;

4-[2-(4-trifluoromethylphenyl)phenyl]benzenesulfonamide;

4-[2-(3-fluoro-4-trifluoromethylphenyl)phenyl]benzenesulfonamide;

4-[2-(3-chloro-4-trifluoromethylphenyl)phenyl]benzenesulfonamide;

4-[2-[4-(N,N-dimethylamino)phenyl]phenyl]benzenesulfonamide;

4-[2-[3-fluoro-4-(N,N-dimethylamino)phenyl]phenyl]benzenesulfonamide;

4-[2-[3-chloro-4-(N,N-dimethylamino)phenyl]phenyl]benzenesulfonamide;

4-[6-(4-fluorophenyl)-1,3-benzodioxol-5-yl]benzenesulfonamide;

4-[6-(3,4-difluorophenyl)-1,3-benzodioxol-5-yl]benzenesulfonamide;

4-[6-(3-chloro-4-fluorophenyl)-1,3-benzodioxol-5-yl]benzenesulfonamide;

4-[6-[4-(N,N-dimethylamino)phenyl]-1,3-benzodioxol-5-yl]benzenesulfonamide;

4-[6-[4-(N,N-dimethylamino)-3-fluorophenyl]-1,3-benzodioxol-5-yl]benzenesulfonamide;

4-[6-[3-chloro-4-(N,N-dimethylamino)phenyl]-1,3-benzodioxol-5-yl]benzenesulfonamide;

4-[6-(3,5-difluoro-4-methylphenyl)-1,3-benzodioxol-5-yl]benzenesulfonamide;

4-[6-(3,5-dichloro-4-methylphenyl)-1,3-benzodioxol-5-yl]benzenesulfonamide;

4-[6-(3,5-difluoro-4-methoxyphenyl)-1,3-benzodioxol-5-yl]benzenesulfonamide;

4-[6(3,5-dichloro-4-methoxyphenyl)-1,3-benzodioxol-5-yl]benzenesulfonamide;

4-[4,5-difluoro-2-(4-methylphenyl)phenyl]
benzenesulfonamide;

4-[4,5-difluoro-2-(3-fluoro-4-methylphenyl)phenyl]
benzenesulfonamide;

4-[2-(3-chloro-4-methylphenyl)-4,5-difluorophenyl]
benzenesulfonamide;

4-[4,5-difluoro-2-(4-methoxyphenyl)phenyl]
benzenesulfonamide;

4-[4,5-difluoro-2-(3-fluoro-4-methoxyphenyl)phenyl]
benzenesulfonamide;

4-[2-(3-chloro-4-methoxyphenyl)-4,5-difluorophenyl]
benzenesulfonamide;

4-[4,5-difluoro-2-(4-fluorophenyl)phenyl]
benzenesulfonamide;

4-[4,5-difluoro-2-(3,4-difluorophenyl)phenyl]
benzenesulfonamide;

4-[2-(3-chloro-4-fluorophenyl)-4,5-difluorophenyl]
benzenesulfonamide;

4-[4,5-difluoro-2-(4-fluoro-3-methylphenyl)phenyl]
benzenesulfonamide;

4-[4,5-difluoro-2-(4-fluoro-3-methoxyphenyl)phenyl]
benzenesulfonamide;

4-[2-(4-chlorophenyl)-4,5-difluorophenyl]
benzenesulfonamide;

4-[2-(4-chloro-3-methylphenyl)-4,5-difluorophenyl]
benzenesulfonamide;

4-[2-(4-chloro-3-fluorophenyl)-4,5-difluorophenyl]
benzenesulfonamide;

4-[2-(3,4-dichlorophenyl)-4,5-difluorophenyl]
benzenesulfonamide;

4-[2-(4-chloro-3-methoxyphenyl)-4,5-difluorophenyl]
benzenesulfonamide;

4-[4,5-difluoro-2-[4-(N,N-dimethylamino)phenyl]
phenyl]benzenesulfonamide;

4-[4,5-difluoro-2-[4-(N,N-dimethylamino)-3-methylphenyl]phenyl]benzenesulfonamide;

4-[4,5-difluoro-2-[4-(N,N-dimethylamino)-3-fluorophenyl]phenyl]benzenesulfonamide;

4-[2-[3-chloro-4-N,N-dimethylamino)phenyl]-4,5-difluorophenyl]benzenesulfonamide;

4-[4,5-difluoro-2-[4-(N,N-dimethylamino)-3-methoxyphenyl]phenyl]benzenesulfonamide;

4-[4,5-difluoro-2-(3,4,5-trimethylphenyl)phenyl]
benzenesulfonamide;

4-[4,5-difluoro-2-(3,5-difluoro-4-methylphenyl)phenyl]
benzenesulfonamide;

4-[2-(3,5-dichloro-4-methylphenyl)-4,5-difluorophenyl]
benzenesulfonamide;

4-[4,5-difluoro-2-(3,5-dimethoxy-4-methylphenyl)
phenyl]benzenesulfonamide;

4-[4,5-difluoro-2-(3,5-dimethyl-4-methoxyphenyl)
phenyl]benzenesulfonamide;

4-[4,5-difluoro-2-(3,5-difluoro-4-methoxyphenyl)
phenyl]benzenesulfonamide;

4-[2-(3,5-dichloro-4-methoxyphenyl)-4,5-difluorophenyl]benzenesulfonamide;

4-[4,5-difluoro-2-(3,4,5-trimethoxyphenyl)phenyl]
benzenesulfonamide;

4-[4,5-difluoro-2-(3,5-dimethyl-4-fluorophenyl)phenyl]
benzenesulfonamide;

4-[4,5-difluoro-2-(3,4,5-trifluorophenyl)phenyl]
benzenesulfonamide;

4-[2-(3,5-dichloro-4-fluorophenyl)-4,5-difluorophenyl]
benzenesulfonamide;

4-[4,5-difluoro-2-(3,5-dimethoxy-4-fluorophenyl)
phenyl]benzenesulfonamide;

4-[2-(4-chloro-3,5-dimethylphenyl)-4,5-difluorophenyl]
benzenesulfonamide;

4-[2-(4-chloro-3,5-difluorophenyl)-4,5-difluorophenyl]
benzenesulfonamide;

4-[4,5-difluoro-2-(3,4,5-trichlorophenyl)phenyl]
benzenesulfonamide;

4-[2-(4-chloro-3,5-dimethoxyphenyl)-4,5-difluorophenyl]benzenesulfonamide;

4,5-difluoro-2-[3,5-dimethyl-4-(N,N-dimethylamino)
phenyl]phenyl]benzenesulfonamide;

4-[4,5-difluoro-2-[3,5-difluoro-4-(N,N-dimethylamino)
phenyl]phenyl]benzenesulfonamide;

4-[2-[3,5-dichloro-4-(N,N-dimethylamino)phenyl]-4,5-difluorophenyl]benzenesulfonamide;

4-[2,3,4,5-tetrafluoro-2-(4-methylphenyl)phenyl]
benzenesulfonamide;

4-[2,3,4,5-tetrafluoro-2-(3-fluoro-4-methylphenyl)
phenyl]benzenesulfonamide;

4-[2,3,4,5-tetrafluoro-2-(3-chloro-4-methylphenyl)
phenyl]benzenesulfonamide;

4-[2,3,4,5-tetrafluoro-2-(4-methoxyphenyl)phenyl]
benzenesulfonamide;

4-[2,3,4,5-tetrafluoro-2-(4-methoxy-3-methylphenyl)
phenyl]benzenesulfonamide;

4-[2,3,4,5-tetrafluoro-2-(3-fluoro-4-methoxyphenyl)
phenyl]benzenesulfonamide;

4-[2,3,4,5-tetrafluoro-2-(3-chloro-4-methoxyphenyl)
phenyl]benzenesulfonamide;

4-[2,3,4,5-tetrafluoro-2-(3,4-dimethoxyphenyl)phenyl]
benzenesulfonamide;

4-[2,3,4,5-tetrafluoro-2-(4-fluorophenyl)phenyl]
benzenesulfonamide;

4-[2,3,4,5-tetrafluoro-2-(4-fluoro-3-methylphenyl)
phenyl]benzenesulfonamide;

4-[2,3,4,5-tetrafluoro-2-(3,4-difluorophenyl)phenyl]
benzenesulfonamide;

4-[2,3,4,5-tetrafluoro-2-(3-chloro-4-fluorophenyl)
phenyl]benzenesulfonamide; and 4-[2,3,4,5-tetrafluoro-2-(4-fluoro-3-methoxyphenyl)
phenyl]benzenesulfonamide.

7. Compound of claim 5 selected from compounds, and their pharmaceutically acceptable salts, of the group consisting of 4-[2-(3-chloro-4-fluorophenyl)-4,5-difluorophenyl]
benzenesulfonamide;

4-[2-(4-fluorophenyl)phenyl]benzenesulfonamide;

4-[2-(4-chlorophenyl)phenyl]benzenesulfonamide;

4-[2-(3-fluoro-a-methoxyphenyl)phenyl]
benzenesulfonamide;

4-[2-(3-chloro-4-methoxyphenyl)phenyl]
benzenesulfonamide;

4-[2-(4-trifluoromethylphenyl)phenyl]
benzenesulfonamide;

4-[2-(3-chloro-4-fluorophenyl)phenyl]
benzenesulfonamide;

4-[4,5-difluoro-2-(4-fluorophenyl)phenyl]
benzenesulfonamide;

4-[2,3,4,5-tetrafluoro-2-(4-fluorophenyl)phenyl]
benzenesulfonamide;

4-[2-(3-chloro-4-methoxyphenyl)-4,5-difluorophenyl] benzenesulfonamide;

4-[4,5-difluoro-2-(3-fluoro-4-methoxyphenyl)phenyl] benzenesulfonamide;

4-[6(4-fluorophenyl)-1,3-benzodioxol-5-yl] benzenesulfonamide;

4-[4,5-difluoro-2-4-(methylphenyl)phenyl] benzenesulfonamide;

4-[2-(1,3-benzodioxol-5-yl)-4,5-difluorophenyl] benzenesulfonamide;

4-[2-(3-chloro-4-methylphenyl)-4,5-difluorophenyl] benzenesulfonamide; and

4-[2-[3-chloro-4-(N,N-dimethylamino)phenyl]-4,5-difluorophenyl]benzenesulfonamide.

8. Compound of claim 5 where the compound is 4-[4,5-difluoro-2-(3-chloro-4-fluorophenyl)phenyl] benzenesulfonamide, or a pharmaceutically-acceptable salt thereof.

9. Compound of claim 5 where the compound is 4-[2-(3-chloro-4-methoxyphenyl)phenyl]benzenesulfonamide, or a pharmaceutically-acceptable salt thereof.

10. Compound of claim 2 wherein each of $R^1$ and $R^4$ are hydrido; wherein each of $R^2$ and $R^3$ is independently selected from the group consisting of hydrido and halo; or wherein $R^2$ and $R^3$ together form —$OCH_2O$—; wherein each of $R^5$ and $R^9$ is hydrido; wherein each of $R^6$ through $R^8$ is independently selected from the group consisting of hydrido, lower alkyl, halo, and lower alkoxy; or wherein $R^6$ and $R^7$ together form —$OCH_2O$—; wherein $R^{10}$, $R^{11}$, $R^{13}$ and $R^{14}$ are hydrido; and wherein $R^{12}$ is methylsulfonyl; or a pharmaceutically-acceptable salt thereof.

11. Compound of claim 10 wherein each of $R^1$ and $R^4$ are hydrido; wherein each of $R^2$ and $R^3$ is independently selected from the group consisting of hydrido, fluoro, chloro and bromo; or wherein $R^2$ and $R^3$ together form —$OCH_2O$—; wherein each of $R^5$ and $R^9$ is hydrido; wherein each of $R^6$ through $R^8$ is independently selected from the group consisting of hydrido, methyl, ethyl, fluoro, chloro, bromo, methoxy, ethoxy, propoxy, and n-butoxy; or wherein $R^6$ and $R^7$ together form —$OCH_2O$—; wherein $R^{10}$, $R^{11}$, $R^{13}$ and $R^{14}$ are hydrido; and wherein $R^{12}$ is methylsulfonyl; or a pharmaceutically-acceptable salt thereof.

12. Compound of claim 11 selected from compounds, and their pharmaceutically acceptable salts, of the group consisting of 1-(4-fluorophenyl)-2-[4-(methylsulfonyl)phenyl] benzene;

1-(4-chlorophenyl)-2-[4-(methylsulfonyl)phenyl] benzene;

1-(3-chloro-4-methoxyphenyl)-2-[4-(methylsulfonyl) phenyl]benzene;

1-(3-fluoro-4-methoxyphenyl)-2-[4-(methylsulfonyl) phenyl]benzene;

1-(3-chloro-4-fluorophenyl)-2-[4-(methylsulfonyl) phenyl]benzene;

1-(4-fluorophenyl)-6-[4-(methylsulfonyl)phenyl]-1,3-benzodioxole;

1,2-difluoro-4-(4-fluorophenyl)-5-[4-(methylsulfonyl) phenyl]benzene;

1,2-difluoro-4-(4-methylphenyl)-5-[4-(methylsulfonyl) phenyl]benzene;

1-(3-chloro-4-methoxyphenyl)-4,5-difluoro-2-[4-(methylsulfonyl)phenyl]benzene;

1,2-difluoro-4-(3-fluoro-4-methoxyphenyl)-5-[4-(methylsulfonyl)phenyl]benzene;

1-(3-chloro-4-fluorophenyl)-4,5-difluoro-2-[4-(methylsulfonyl)phenyl]benzene;

1-(3,5-dichloro-4-methoxyphenyl)-4,5-difluoro-2-[4-(methylsulfonyl)phenyl]benzene;

1-(3,5-difluoro-4-methoxyphenyl)-4,5-difluoro-2-[4-(methylsulfonyl)phenyl]benzene;

5-[4,5-difluoro-2-[4-(methylsulfonyl)phenyl]phenyl]-1,3-benzodioxole;

1-(3-chloro-4-methylphenyl)-4,5-difluoro-2-[4-(methylsulfonyl)phenyl]benzene; and 2-chloro-4-[4,5-difluoro-2-[4-(methylsulfonyl)phenyl] phenyl]-N,N-dimethylbenzeneamine.

13. A compound of Formula II

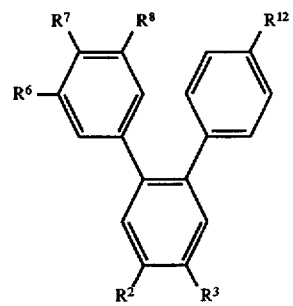

wherein each of $R^2$ and $R^3$ is independently selected from the group consisting of hydrido and halo; or wherein $R^2$ and $R^3$ together form —$OCH_2O$—; wherein each of $R^6$ through $R^8$ is independently selected from the group consisting of hydrido, lower alkyl, halo, lower alkoxy, lower haloalkyl, and lower dialkylamino; or wherein $R^6$ and $R^7$ together form —$OCH_2O$—; and wherein $R^{12}$ is selected from the group consisting of lower alkylsulfonyl and aminosulfonyl; or a pharmaceutically-acceptable salt thereof.

14. A compound of Formula III

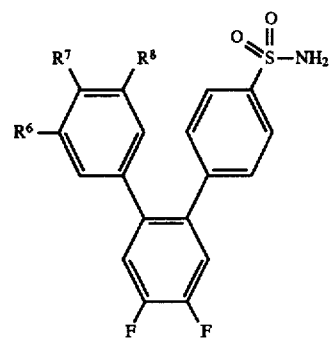

wherein each of $R^6$ through $R^8$ is independently selected from hydrido, halo, lower alkoxy, lower haloalkyl, amino, lower alkylamino, lower dialkylamino, and lower haloalkoxy; or wherein $R^6$ and $R^7$ together form —$OCH_2O$—; or a pharmaceutically-acceptable salt thereof.

15. A pharmaceutical composition comprising a therapeutically-effective amount of a compound and a pharmaceutically-acceptable carrier or diluent, said compound selected from a family of compounds of Formula I

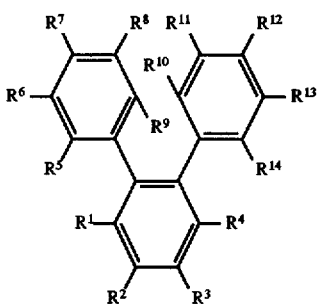

wherein each of $R^1$ through $R^4$ is independently selected from the group consisting of hydrido, halo, and alkoxy; wherein each of $R^5$ through $R^{14}$ is independently selected from the group consisting of hydrido, alkyl, halo, alkoxy, alkylthio, cyano, haloalkyl, amino, alkylamino, dialkylamino, haloalkoxy, hydroxyalkyl, alkoxyalkyl, hydroxyl, mercapto, aminosulfonyl and alkylsulfonyl; provided $R^{12}$ is selected from the group consisting of methylsulfonyl or aminosulfonyl; or a pharmaceutically-acceptable salt thereof.

16. The composition of claim 15 wherein each of $R^1$ through $R^4$ is independently selected from the group consisting of hydrido and halo; or wherein $R^2$ and $R^3$ together form —$OCH_2O$—; and wherein each of $R^5$ through $R^{14}$ is independently selected from the group consisting of hydrido, lower alkyl, halo, lower alkoxy, lower alkylthio, cyano, lower haloalkyl, amino, lower alkylamino, lower dialkylamino, lower haloalkoxy, lower hydroxyalkyl, lower alkoxyalkyl, hydroxyl, mercapto, aminosulfonyl and lower alkylsulfonyl; or wherein $R^6$ and $R^7$ together form —$OCH_2O$—; provided $R^{12}$ is selected from the group consisting of methylsulfonyl or aminosulfonyl; or a pharmaceutically-acceptable salt thereof.

17. The composition of claim 16 wherein each of $R^1$ through R4 is independently selected from the group consisting of hydrido and halo; or wherein $R^2$ and $R^3$ together form —$OCH_2O$—; wherein each of $R^5$ through $R^8$ is independently selected from the group, consisting of hydrido, lower alkyl, halo, lower alkoxy, lower haloalkyl, and lower dialkylamino; or wherein $R^6$ and $R^7$ together form —$OCH_2O$—; wherein $R^{10}$, $R^{11}$, $R^{13}$ and $R^{14}$ are hydrido; and wherein $R^{12}$ is selected from the group consisting of aminosulfonyl and lower alkylsulfonyl; or a pharmaceutically-acceptable salt thereof.

18. The composition of claim 17 wherein each of $R^1$ through $R^4$ is independently selected from hydrido and halo; or wherein $R^2$ and $R^3$ together form —$OCH_2O$—; wherein each of $R^5$ and $R^9$ is hydrido; wherein each of $R^6$ through $R^8$ is independently selected from hydrido, lower alkyl, halo, lower alkoxy, lower haloalkyl, and lower dialkylamino; or wherein $R^6$ and $R^7$ together form —$OCH_2O$—; wherein $R^{10}$, $R^{11}$, $R^{13}$ and $R^{14}$ are hydrido; and wherein $R^{12}$ is aminosulfonyl; or a pharmaceutically-acceptable salt thereof.

19. The composition of claim 18 wherein each of $R^1$ through $R^4$ is independently selected from hydrido, fluoro, chloro and bromo; or wherein $R^2$ and $R^3$ together form —$OCH_2O$—; wherein each of $R^5$ and $R^9$ is hydrido; wherein each of $R^6$ through $R^8$ is independently selected from hydrido, methyl, ethyl, fluoro, chloro, bromo, methoxy, ethoxy, propoxy, n-butoxy, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, N-ethyl-N-methylamino, N,N-dimethylamino, and N,N-diethylamino; or wherein $R^6$ and $R^7$ together form —$OCH_2O$—; wherein $R^{10}$, $R^{11}$, $R^{13}$ and $R^{14}$ are hydrido; and wherein $R^{12}$ is aminosulfonyl; or a pharmaceutically-acceptable salt thereof.

20. The composition of claim 19 wherein said compound is selected from compounds, and their pharmaceutically acceptable salts, of the group consisting of 4-[2-(4-methylphenyl)phenyl]benzenesulfonamide;

4-[2-(3-fluoro-4-methylphenyl)phenyl]benzenesulfonamide;

4-[2-(3-chloro-4-methylphenyl)phenyl]benzenesulfonamide;

4-[2-(4-methoxyphenyl)phenyl]benzenesulfonamide;

4-[2-(3-fluoro-4-methoxyphenyl)phenyl]benzenesulfonamide;

4-[2-(3-chloro-4-methoxyphenyl)phenyl]benzenesulfonamide;

4-[2-(4-fluorophenyl)phenyl]benzenesulfonamide;

4-[2-(3,4-difluorophenyl)phenyl]benzenesulfonamide;

4-[2-(3-chloro-4-fluorophenyl)phenyl]benzenesulfonamide;

4-[2-(4-chlorophenyl)phenyl]benzenesulfonamide;

4-[2-(4-chloro-3-fluorophenyl)phenyl]benzenesulfonamide;

4-[2-(3,4-dichlorophenyl)phenyl]benzenesulfonamide;

4-[2-(4-trifluoromethylphenyl)phenyl]benzenesulfonamide;

4-[2-(3-fluoro-4-atrifluoromethylphenyl)phenyl]benzenesulfonamide;

4-[2-(3-chloro-4-trifluoromethylphenyl)phenyl]benzenesulfonamide;

4-[2-[4-(N,N-dimethylamino)phenyl]phenyl]benzenesulfonamide;

4-[2-[3-fluoro-4-(N,N-dimethylamino)phenyl]phenyl]benzenesulfonamide;

4-[2-[3-chloro-4-(N,N-dimethylamino)phenyl]phenyl]benzenesulfonamide;

4-[6-(4-fluorophenyl)-1,3-benzodioxol-5-yl]benzenesulfonamide;

4-[6-(3,4-difluorophenyl)-1,3-benzodioxol-5-yl]benzenesulfonamide;

4-[6-(3-chloro-4-fluorophenyl)-1,3-benzodioxol-5-yl]benzenesulfonamide;

4-[6-[4-(N,N-dimethylamino)phenyl]-1,3-benzodioxol-5-yl]benzenesulfonamide;

4-[6-[4-(N,N-dimethylamino)-3-fluorophenyl]-1,3-benzodioxol-5-yl]benzenesulfonamide;

4-[6-[3-chloro-4-(N,N-dimethylamino)phenyl]-1,3-benzodioxol-5-yl]benzenesulfonamide;

4-[6-(3,5-difluoro-4-methylphenyl)-1,3-benzodioxol-5-yl]benzenesulfonamide;

4-[6-(3,5-dichloro-4-methylphenyl)-1,3-benzodioxol-5-yl]benzenesulfonamide;

4-[6-(3,5-difluoro-4-methoxyphenyl)-1,3-benzodioxol-5-yl]benzenesulfonamide);

4-[6-(3,5-dichloro-4-methoxyphenyl)-1,3-benzodioxol-5-yl]benzenesulfonamide;

4-[4,5-difluoro-2-(4-methylphenyl)phenyl]benzenesulfonamide;

4-[4,5-difluoro-2-(3-fluoro-4-methylphenyl)phenyl]benzenesulfonamide;

4-[2-(3-chloro-4-methylphenyl)-4,5-difluorophenyl]benzenesulfonamide;

4-[4,5-difluoro-2-(4-methoxyphenyl)phenyl]benzenesulfonamide;

4-[4,5-difluoro-2-(3-fluoro-4-methoxyphenyl)phenyl]benzenesulfonamide;

4-[2-(3-chloro-4-methoxyphenyl)-4,5-difluorophenyl]benzenesulfonamide;

4-[4,5-difluoro-2-(4-fluorophenyl)phenyl]benzenesulfonamide;

4-[4,5-difluoro-2-(3,4-difluorophenyl)phenyl]benzenesulfonamide;

4-[2-(3-chloro-4-fluorophenyl)-4,5-difluorophenyl]benzenesulfonamide;

4-[4,5-difluoro-2-(4-fluoro-3-methylphenyl)phenyl]benzenesulfonamide;

4-[4,5-difluoro-2-(4-fluoro-3-methoxyphenyl)phenyl]benzenesulfonamide;

4-[2-(4-chlorophenyl)-4,5-difluorophenyl]benzenesulfonamide;

4-[2-(4-chloro-3-methylphenyl)-4,5-difluorophenyl]benzenesulfonamide;

4-[2-(4-chloro-3-fluorophenyl)-4,5-difluorophenyl]benzenesulfonamide;

4-[2-(3,4-dichlorophenyl)-4,5-difluorophenyl]benzenesulfonamide;

4-[2-(4-chloro-3-methoxyphenyl)-4,5-difluorophenyl]benzenesulfonamide;

4-[4,5-difluoro-2-[4-(N,N-dimethylamino)phenyl]phenyl]benzenesulfonamide;

4-[4,5-difluoro-2-[4-(N,N-dimethylamino)-3-methylphenyl]phenyl]benzenesulfonamide;

4-[4,5-difluoro-2-[4-(N,N-dimethylamino)-3-fluorophenyl]phenyl]benzenesulfonamide;

4-[2-[3-chloro-4-N,N-dimethylamino)phenyl]-4,5-difluorophenyl]benzenesulfonamide;

4-[4,5-difluoro-2-[4-(N,N-dimethylamino)-3-methoxyphenyl]phenyl]benzenesulfonamide;

4-[4,5-difluoro-2-(3,4,5-trimethylphenyl)phenyl]benzenesulfonamide;

4-[4,5-difluoro-2-(3,5-difluoro-4-methylphenyl)phenyl]benzenesulfonamide;

4-[2-(3,5-dichloro-4-methylphenyl)-4,5-difluorophenyl]benzenesulfonamide;

4-[4,5-difluoro-2-(3,5-dimethoxy-4-methylphenyl)phenyl]benzenesulfonamide;

4-[4,5-difluoro-2-(3,5-dimethyl-4-methoxyphenyl)phenyl]benzenesulfonamide;

4-[4,5-difluoro-2-(3,5-difluoro-4-methoxyphenyl)phenyl]benzenesulfonamide;

4-[2-(3,5-dichloro-4-methoxyphenyl)-4,5-difluorophenyl]benzenesulfonamide;

4-[4,5-difluoro-2-(3,4,5-trimethoxyphenyl)phenyl]benzenesulfonamide;

4-[4,5-difluoro-2-(3,5-dimethyl-4-fluorophenyl)phenyl]benzenesulfonamide;

4-[4,5-difluoro-2-(3,4,5-trifluorophenyl)phenyl]benzenesulfonamide;

4-[2-(3,5-dichloro-4-fluorophenyl)-4,5-difluorophenyl]benzenesulfonamide;

4-[4,5-difluoro-2-(3,5-dimethoxy-4-fluorophenyl)phenyl]benzenesulfonamide;

4-[2-(4-chloro-3,5-dimethylphenyl)-4,5-difluorophenyl]benzenesulfonamide;

4-[2-(4-chloro-3,5-difluorophenyl)-4,5-difluorophenyl]benzenesulfonamide;

4-[4,5-difluoro-2-(3,4,5-trichlorophenyl)phenyl]benzenesulfonamide;

4-[2-(4-chloro-3,5-dimethoxyphenyl)-4,5-difluorophenyl]benzenesulfonamide;

4-[4,5-difluoro-2-[3,5-dimethyl-4-(N,N-dimethylamino)phenyl]phenyl]benzenesulfonamide;

4-[4,5-difluoro-2-[3,5-difluoro-4-(N,N-dimethylamino)phenyl]phenyl]benzenesulfonamide;

4-[2-[3,5-dichloro-4-(N,N-dimethylamino)phenyl]-4,5-difluorophenyl]benzenesulfonamide;

4-[2,3,4,5-tetrafluoro-2-(4-methylphenyl)phenyl]benzenesulfonamide;

4-[2,3,4,5-tetrafluoro-2-(3-fluoro-4-methylphenyl)phenyl]benzenesulfonamide;

4-[2,3,4,5-tetrafluoro-2-(3-chloro-4-methylphenyl)phenyl]benzenesulfonamide;

4-[2,3,4,5-tetrafluoro-2-(4-methoxyphenyl)phenyl]benzenesulfonamide;

4-[2,3,4,5-tetrafluoro-2-(4-methoxy-3-methylphenyl)phenyl]benzenesulfonamide;

4-[2,3,4,5-tetrafluoro-2-(3-fluoro-4-methoxyphenyl)phenyl]benzenesulfonamide;

4-[2,3,4,5-tetrafluoro-2-(3-chloro-4-methoxyphenyl)phenyl]benzenesulfonamide;

4-[2,3,4,5-tetrafluoro-2-(3,4-dimethoxyphenyl)phenyl]benzenesulfonamide;

4-[2,3,4,5-tetrafluoro-2-(4-fluorophenyl)phenyl]benzenesulfonamide;

4-[2,3,4,5-tetrafluoro-2-(4-fluoro-3-methylphenyl)phenyl]benzenesulfonamide;

4-[2,3,4,5-tetrafluoro-2-(3,4-difluorophenyl)phenyl]benzenesulfonamide;

4-[2,3,4,5-tetrafluoro-2-(3-chloro-4-fluorophenyl)phenyl]benzenesulfonamide; and 4-[2,3,4,5-tetrafluoro-2-(4-fluoro-3-methoxyphenyl)phenyl]benzenesulfonamide.

21. The composition of claim 19 wherein said compound is selected from compounds, and their pharmaceutically acceptable salts, of the group consisting of 4-[2-(3-chloro-4-fluorophenyl)-4,5-difluorophenyl]benzenesulfonamide;

4-[2-(4-fluorophenyl)phenyl]benzenesulfonamide;

4-[2-(4-chlorophenyl)phenyl]benzenesulfonamide;

4-[2-(3-fluoro-4-methoxyphenyl)phenyl]benzenesulfonamide;

4-[2-(3-chloro-4-methoxyphenyl)phenyl]benzenesulfonamide;

4-[2-(4-trifluoromethylphenyl)phenyl]benzenesulfonamide;

4-[2-(3-chloro-4-fluorophenyl)phenyl]benzenesulfonamide;

4-[4,5-difluoro-2-(4-fluorophenyl)phenyl]benzenesulfonamide;

4-[2,3,4,5-tetrafluoro-2-(4-fluorophenyl)phenyl]benzenesulfonamide;

4-[2-(3-chloro-4-methoxyphenyl)-4,5-difluorophenyl]benzenesulfonamide;

4-[4,5-difluoro-2-(3-fluoro-4-methoxyphenyl)phenyl]benzenesulfonamide;

4-[6 (4-fluorophenyl)-1,3-benzodioxol-5-yl] benzenesulfonamide;

4-[4,5-difluoro-2-(4-methylphenyl)phenyl] benzenesulfonamide;

4-[2-(1,3-benzodioxol-5-yl)-4,5-difluorophenyl] benzenesulfonamide;

4-[2-(3-chloro-4-methylphenyl)-4,5-difluorophenyl] benzenesulfonamide; and

4-[2-[3-chloro-4-(N,N-dimethylamino)phenyl]-4,5-difluorophenyl]benzenesulfonamide.

22. The composition of claim 19 where the compound is 4-[4,5-difluoro-2-(3-chloro-4-fluorophenyl)phenyl] benzenesulfonamide, or a pharmaceutically-acceptable salt thereof.

23. The composition of claim 19 where the compound is 4-[2-(3-chloro-4-methoxyphenyl)phenyl] benzenesulfonamide, or a pharmaceutically-acceptable salt thereof.

24. The composition of claim 17 wherein each of $R^1$ and $R^4$ are hydrido; wherein each of $R^2$ and $R^3$ is independently selected from the group consisting of hydrido and halo; or wherein $R^2$ and $R^3$ together form —OCH$_2$O—; wherein each of $R^5$ and $R^9$ is hydrido; wherein each of $R^6$ through $R^8$ is independently selected from the group consisting of hydrido, lower alkyl, halo, and lower alkoxy; or wherein $R^6$ and $R^7$ together form —OCH$_2$O—; wherein $R^{10}$, $R^{11}$, $R^{13}$ and $R^{14}$ are hydrido; and wherein $R^{12}$ is lower alkylsulfonyl; or a pharmaceutically-acceptable salt thereof.

25. The composition of claim 24 wherein each of $R^1$ and $R^4$ are hydrido; wherein each of $R^2$ and $R^3$ is independently selected from the group consisting of hydrido, fluoro, chloro and bromo; or wherein $R^2$ and $R^3$ together form —OCH$_2$O—; wherein each of $R^5$ and $R^9$ is hydrido; wherein each of $R^6$ through $R^8$ is independently selected from the group consisting of hydrido, methyl, ethyl, fluoro, chloro, bromo, methoxy, ethoxy, propoxy, and n-butoxy; or wherein $R^6$ and $R^7$ together form —OCH$_2$O—; wherein $R^{10}$, $R^{11}$, $R^{13}$ and $R^{14}$ are hydrido; and wherein $R^{12}$ is methylsulfonyl; or a pharmaceutically-acceptable salt thereof.

26. The composition of claim 25 wherein said compound is selected from compounds, and their pharmaceutically acceptable salts of the group consisting of 1-(4-fluorophenyl)-2-[4-(methylsulfonyl)phenyl] benzene;

1-(4-chlorophenyl)-2-[4-(methylsulfonyl)phenyl] benzene;

1-(3-chloro-4-methoxyphenyl)-2-[4-(methylsulfonyl) phenyl]benzene;

1-(3-fluoro-4-methoxyphenyl)-2-[4-(methylsulfonyl) phenyl]benzene;

1-(3-chloro-4-fluorophenyl)-2-[4-(methylsulfonyl) phenyl]benzene;

1-4-fluorophenyl)-6-[4-(methylsulfonyl)phenyl]-1,3-benzodioxole;

1,2-difluoro-4-(4-fluorophenyl)-5-[4-(methylsulfonyl) phenyl]benzene;

1,2-difluoro-4-(4-methylphenyl)-5-[4-(methylsulfonyl) phenyl]benzene;

1-3-chloro-4-methoxyphenyl)-4,5-difluoro-2-[4-(methylsulfonyl)phenyl]benzene;

1,2-difluoro-4-(3-fluoro-4-methoxyphenyl)-5-[4-(methylsulfonyl)phenyl]benzene;

1-(3-chloro-4-fluorophenyl)-4,5-difluoro-2-[4-(methylsulfonyl)phenyl]benzene;

1-(3,5-dichloro-4-methoxyphenyl)-4,5-difluoro-2-[4-(methylsulfonyl)phenyl]benzene;

1-(3,5-difluoro-4-methoxyphenyl)-4,5-difluoro-2-[4-(methylsulfonyl)phenyl]benzene;

5-[4,5-difluoro-2-[4-(methylsulfonyl)phenyl]phenyl]-1,3-benzodioxole;

1-(3-chloro-4-methylphenyl)-4,5-difluoro-2-[4-(methylsulfonyl)phenyl]benzene; and 2-chloro-4-[4,5-difluoro-2-[4-(methylsulfonyl)phenyl] phenyl]-N,N-dimethylbenzeneamine.

27. A pharmaceutical composition comprising a therapeutically-effective amount of a compound and a pharmaceutically-acceptable carrier or diluent, said compound selected from a family of compounds of Formula II

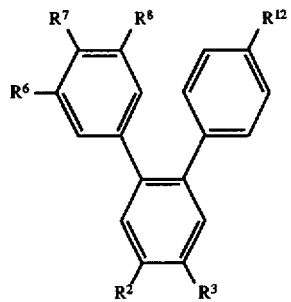

wherein each of $R^2$ and $R^3$ is independently selected from the group consisting of hydrido and halo; or wherein $R^2$ and $R^3$ together form —OCH$_2$O—; wherein each of $R^6$ through $R^8$ is independently selected from the, group consisting of hydrido, lower alkyl, halo, lower alkoxy, lower haloalkyl, and lower dialkylamino; or wherein $R^6$ and $R^7$ together form —OCH$_2$O—; and wherein $R^{12}$ is selected from the group consisting of lower alkylsulfonyl and aminosulfonyl; or a pharmaceutically-acceptable salt thereof.

28. A pharmaceutical composition comprising a therapeutically-effective amount of a compound and a pharmaceutically-acceptable carrier or diluent, said compound selected from a family of compounds of Formula III

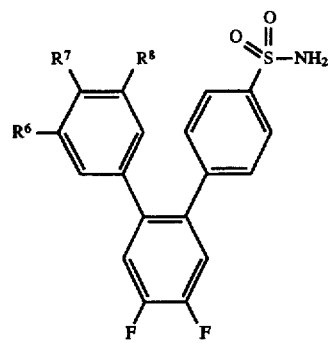

wherein each of $R^6$ through $R^8$ is independently selected from hydrido, halo, lower alkoxy, lower haloalkyl, amino, lower alkylamino, lower dialkylamino, and lower haloalkoxy; or wherein $R^6$ and $R^7$ together form —OCH$_2$O—; or a pharmaceutically-acceptable salt thereof.

29. A method of treating inflammation or an inflammation-associated disorder in a subject, said method comprising administering to the subject having or susceptible to such inflammation or inflammation-associated disorder, a therapeutically-effective amount of a compound of Formula I

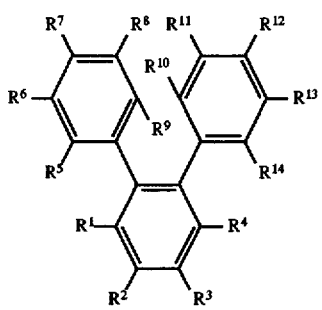

wherein each of $R^1$ through $R^4$ is independently selected from the group consisting of hydrido, halo, and alkoxy; wherein each of $R^5$ through $R^{14}$ is independently selected from the group consisting of hydrido, alkyl, halo, alkoxy, alkylthio, cyano, haloalkyl, amino, alkylamino, dialkylamino, haloalkoxy, hydroxyalkyl, alkoxyalkyl, hydroxyl, mercapto, aminosulfonyl and alkylsulfonyl; or a pharmaceutically-acceptable salt thereof.

30. The method of claim 29 wherein each of $R^1$ through $R^4$ is independently selected from the group consisting of hydrido and halo; or wherein $R^2$ and $R^3$ together form —OCH$_2$O—; and wherein each of $R^5$ through $R^{14}$ is independently selected from the group consisting of hydrido, lower alkyl, halo, lower alkoxy, lower alkylthio, cyano, lower haloalkyl, amino, lower alkylamino, lower dialkylamino, lower haloalkoxy, lower hydroxyalkyl, lower alkoxyalkyl, hydroxyl, mercapto, aminosulfonyl and lower alkylsulfonyl; or wherein $R^6$ and $R^7$ together form —OCH$_2$O—; or a pharmaceutically-acceptable salt thereof.

31. The method of claim 30 wherein each of $R^1$ through $R^4$ is independently selected from hydrido and halo; or wherein $R^2$ and $R^3$ together form —OCH$_2$O—; wherein each of $R^5$ through $R^8$ is independently selected from the group consisting of hydrido, lower alkyl, halo, lower alkoxy, lower haloalkyl, and lower dialkylamino; or wherein $R^6$ and $R^7$ together form —OCH$_2$O—; wherein $R^{10}$, $R^{11}$, $R^{13}$ and $R^{14}$ are hydrido; and wherein $R^{12}$ is selected from the group consisting of aminosulfonyl and lower alkylsulfonyl; or a pharmaceutically-acceptable salt thereof.

32. The method of claim 31 wherein each of $R^1$ through $R^4$ is independently selected from the group consisting of hydrido and halo; or wherein $R^2$ and $R^3$ together form —OCH$_2$O—; wherein each of $R^5$ and $R^9$ is hydrido; wherein each of $R^6$ through $R^8$ is independently selected from the group consisting of hydrido, lower alkyl, halo, lower alkoxy, lower haloalkyl, and lower dialkylamino; or wherein $R^6$ and $R^7$ together form —OCH$_2$O—; wherein $R^{10}$, $R^{11}$, $R^{13}$ and $R^{14}$ are hydrido; and wherein $R^{12}$ is aminosulfonyl; or a pharmaceutically-acceptable salt thereof.

33. The method of claim 32 wherein each of $R^1$ through $R^4$ is independently selected from the group consisting of hydrido, fluoro, chloro and bromo; or wherein $R^2$ and $R^3$ together form —OCH$_2$O—; wherein each of $R^5$ and $R^9$ is hydrido; wherein each of $R^6$ through $R^8$ is independently selected from the group consisting of hydrido, methyl, ethyl, fluoro, chloro, bromo, methoxy, ethoxy, propoxy, n-butoxy, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, N-ethyl-N-methylamino, N,N-dimethylamino, and N,N-diethyiamino; or wherein $R^6$ and $R^7$ together form —OCH$_2$O—; wherein $R^{10}$, $R^{11}$, $R^{13}$ and $R^{14}$ are hydrido; and wherein $R^{12}$ is aminosulfonyl; or a pharmaceutically-acceptable salt thereof.

34. The method of claim 33 wherein said compound is selected from compounds, and their pharmaceutically acceptable salts, of the group consisting of 4-[2-(4-methylphenyl)phenyl]benzenesulfonamide;

4-[2-(3-fluoro-4-methylphenyl)phenyl] benzenesulfonamide;

4-[2-(3-chloro-4-methylphenyl)phenyl] benzenesulfonamide;

4-[2-(4-methoxyphenyl)phenyl]benzenesulfonamide;

4-[2-(3-fluoro-4-methoxyphenyl)phenyl] benzenesulfonamide;

4-[2-(3-chloro-4-methoxyphenyl)phenyl] benzenesulfonamide;

4-[2-(4-fluorophenyl)phenyl]benzenesulfonamide;

4-[2-(3,4-difluorophenyl)phenyl]benzenesulfonamide;

4-[2-(3-chloro-4-fluorophenyl)phenyl] benzenesulfonamide;

4-[2-(4-chlorophenyl)phenyl]benzenesulfonamide;

4-[2-(4-chloro-3-fluorophenyl)phenyl] benzenesulfonamide;

4-[2-(3,4-dichlorophenyl)phenyl]benzenesulfonamide;

4-[2-(4-trifluoromethylphenyl)phenyl] benzenesulfonamide;

4-[2-(3-fluoro-4-trifluoromethylphenyl)phenyl] benzenesulfonamide;

4-[2-(3-chloro-4-trifluoromethylphenyl)phenyl] benzenesulfonamide;

4-[2-[4-(N,N-dimethylamino)phenyl]phenyl] benzenesulfonamide;

4-[2-[3-fluoro-4-(N,N-dimethylamino)phenyl]phenyl] benzenesulfonamide;

4-[2-[3-chloro-4-(N,N-dimethylamino)phenyl]phenyl] benzenesulfonamide;

4-[6-(4-fluorophenyl)-1,3-benzodioxol-5-yl] benzenesulfonamide;

4-[6-(3,4-difluorophenyl)-1,3-benzodioxol-5-yl] benzenesulfonamide;

4-[6-(3-chloro-4-fluorophenyl)-1,3-benzodioxol-5-yl] benzenesulfonamide;

4-[6-[4-(N,N-dimethylamino)phenyl]-1,3-benzodioxol-5-yl]benzenesulfonamide;

4-[6-[4-(N,N-dimethylamino)-3-fluorophenyl]-1,3-benzodioxol-5-yl]benzenesulfonamide;

4-[6-[3-chloro-4-[(N,N-dimethylamino)phenyl]-1,3-benzodioxol-5-yl]benzenesulfonamide;

4-[6-(3,5-difluoro-4-methylphenyl)-1,3-benzodioxol-5-yl]benzenesulfonamide;

4-[6-(3,5-dichloro-4-methylphenyl)-1,3-benzodioxol-5-yl]benzenesulfonamide;

4-[6-(3,5-difluoro-4-methoxyphenyl)-1,3-benzodioxol-5-yl]benzenesulfonamide;

4-[6-(3,5-dichloro-4-methoxyphenyl)-1,3-benzodioxol-5-yl]benzenesulfonamide;

4-[4,5-difluoro-2-(4-methylphenyl)phenyl] benzenesulfonamide;

4-[4,5-difluoro-2-(3-fluoro-4-methylphenyl)phenyl] benzenesulfonamide;

4-[2-(3-chloro-4-methylphenyl)-4,5-difluorophenyl] benzenesulfonamide;

4-[4,5-difluoro-2-(4-methoxyphenyl)phenyl] benzenesulfonamide;

4-[4,5-difluoro-2-(3-fluoro-4-methoxyphenyl)phenyl]
benzenesulfonamide;

4-[2-(3-chloro-4-methoxyphenyl)-4,5-difluorophenyl]
benzenesulfonamide;

4-[4,5-difluoro-2-(4-fluorophenyl)phenyl]
benzenesulfonamide;

4-[4,5-difluoro-2-(3,4-difluorophenyl)phenyl]
benzenesulfonamide;

4-[2-(3-chloro-4-fluorophenyl)-4,5-difluorophenyl]
benzenesulfonamide;

4-[4,5-difluoro-2-(4-fluoro-3-methylphenyl)phenyl]
benzenesulfonamide;

4-[4,5-difluoro-2-(4-fluoro-3-methoxyphenyl)phenyl]
benzenesulfonamide;

4-[2-(4-chlorophenyl)-4,5-difluorophenyl]
benzenesulfonamide;

4-[2-(4-chloro-3-methylphenyl)-4,5-difluorophenyl]
benzenesulfonamide;

4-[2-(4-chloro-3-fluorophenyl)-4,5-difluorophenyl]
benzenesulfonamide;

4-[2-(3,4-dichlorophenyl)-4,5-difluorophenyl]
benzenesulfonamide;

4-[2-(4-chloro-3-methoxyphenyl)-4,5-difluorophenyl]
benzenesulfonamide;

4-[4,5-difluoro-2-[4-(N,N-dimethylamino)phenyl]
phenyl]benzenesulfonamide;

4-[4,5-difluoro-2-[4-(N,N-dimethylamino)-3-methylphenyl]phenyl]benzenesulfonamide;

4-[4,5-difluoro-2-[4-(N,N-dimethylamino)-3-fluorophenyl]phenyl]benzenesulfonamide;

4-[2-[3-chloro-4-N,N-dimethylamino)phenyl]-4,5-difluorophenyl]benzenesulfonamide;

4-[4,5-difluoro-2-[4-(N,N-dimethylamino)-3-methoxyphenyl]phenyl]benzenesulfonamide;

4-[4,5-difluoro-2-(3,4,5-trimethylphenyl)phenyl]
benzenesulfonamide;

4-[4,5-difluoro-2-(3,5-difluoro-4-methylphenyl)phenyl]
benzenesulfonamide;

4-[2-(3,5-dichloro-4-methylphenyl)-4,5-difluorophenyl]
benzenesulfonamide;

4-[4,5-difluoro-2-(3,5-dimethoxy-4-methylphenyl)
phenyl]benzenesulfonamide;

4-[4,5-difluoro-2-(3,5-dimethyl-4-methoxyphenyl)
phenyl]benzenesulfonamide;

4-[4,5-difluoro-2-(3,5-difluoro-4-methoxyphenyl)
phenyl]benzenesulfonamide;

4-[2-(3,5-dichloro-4-methoxyphenyl)-4,5-difluorophenyl]benzenesulfonamide;

4-[4,5-difluoro-2-(3,4,5-trimethoxyphenyl)phenyl]
benzenesulfonamide;

4-[4,5-difluoro-2-(3,5-dimethyl-4-fluorophenyl)phenyl]
benzenesulfonamide;

4-[4,5-difluoro-2-(3,4,5-trifluorophenyl)phenyl]
benzenesulfonamide;

4-[2-(3,5-dichloro-4-fluorophenyl)-4,5-difluorophenyl]
benzenesulfonamide;

4-[4,5-difluoro-2-(3,5-dimethoxy-4-fluorophenyl)
phenyl]benzenesulfonamide;

4-[2-(4-chloro-3,5-dimethylphenyl)-4,5-difluorophenyl]
benzenesulfonamide;

4-[2-(4-chloro-3,5-di fluorophenyl)-4,5-difluorophenyl]
benzenesulfonamide;

4-[4,5-difluoro-2-(3,4,5-trichlorophenyl)phenyl]
benzenesulfonamide;

4-[2-(4-chloro-3,5-dimethoxyphenyl)-4,5-difluorophenyl]benzenesulfonamide;

4-[4,5-difluoro-2-[3,5-dimethyl-4-(N,N-dimethylamino)phenyl]phenyl]benzenesulfonamide;

4-[4,5-difluoro-2-[3,5-difluoro-4-(N,N-dimethylamino)phenyl]phenyl]benzenesulfonamide;

4-[2-[3,5-dichloro-4-(N,N-dimethylamino)phenyl]-4,5-difluorophenyl]benzenesulfonamide;

4-[2,3,4,5-tetrafluoro-2-(4-methylphenyl)phenyl]
benzenesulfonamide;

4-[2,3,4,5-tetrafluoro-2-(3-fluoro-4-methylphenyl)
phenyl]benzenesulfonamide;

4-[2,3,4,5-tetrafluoro-2-(3-chloro-4-methylphenyl)
phenyl]benzenesulfonamide;

4-[2,3,4,5-tetrafluoro-2-(4-methoxyphenyl)phenyl]
benzenesulfonamide;

4-[2,3,4,5-tetrafluoro-2-(4-methoxy-3-methylphenyl)
phenyl]benzenesulfonamide;

4-[2,3,4,5-tetrafluoro-2-(3-fluoro-4-methoxyphenyl)
phenyl]benzenesulfonamide;

4-[2,3,4,5-tetrafluoro-2-(3-chloro-4-methoxyphenyl)
phenyl]benzenesulfonamide;

4-[2,3,4,5-tetrafluoro-2-(3,4-dimethoxyphenyl)phenyl]
benzenesulfonamide;

4-[2,3,4,5-tetrafluoro-2-(4-fluorophenyl)phenyl]
benzenesulfonamide;

4-[2,3,4,5-tetrafluoro-2-(4-fluoro-3-methylphenyl)
phenyl]benzenesulfonamide;

4-[2,3,4,5-tetrafluoro-2-(3,4-difluorophenyl)phenyl]
benzenesulfonamide;

4-[2,3,4,5-tetrafluoro-2-(3-chloro-4-fluorophenyl)
phenyl]benzenesulfonamide; and 4-[2,3,4,5-tetrafluoro-2-(4-fluoro-3-methoxyphenyl)
phenyl]benzenesulfonamide.

35. The method of claim 33 wherein said compound is selected from compounds, and their pharmaceutically acceptable salts, of the group consisting of 4-[2-(3-chloro-4-fluorophenyl)-4,5-dif luorophenyl]
benzenesulfonamide;

4-[2-(4-fluorophenyl)phenyl]benzenesulfonamide;

4-[2-(4-chlorophenyl)phenyl]benzenesulfonamide;

4-[2-(3-fluoro-4-methoxyphenyl)phenyl]
benzenesulfonamide;

4-[2-(3-chloro-4-methoxyphenyl)phenyl]
benzenesulfonamide;

4-[2-(4-trifluoromethylphenyl)phenyl]
benzenesulfonamide;

4-[2-(3-chloro-4-fluorophenyl)phenyl]
benzenesulfonamide;

4-[4,5-difluoro-2-(4-fluorophenyl)phenyl]
benzenesulfonamide;

4-[2,3,4,5-tetrafluoro-2-(4-fluorophenyl)phenyl]
benzenesulfonamide;

4-[2-(3-chloro-4-methoxyphenyl)-4,5-difluorophenyl]
benzenesulfonamide;

4-[4,5-difluoro-2-(3-fluoro-4-methoxyphenyl)phenyl]
benzenesulfonamide;

4-[6-(4-fluorophenyl)-1,3-benzodioxol-5-yl]
benzenesulfonamide;

4-[4,5-difluoro-2-(4-methylphenyl)phenyl]
benzenesulfonamide;

4-[2-(1,3-benzodioxol-5-yl)-4,5-difluorophenyl] benzenesulfonamide;

4-[2-(3-chloro-4-methylphenyl)-4,5-difluorophenyl] benzenesulfonamide; and

4-[2-[3-chloro-4-(N,N-dimethylamino)phenyl]-4,5-difluorophenyl]benzenesulfonamide.

36. The method of claim 33 where the compound is 4-[4,5-difluoro-2-(3-chloro-4-fluorophenyl)phenyl]benzenesulfonamide, or a pharmaceutically-acceptable salt thereof.

37. The method of claim 33 where the compound is 4-[2-(3-chloro-4-methoxyphenyl)phenyl]benzenesulfonamide, or a pharmaceutically-acceptable salt thereof.

38. The method of claim 31 wherein each of $R^1$ and $R^4$ are hydrido; wherein each of $R^2$ and $R^3$ is independently selected from the group consisting of hydrido and halo; or wherein $R^2$ and $R^3$ together form —OCH$_2$O—; wherein each of $R^5$ and $R^9$ is hydrido; wherein each of $R^6$ through $R^8$ is independently selected from the group consisting of hydrido, lower alkyl, halo, and lower alkoxy; or wherein $R^6$ and $R^7$ together form —OCH$_2$O—; wherein $R^{10}$, $R^{11}$, $R^{13}$ and $R^{14}$ are hydrido; and wherein $R^{12}$ is lower alkylsulfonyl; or a pharmaceutically-acceptable salt thereof.

39. The method of claim 38 wherein each of $R^1$ and $R^4$ are hydrido; wherein each of $R^2$ and $R^3$ is independently selected from the group consisting of hydrido, fluoro, chloro and bromo; or wherein $R^2$ and $R^3$ together form —OCH$_2$O—; wherein each of $R^5$ and $R^9$ is hydrido; wherein each of $R^6$ through $R^8$ is independently selected from the group consisting of hydrido, methyl, ethyl, fluoro, chloro, bromo, methoxy, ethoxy, propoxy, and n-butoxy; or wherein $R^6$ and $R^7$ together form —OCH$_2$O—; wherein $R^{10}$, $R^{11}$, $R^{13}$ and $R^{14}$ are hydrido; and wherein $R^{12}$ is methylsulfonyl; or a pharmaceutically-acceptable salt thereof.

40. The method of claim 39 wherein said compound is selected from compounds, and their pharmaceutically acceptable salts, of the group consisting of 1-(4-fluorophenyl)-2-[4-(methylsulfonyl)phenyl] benzene;

1-(4-chlorophenyl)-2-[4-(methylsulfonyl)phenyl] benzene;

1-(3-chloro-4-methoxyphenyl)-2-[4-(methylsulfonyl) phenyl]benzene;

1-(3-fluoro-4-methoxyphenyl)-2-[4-(methylsulfonyl) phenyl]benzene;

1-(3-chloro-4-fluorophenyl)-2-[4-(methylsulfonyl) phenyl]benzene;

1-(4-fluorophenyl)-6-[4-(methylsulfonyl)phenyl]-1,3-benzodioxole;

1,2-difluoro-4-(4-fluorophenyl)-5-[4-(methylsulfonyl) phenyl]benzene;

1,2-difluoro-4-(4-methylphenyl)-5-[4-(methylsulfonyl) phenyl]benzene;

1-(3-chloro-4-methoxyphenyl)-4,5-difluoro-2-[4-(methylsulfonyl)phenyl]benzene;

1,2-difluoro-4-(3-fluoro-4-methoxyphenyl)-5-[4-(methylsulfonyl)phenyl]benzene;

1-(3,5-dichloro-4-methoxyphenyl)-4,5-difluoro-2-[4-(methylsulfonyl)phenyl]benzene;

1-(3,5-difluoro-4-methoxyphenyl)-4,5-difluoro-2-[4-(methylsulfonyl)phenyl]benzene;

1-(3-chloro-4-fluorophenyl)-4,5-difluoro-2-[4-(methylsulfonyl)phenyl]benzene;

5-[4,5-difluoro-2-[4-(methylsulfonyl)phenyl]phenyl]-1,3-benzodioxole;

1-(3-chloro-4-methylphenyl)-4,5-difluoro-2-[4-(methylsulfonyl)phenyl]benzene; and 2-chloro-4-[4,5-difluoro-2-[4-(methylsulfonyl)phenyl] phenyl]-N,N-dimethylbenzeneamine.

41. A method of treating inflammation or an inflammation-associated disorder in a subject, said method comprising administering to the subject having or susceptible to such inflammation or inflammation-associated disorder, a therapeutically-effective amount of a compound of Formula II

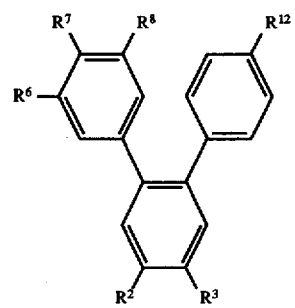

wherein each of $R^2$ and $R^3$ is independently selected from the group consisting of hydrido and halo; or wherein $R^2$ and $R^3$ together form —OCH$_2$O—; wherein each of $R^6$ through $R^8$ is independently selected from the group consisting of hydrido, lower alkyl, halo, lower alkoxy, lower haloalkyl, and lower dialkylamino; or wherein $R^6$ and $R^7$ together form —OCH$_2$O—; and wherein $R^{12}$ is selected from the group consisting of lower alkylsulfonyl and aminosulfonyl; or a pharmaceutically-acceptable salt thereof.

42. A method of treating inflammation or an inflammation-associated disorder in a subject, said method comprising administering to the subject having or susceptible to such inflammation or inflammation-associated disorder, a therapeutically-effective amount of a compound of Formula III

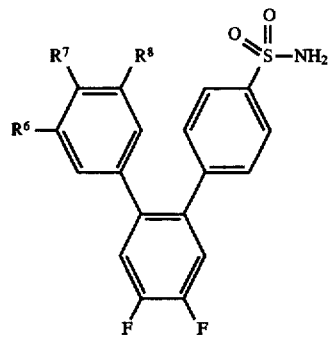

wherein each of $R^6$ through $R^8$ is independently selected from the group consisting of hydrido, halo, lower alkoxy, lower haloalkyl, amino, lower alkylamino, lower dialkylamino, and lower haloalkoxy; or wherein $R^6$ and $R^7$ together form —OCH$_2$O—; or a pharmaceutically-acceptable salt thereof.

43. The method of claim 29 for use in treatment of inflammation.

44. The method of claim 29 for use in treatment of an inflammation-associated disorder.

45. The method of claim 44 wherein the inflammation-associated disorder is arthritis.

46. The method of claim 44 wherein the inflammation-associated disorder is pain.

47. The method of claim 44 wherein the inflammation-associated disorder is fever.

* * * * *